US006326472B1

(12) United States Patent
Timans et al.

(10) Patent No.: US 6,326,472 B1
(45) Date of Patent: Dec. 4, 2001

(54) HUMAN RECEPTOR PROTEINS; RELATED REAGENTS AND METHODS

(75) Inventors: Jacqueline C. Timans; Johannes Eduard Maria Antonius Debets, both of Mountain View; Theodore R. Sana, East Palo Alto; J. Fernando Bazan, Menlo Park; Robert A. Kastelein, Redwood City, all of CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/173,151

(22) Filed: Oct. 14, 1998

Related U.S. Application Data

(60) Provisional application No. 60/095,987, filed on Aug. 10, 1998, provisional application No. 60/081,883, filed on Apr. 15, 1998, provisional application No. 60/078,416, filed on Mar. 18, 1998, provisional application No. 60/078,008, filed on Mar. 12, 1998, provisional application No. 60/065,776, filed on Nov. 17, 1997, and provisional application No. 60/062,066, filed on Oct. 15, 1997.

(51) Int. Cl.$^7$ .............................. C07K 16/28; C12P 21/08
(52) U.S. Cl. ................................. 530/389.1; 530/388.85; 424/185.1; 514/2; 536/23.5
(58) Field of Search ........................ 424/185.1; 530/350, 530/388.85, 389.1; 514/2; 536/23.5

(56) References Cited

U.S. PATENT DOCUMENTS 5,776,731 * 7/1998 Parnet et al. ......................... 435/69.1

FOREIGN PATENT DOCUMENTS

| WO 96/07739 | 3/1996 | (WO) . |
| WO 99/37772 | 7/1999 | (WO) . |
| WO 99/37773 | 7/1999 | (WO) . |

OTHER PUBLICATIONS

J. Fernando Bazan, et al., *Nature*, 379:591, Feb. 15, 1996. "A newly defined interleukin–1?".

Marcia P. Belvin & Kathryn V. Anderson, *Annu. Rev. Cell Dev. Biol.*, 12:393–416, 1996."A Conserved Signaling Pathway: The Drosophila TollDorsal Pathway".

Teresa L. Born, et al., *J. Biological Chemistry*, 273(45)29445–29450, Nov. 6, 1998. "Cloning of a Novel Receptor Subunit, AcPL, Required for Interleukin–18 Signaling".

D. Buck, *GenBank*, Accession No. Z68328, Oct. 31, 1997 & Dec. 1995. Definition: Human DNA sequence from cosmid cU72D5, between markers EXS366 and DXS87 on chromosome X.

Anne O. Chua and Ueli Gubler, *Nucleic Acids Research*, 17(23):10114, Dec. 11, 1989. "Sequence of the cDNA for the human fibroblast type interleukin–1 receptor".

Charles A. Dinarello, *Blood*, 77(8):1627–1652, Apr. 15, 1991. "Interleukin–1 and Interleukin–Antagonism".

Charles A. Dinarello, *The FASEB Journal*, 8:1314–1325, Dec. 1994. "The Interleukin–1 family: 10 years of discovery ".

Scott A. Greenfeder, et al., *J. Biological Chemistry*, 270(23):13757–13765, 1995. "Molecular Cloning and Characterization of a Second Subunit of the Interleukin 1 Receptor Complex".

U. Gubler, *GenBank*, Accession No. X16896, Mar. 22, 1995. Definition: Human mRNA for Interleukin–1 receptor (fibroblast type).

U. Gubler, *GenBank*, Accession No. 33801, Mar. 22, 1995. Definition: Interleukin 1 receptor precursor (AA–17 to 552) (human).

S. Guida, et al., *GenPept*, Accession No. 86325, Dec. 6, 1996. Definition: interleukin–1 receptor I precursor—chicken.

Steven K. Hanks & Anne Marie Quinn, *Methods in Enzymology*, 200:38–62, 1991. "[2]Protein Kinase Catalytic Domain Sequence Database: Identification of Conserved Features of Primary Structure and Classification of Family Members".

Dan Hultmark, *Nature*, 367:116–117, Jan. 13, 1994. "Ancient Relationships".

G.W. Ju, *GenBank*, Accession No. X85999, Jun. 27, 1995. Definition: M.musculus mRNA for interleukin 1 receptor accessory protein.

G.W. Ju, *GenPept*, Accession No. 887521, Jun. 27, 1995. Definition: Interleukin 1 receptor accessory protein (mouse).

T.W. Lovenberg, et al., *GenBank*, Accession No. U49065, Apr. 30, 1997. Definition: Human interleukin–1 receptorrelated protein mRNA, complete cds.

T.W. Lovenberg, et al. *GenBank*, Accession No. U49066, Apr. 30, 1997. Definition: Rattus norvegicus interleukin–1 receptor–related protein mRNA, complete cds.

Catherine J. McMahan, et al., *The EMBO Journal*, 10(10):2821–2832, Oct. 1991. "A novel IL–1 receptor, cloned from B cells by mammalian expression, is expressed in many cell types".

Donald Morisato & Kathryn V. Anderson, *Annu. Rev. Genetics*, 29:371–399, 1995. "Signaling Pathways that Establish the Dorsal–Ventral Pattern of the Drosophilia Embryo".

(List continued on next page.)

*Primary Examiner*—Lorraine Spector
*Assistant Examiner*—Eileen B. O'hara
(74) *Attorney, Agent, or Firm*—Hugh Wang; Edwin P. Ching; Sheela Mohan-Peterson

(57) ABSTRACT

Nucleic acids encoding mammalian, e.g., human receptors, purified receptor proteins and fragments thereof. Antibodies, both polyclonal and monoclonal, are also provided. Methods of using the compositions for both diagnostic and therapeutic utilities are provided.

14 Claims, No Drawings

OTHER PUBLICATIONS

D. Muzny, et al., *GenBank*, Accession No. AC005748, Oct. 5 & 16, 1998. Definition: Homo sapiens chromosome Xp22–164–166, Working Draft Sequence, 73 unordered pieces.

Haruki Okamura, et al., *Nature*, 378:88–91, Nov. 2, 1995. "Cloning of a new cytokine that induces IFN–g production by T cells".

Laura L. Parker, et al., *Nature*, 363:736–738, Jun. 24, 1993. "Phosphorylation and inactivation of the mitotic inhibitor Wee1 by the nim1/cdr1 kinase".

Patricia Parnet, et al., *J. Biological Chemistry*, 271(8):3967–3970, Feb. 23, 1996. "IL–1Rrp Is a Novel Receptor–like Molecule Similar to the Type I Interleulin–1 Receptor and Its Homologues T1/ST/2 and IL–1R AcP".

P. Parnet, et al., *GenBank*, Accession No. U43672, Feb. 28, 1996. Definition: Human putative transmembrane receptor IL–1Rrp mRNA, complete cds.

P.Parnet, et al., *GenBank*, Accession No. U43673, Feb. 28, 1996. Definition: Mus musculus putative transmembrane receptor IL–1Rrp mRNA, complete cds.

J. Partanen, et al., *GenPept*, Accession No. 120051, Nov. 1, 1995. Definition: Fibroblast Growth Factor Receptor 4 Precursor (FGFR–4) (human).

Roger A. Sayle & E. James Milner–White, *TIBS*, 20:374–376, Sep. 1995. "Rasmol: biomolecular graphics for all".

John E. Sims, et al., *Science*, 241:585–589, Jul. 29, 1998. "cDNA Expression Cloning of the IL–1 Receptor, a Member of the Immunoglobulin Superfamily."

J.E. Sims, *GenBank*, Accession No. M20658 M29752, Jun. 12, 1993. Definition: Mouse interleukin–1 receptor mRNA, complete cds.

J.E. Sims, *GenBank*, Accession No. X59769, May 26, 1992. Definition: Mouse IL–1R2 mRNA for type II interleukin–1 receptor, (cell line 70Z/3).

J.E. Sims, *GenBank*, Accession No. X59770, May 26, 1992. Definition: H. sapiens IL–1R2 mRNA for type II interleukin–1 receptor , (cell line CB23).

Shin–ichi Tominaga, *FEBS Letters*, 258(2):301–304, Dec. 1989. "A putative protein of a growth specific cDNA from BALB/c3T3 cells is highly similar to the extracellular portion of mouse interleukin 1 receptor".

S. Tominaga, et al., *GenBank*, Accession No. D12763, Sep. 3, 1992, May 20, 1996 and Jul. 1, 1997. Definition: Homo sapiens mRNA for ST2 protein.

S. Tominaga, et al., *GenBank*, Accession No. Y07519, Mar. 23, 1995. Definition: Mouse ST2 gene.

K. Yanagisawa, et al., *GenBank*, Accession No. D13695, Mar. 23, 1995. Definition: Mus musculus mRNA for ST2L protein, complete cds.

* cited by examiner

HUMAN RECEPTOR PROTEINS; RELATED REAGENTS AND METHODS

This filing is a conversion Utility Patent Application which claims priority to U.S. Ser. No. 60/065,776 filed Nov. 17, 1997; U.S. Ser. No. 60/078,008 filed Mar. 12, 1998; U.S. Ser. No. 60/081,883 filed Apr. 15, 1998; U.S. Ser. No. 60/095,987 filed Aug. 10, 1998; U.S. Ser. No. 60/078,416 filed Mar. 18, 1998; and U.S. Ser. No. 60/062,066 filed Oct. 15, 1997; each of which is incorporated herein by reference.

FIELD OF THE INVENTION

The present invention relates to compositions and methods for affecting mammalian physiology, including, e.g., morphogenesis or immune system function. In particular, it provides nucleic acids, proteins, and antibodies, e.g., which regulate development and/or the immune system along with related reagents and methods. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired polypeptide product. The carrier is frequently a plasmid having the capacity to incorporate cDNA for later replication and/or expression in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotential hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

The interleukin-1 family of proteins includes the IL-1α, the IL-1β, the IL-1RA, and recently the IL-1γ (also designated Interferon-Gamma Inducing Factor, IGIF). This related family of genes has been implicated in a broad range of biological functions. See Dinarello (1994) *FASEB J.* 8:1314–1325; Dinarello (1991) *Blood* 77:1627–1652; and Okamura, et al. (1995) *Nature* 378:88–91.

From the foregoing, it is evident that the discovery and development of new soluble proteins and their receptors, including ones similar to lymphokines, should contribute to new therapies. A number of degenerative or abnormal conditions directly or indirectly involve development, differentiation, or function, e.g., of the immune system and/or hematopoietic cells. In particular, the discovery and understanding of novel receptors for lymphokine-like molecules which enhance or potentiate the beneficial activities of other lymphokines, would be highly advantageous. The present invention provides new receptors for ligands exhibiting similarity to interleukin-1 like compositions and related compounds, and methods for their use.

SUMMARY OF THE INVENTION

The present invention is directed to novel receptors related to IL-1 receptors and their biological activities. These receptors, e.g., primate or rodent, are designated IL-1 receptor like molecular structures, IL-1 Receptor DNAX designation 8 (IL-1RD8), IL-1 Receptor DNAX designation 9 (IL-1RD9) and IL-1 Receptor DNAX designation 10 (IL-1RD10). The invention includes nucleic acids coding for the polypeptides themselves and methods for their production and use. The nucleic acids of the invention are characterized, in part, by their homology to cloned complementary DNA (cDNA) sequences enclosed herein.

In certain embodiments, the invention provides a composition of matter selected from the group of: an isolated or recombinant IL-1RD8 polypeptide comprising a segment of at least 12 contiguous amino acids of SEQ ID NO: 2 or 4, a natural sequence IL-1RD8 polypeptide comprising SEQ ID NO: 2 or 4, a fusion protein comprising IL-1RD8 sequence; an isolated or recombinant IL-1RD9 polypeptide comprising at least 12 contiguous amino acids of SEQ ID NO: 6, 8, 10, 12, 14, or 16; a natural sequence IL-1RD9 comprising SEQ ID NO: 6, 8, 10, 12, 14, or 16; a fusion protein comprising IL-1RD9 sequence; an isolated or recombinant IL-1RD10 polypeptide comprising at least 12 contiguous amino acids of SEQ ID NO: 18, 20, or 35; a natural sequence IL-1RD10 comprising SEQ ID NO: 18, 20, or 35; and a fusion protein comprising IL-1RD10 sequence. In various embodiments, the recombinant or isolated polypeptide comprises a segment identical to a corresponding portion of an IL-1RD8, as described, wherein: the number of contiguous amino acid residues is: at least 17 amino acids; at least 21 amino acids; or at least 25 amino acids; or to a corresponding portion of an IL-1RD9, as described, wherein the number of identical contiguous amino acid residues is: at least 17 amino acids; at least 21 amino acids; or at least 25 amino acids; or of an IL-1RD10, as described, wherein the number of identical contiguous amino acid residues is: at least 17 amino acids; at least 21 amino acids; or at least 25 amino acids.

In polypeptide embodiments, the invention provides a composition of matter wherein the IL-1RD8 comprises a mature sequence of Table 1; an IL-1RD9 that comprises a mature sequence of Table 2; an IL-1RD10 that comprises a mature sequence of Table 3; or the IL-1RD8, IL-1RD9, or IL-1RD10 polypeptide: is from a warm blooded animal, e.g., a primate, such as a human; comprises at least one polypeptide segment of SEQ ID NO: 2, 4, 6, 8, 10, 12, 14, 16, 18, 20, or 35; exhibits a plurality of portions having segments identical to specific sequence identifiers; is a natural allelic variant of a primate IL-1RD8; a primate or rodent IL-1RD9; or a primate IL-1RD10; has a length at least about 30 amino acids; exhibits at least two non-overlapping epitopes that are specific for: a primate IL-1RD8, a primate or rodent IL-1RD9, or primate IL-1RD10; exhibits a sequence identity over a length of at least about 20 amino acids to: a primate IL-1RD8, a primate or rodent IL-1RD9, or a primate IL-1RD10; has a molecular weight of at least 100 kD with natural glycosylation; is a synthetic polypeptide; is attached to a solid substrate; is conjugated to another chemical moiety; is a 5-fold or less substitution from natural sequence; or is a deletion or insertion variant from a natural sequence. Certain preferred embodiments include compositions comprising: a sterile IL-1RD8, IL-1RD9, or IL-1RD10 polypeptide; or the IL-1RD8, IL-1RD9, or IL-1RD10 polypeptide and a carrier, wherein the carrier is: an aqueous compound, including water, saline, and/or buffer; and/or formulated for oral, rectal, nasal, topical, or parenteral administration; a sterile IL-1RD8, IL-1RD9, or IL-1RD10 polypeptide; or the IL-1RD8, IL-1RD9, or IL-1RD10 polypeptide, as described, and a carrier, wherein the carrier is: an aqueous compound, including water, saline, and/or buffer; and/or formulated for oral, rectal, nasal, topical, or parenteral administration.

Certain fusion proteins are provided, e.g., comprising: mature polypeptide sequence of Table 1, 2, or 3; a detection or purification tag, including a FLAG, His6, or Ig sequence; or sequence of another receptor protein. Kit embodiments include a kit comprising such a polypeptide, and: a compartment comprising the polypeptide; and/or instructions for use or disposal of reagents in the kit.

In binding compound embodiments, the invention provides a binding compound comprising an antigen binding site from an antibody, which specifically binds to a natural: IL-1RD8, IL-1RD9, or IL-1RD10 polypeptide, wherein: the polypeptide is a primate or rodent protein; the binding compound is an Fv, Fab, or Fab2 fragment; the binding compound is conjugated to another chemical moiety; or the antibody: is raised to a polypeptide sequence of a mature polypeptide comprising sequence of Table 1, 2, or 3; is raised to a mature primate or rodent IL-1RD8; is raised to a purified human IL-1RD8; is raised to a purified mouse IL-1RD9; is immunoselected; is a polyclonal antibody; binds to a denatured IL-1RD8, IL-1RD9, or IL-1RD10; exhibits a Kd to antigen of at least 30 $\mu$M; is attached to a solid substrate, including a bead or plastic membrane; is in a sterile composition; or is detectably labeled, including a radioactive or fluorescent label; IL-1RD9 protein, wherein: the polypeptide is a primate or rodent protein; the binding compound is an Fv, Fab, or Fab2 fragment; the binding compound is conjugated to another chemical moiety; or the antibody: is raised against a polypeptide sequence of a mature polypeptide comprising sequence of Table 1, 2, or 3; is raised against a mature primate IL-1RD9; is raised to a purified human IL-1RD9; is immunoselected; is a polyclonal antibody; binds to a denatured IL-1RD9; exhibits a Kd to antigen of at least 30 $\mu$M; is attached to a solid substrate, including a bead or plastic membrane; is in a sterile composition; or is detectably labeled, including a radioactive or fluorescent label; IL-1RD10 protein, wherein: the polypeptide is a primate or rodent protein; the binding compound is an Fv, Fab, or Fab2 fragment; the binding compound is conjugated to another chemical moiety; or the antibody: is raised against a polypeptide sequence of a mature polypeptide comprising sequence of Table 1, 2, or 3; is raised against a mature primate IL-1RD10; is raised to a purified human IL-1RD10; is immunoselected; is a polyclonal antibody; binds to a denatured IL-1RD10; exhibits a Kd to antigen of at least 30 $\mu$M; is attached to a solid substrate, including a bead or plastic membrane; is in a sterile composition; or is detectably labeled, including a radioactive or fluorescent label. Kits are provided, e.g., those comprising the binding compound, and: a compartment comprising the binding compound; and/or instructions for use or disposal of reagents in the kit. Preferably, the kit is capable of making a qualitative or quantitative analysis.

Other embodiments include a composition comprising: a sterile binding compound, or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding a polypeptide or fusion protein, wherein: the IL-1RD8, IL-1RD9, or IL-1RD10 is from a mammal; said nucleic acid: encodes an antigenic polypeptide sequence of Table 1, 2, or 3; encodes a plurality of antigenic polypeptide sequences of Table 1, 2, or 3; exhibits at least about 30 nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said IL-1RD8, IL-1RD9, or IL-1RD10; comprises a plurality of nonoverlapping segments of at least 15, 18, 21, or 25 nucleotides from Table 1, 2, or 3; or is a PCR primer, PCR product, or mutagenesis primer. The invention further provides a cell comprising such a recombinant nucleic acid, e.g., where the cell is: a prokaryotic cell; a eukaryotic cell; a bacterial cell; a yeast cell; an insect cell; a mammalian cell; a mouse cell; a primate cell; or a human cell. Certain kit embodiments include a comprising the nucleic acid, and: a compartment comprising the nucleic acid; a compartment further comprising: a primate IL-1RD8, a primate or rodent IL-1RD9, or a primate IL-1RD10 polypeptide; and/or instructions for use or disposal of reagents in the kit.

Preferably, the kit is capable of making a qualitative or quantitative analysis.

In other nucleic acid embodiments, the nucleic acid is one which: hybridizes under wash conditions of 40° C. and less than 2M salt to either SEQ ID NO: 1, 3, 5, 7, 9, 11, 13, 15, 17, 19, or 34; or exhibits identity over a stretch of at least about 30 nucleotides to a primate IL-1RD8, a primate or rodent IL-1RD9, or a primate IL-1RD10. In various preferred embodiments: the wash conditions are: at 45° C. and/or 500 mM salt; at 55° C. and/or 150 mM salt; or the stretch is at least 55 nucleotides; or at least 75 nucleotides.

Methods of modulating physiology or development of a cell or tissue culture cells are provided, e.g., comprising contacting the cell with an agonist or antagonist of a primate IL-1RD8, a primate or rodent IL-1RD9, or a primate IL-1RD10. Preferably, the cell is transformed with a nucleic acid encoding either IL-1RDB, IL-1RD9, or IL-1RD10, and another IL-1R.

DETAILED DESCRIPTION OF THE PREFERRED EMBODIMENTS

Outline

I. General
II. Activities
III. Nucleic acids
   A. encoding fragments, sequence, probes
   B. mutations, chimeras, fusions
   C. making nucleic acids
   D. vectors, cells comprising
IV. Proteins, Peptides
   A. fragments, sequence, immunogens, antigens
   B. muteins
   C. agonists/antagonists, functional equivalents
   D. making proteins
V. Making Nucleic Acids, Proteins
   A. synthetic
   B. recombinant
   C. natural sources
VI. Antibodies
   A. polyclonals
   B. monoclonal
   C. fragments; Kd
   D. anti-idiotypic antibodies
   E. hybridoma cell lines
VII. Kits and Methods to Quantify IL-1Rs
   A. ELISA
   B. assay mRNA encoding
   C. qualitative/quantitative
   D. kits
VIII. Therapeutic Compositions, Methods
   A. combination compositions
   B. unit dose
   C. administration
IX. Ligands
I. General The present invention provides the amino acid sequence and DNA sequence of mammalian, herein, e.g., primate and rodent IL-1 receptor-like molecules, these molecules IL-1 Receptor DNAX designation 8 (IL-1RD8), IL-1 Receptor DNAX designation 9 (IL-1RD9) and IL-1 Receptor DNAX designation 10 (IL-1RD10) having particular defined properties, both structural and/or biological. These embodiments increase the number of members of the human IL-1 receptor-like family from 7 to at least 10. These receptors have been numbered internally as DNAX designations D1, D2, D3, D4, D5, D6, and now D8, D9, and D10, and are referred to as IL-1RD1 through D10. Various cDNAs encoding these molecules were obtained from primate, e.g., human, or rodent, e.g., mouse, cDNA sequence libraries. Other primate, rodent, or other mammalian counterparts would also be desired.

Some of the standard methods applicable are described or referenced, e.g., in Maniatis, et al. (1982) *Molecular Clonina, A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al. *Biology*, Greene Publishing Associates, Brooklyn, N.Y.; or Ausubel, et al. (1987 and periodic supplements) *Current Protocols in Molecular Biology,* Greene/Wiley, New York; each of which is incorporated herein by reference.

A partial nucleotide (SEQ ID NO: 1) and corresponding amino acid sequence (SEQ ID NO: 2) of a human IL-1RD8 coding segment is shown in Table 1. Supplemental human IL-1RD8 sequence is provided in SEQ ID NO: 3 and 4.

Similarly for primate IL-1RD9, partial nucleotide (SEQ ID NO: 5) and corresponding amino acid sequence (SEQ ID NO: 6) of a primate IL-1RD9 coding segment are provided. Supplemental primate IL-1RD9 is provided in SEQ ID NO: 7, 8, 9, and 10. Rodent embodiments of IL-1RD9 are provided in SEQ ID NO: 11, 12, with supplemental IL-1RD9 rodent sequence in SEQ ID NO: 13, 14, 15, and 16.

For an embodiment of primate, e.g., human, IL-1RD10, a partial nucleotide (SEQ ID NO: 17) and corresponding partial amino acid sequence (SEQ ID NO: 18) are provided in Table 3, with supplemental primate IL-1RD10 sequence provided in SEQ ID NO: 19, 20, 34, and 35.

Some sequences provided lack some portions of these receptors, as suggested by alignment of sequences (see Table 4). Note the alignment of IL-1RD10 with IL-1RD8 and D3s, which are alpha type receptor subunits, in Table 4. Table 4 also exhibits alignment of primate and rodent IL-1RD9.

It is to be understood that this invention is not limited to the particular methods, compositions and receptors specifically embodied herein, as such methods, compositions and receptors may, of course, vary. It is also to be understood that the terminology used herein is for the purpose of describing particular embodiments only, and is not intended to limit the scope of the present invention which is only limited by the appended claims.

As used herein, including the appended claims, singular forms of words such as "a," "an," and "the" include their corresponding plural referents unless the context clearly dictates otherwise. Thus, for example, reference to "an organism" includes one or more different organisms, reference to "a cell" includes one or more of such cells, and reference to "a method" includes reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application. Nothing herein is to be construed as an admission that the invention is not entitled to antedate any such disclosure by virtue of its prior invention. All publications, patent applications, patents, and other references mentioned herein are incorporated by reference in their entirety including all figures, graphs, and drawings.

TABLE 1

Nucleotide and amino acid sequences (see SEQ ID NO: 1 and 2) of a primate, e.g., human, IL-1 receptor like embodiment DNAX designated 8 (IL-1RD8).

| | | | | | | | | | | | | | | | | |
|---|---|---|---|---|---|---|---|---|---|---|---|---|---|---|---|---|
| TTA | CTG | CTC | ACA | CTA | TTA | GTG | TCA | ACA | ATG | CTC | ACT | GTA | TCT | TAT | ACC | 48 |
| Leu | Leu | Leu | Thr | Leu | Leu | Val | Ser | Thr | Met | Leu | Thr | Val | Ser | Tyr | Thr | |
| 1 | | | | 5 | | | | | 10 | | | | | 15 | | |
| TCT | TCT | GAT | TTT | CTT | TCA | GTG | GAT | GGC | TGC | ATT | GAC | TGG | TCA | GTG | GAT | 96 |
| Ser | Ser | Asp | Phe | Leu | Ser | Val | Asp | Gly | Cys | Ile | Asp | Trp | Ser | Val | Asp | |
| | | | 20 | | | | | 25 | | | | | 30 | | | |
| CTC | AAG | ACA | TAC | ATG | GCT | TTG | GCA | GGT | GAA | CCA | GTC | CGA | GTG | AAA | TGT | 144 |
| Leu | Lys | Thr | Tyr | Met | Ala | Leu | Ala | Gly | Glu | Pro | Val | Arg | Val | Lys | Cys | |
| | | 35 | | | | | 40 | | | | | 45 | | | | |
| GCC | CTT | TTC | TAC | AGT | TAT | ATT | CGT | ACC | AAC | TAT | AGC | ACG | GCC | CAG | AGC | 192 |
| Ala | Leu | Phe | Tyr | Ser | Tyr | Ile | Arg | Thr | Asn | Tyr | Ser | Thr | Ala | Gln | Ser | |
| | | 50 | | | | | 55 | | | | | 60 | | | | |
| ACT | GGG | CTC | AGG | CTT | ATG | TGG | TAC | AAA | AAC | AAA | GGT | GAT | TTG | GAA | GAG | 240 |
| Thr | Gly | Leu | Arg | Leu | Met | Trp | Tyr | Lys | Asn | Lys | Gly | Asp | Leu | Glu | Glu | |
| 65 | | | | | 70 | | | | | 75 | | | | | 80 | |
| CCC | ATC | ATC | TTT | TCA | GAG | GTC | AGG | ATG | AGC | AAA | GAG | GAA | GAT | TCA | ATA | 288 |
| Pro | Ile | Ile | Phe | Ser | Glu | Val | Arg | Met | Ser | Lys | Glu | Glu | Asp | Ser | Ile | |
| | | | | 85 | | | | | 90 | | | | | 95 | | |
| TGG | TTT | CAC | TCA | GCT | GAG | GCA | CAA | GAC | AGT | GGA | TTC | TAC | ACT | TGT | GTT | 336 |
| Trp | Phe | His | Ser | Ala | Glu | Ala | Gln | Asp | Ser | Gly | Phe | Tyr | Thr | Cys | Val | |
| | | | | 100 | | | | | 105 | | | | | 110 | | |
| TTA | AGG | AAC | TCA | ACA | TAT | TGC | ATG | AAG | GTG | TCA | ATG | TCC | TTG | ACT | GTT | 384 |
| Leu | Arg | Asn | Ser | Thr | Tyr | Cys | Met | Lys | Val | Ser | Met | Ser | Leu | Thr | Val | |
| | | | 115 | | | | | 120 | | | | | 125 | | | |
| GCA | GAG | AAT | GAA | TCA | GGC | CTG | TGC | TAC | AAC | AGC | AGG | ATC | CGC | TAT | TTA | 432 |
| Ala | Glu | Asn | Glu | Ser | Gly | Leu | Cys | Tyr | Asn | Ser | Arg | Ile | Arg | Tyr | Leu | |
| | | 130 | | | | | 135 | | | | | 140 | | | | |
| GAA | AAA | TCT | GAA | GTC | ACT | AAA | AGA | AAG | GAG | ATC | TCC | TGT | CCA | GAC | ATG | 480 |
| Glu | Lys | Ser | Glu | Val | Thr | Lys | Arg | Lys | Glu | Ile | Ser | Cys | Pro | Asp | Met | |
| 145 | | | | | 150 | | | | | 155 | | | | | 160 | |
| GAT | GAC | TTT | AAA | AAG | TCC | GAT | CAG | GAG | CCT | GAT | GTT | GTG | TGG | TAT | AAG | 528 |
| Asp | Asp | Phe | Lys | Lys | Ser | Asp | Gln | Glu | Pro | Asp | Val | Val | Trp | Tyr | Lys | |
| | | | | 165 | | | | | 170 | | | | | 175 | | |
| GAA | TGC | AAG | CCA | AAA | ATG | TGG | AGA | AGC | ATA | ATA | ATA | CAG | AAA | GGA | AAT | 576 |
| Glu | Cys | Lys | Pro | Lys | Met | Trp | Arg | Ser | Ile | Ile | Ile | Gln | Lys | Gly | Asn | |
| | | | 180 | | | | | 185 | | | | | 190 | | | |
| GCT | CTT | CTG | ATC | CAA | GAA | GTT | CAA | GAA | GAA | GAT | GGA | GGA | AAT | TAC | ACA | 624 |
| Ala | Leu | Leu | Ile | Gln | Glu | Val | Gln | Glu | Glu | Asp | Gly | Gly | Asn | Tyr | Thr | |
| | | | 195 | | | | | 200 | | | | | 205 | | | |
| TGT | GAA | CTT | AAA | TAT | GAA | GGA | AAA | CTT | GTA | AGA | CGA | ACA | ACT | GAA | TTG | 672 |
| Cys | Glu | Leu | Lys | Tyr | Glu | Gly | Lys | Leu | Val | Arg | Arg | Thr | Thr | Glu | Leu | |
| | 210 | | | | | 215 | | | | | 220 | | | | | |
| AAA | GTT | ACA | GCT | TTA | CTC | ACA | GAC | AAG | CCT | CCC | AAG | CCA | TTG | TTC | CCC | 720 |
| Lys | Val | Thr | Ala | Leu | Leu | Thr | Asp | Lys | Pro | Pro | Lys | Pro | Leu | Phe | Pro | |
| 225 | | | | | 230 | | | | | 235 | | | | | 240 | |
| ATG | GAG | AAT | CAG | CCA | AGT | GTT | ATA | GAT | GTC | CAG | CTG | GGT | AAG | CCT | CTG | 768 |
| Met | Glu | Asn | Gln | Pro | Ser | Val | Ile | Asp | Val | Gln | Leu | Gly | Lys | Pro | Leu | |
| | | | | 245 | | | | | 250 | | | | | 255 | | |
| AAC | ATC | CCC | TGC | AAA | GCA | TTC | TTC | GGA | TTC | AGT | GGA | GAG | TCT | GGG | CCA | 816 |
| Asn | Ile | Pro | Cys | Lys | Ala | Phe | Phe | Gly | Phe | Ser | Gly | Glu | Ser | Gly | Pro | |
| | | | 260 | | | | | 265 | | | | | 270 | | | |
| ATG | ATC | TAC | TGG | ATG | AAA | GGA | GAA | AAG | TTT | ATT | GAA | GAA | CTG | GCA | GGT | 864 |
| Met | Ile | Tyr | Trp | Met | Lys | Gly | Glu | Lys | Phe | Ile | Glu | Glu | Leu | Ala | Gly | |

TABLE 1-continued

|     | 275 |     |     |     |     | 280 |     |     |     |     | 285 |     |     |     |     |      |
|-----|-----|-----|-----|-----|-----|-----|-----|-----|-----|-----|-----|-----|-----|-----|-----|------|
| CAC | ATT | AGA | GAA | GGT | GAA | ATA | AGG | CTT | CTC | AAA | GAG | CAT | CTT | GGA | GAA | 912  |
| His | Ile | Arg | Glu | Gly | Glu | Ile | Arg | Leu | Leu | Lys | Glu | His | Leu | Gly | Glu |      |
|     |     | 290 |     |     |     |     | 295 |     |     |     | 300 |     |     |     |     |      |

```
AAA GAA GTT GAA TTG GCA CTC ATC TTT GAC TCA GTT GTG GAA GCT GAC       960
Lys Glu Val Glu Leu Ala Leu Ile Phe Asp Ser Val Val Glu Ala Asp
305             310                 315                 320

CTG GCG AAT TAT ACC TGC CAT GTT GAA AAC CGA AAT GGA CGG AAA CAT      1008
Leu Ala Asn Tyr Thr Cys His Val Glu Asn Arg Asn Gly Arg Lys His
                325                 330                 335

GCC AGT GTT TTG CTG CGT AAA AAG GAT TTA ATC TAT AAA ATT GAG CTT      1056
Ala Ser Val Leu Leu Arg Lys Lys Asp Leu Ile Tyr Lys Ile Glu Leu
                340                 345                 350

GCA GGG GGC CTG GGA GCA ATC TTC CTC CTC CTT GTA CTG CTG GTG GTC      1104
Ala Gly Gly Leu Gly Ala Ile Phe Leu Leu Leu Val Leu Leu Val Val
            355                 360                 365

ATT TAC AAA TGC TAC AAC ATT GAA TTG ATG CTC TTC TAC AGG CAG CAC      1152
Ile Tyr Lys Cys Tyr Asn Ile Glu Leu Met Leu Phe Tyr Arg Gln His
            370                 375                 380

TTT GGA GCT GAT GAA ACT AAT GAT GAC AAC AAG GAA TAT GAT GCC TAT      1200
Phe Gly Ala Asp Glu Thr Asn Asp Asp Asn Lys Glu Tyr Asp Ala Tyr
385             390                 395                 400

CTC TCT TAC ACA AAA GTG GAC CAA GAT ACT TTA GAC TGT GAC AAT CCT      1248
Leu Ser Tyr Thr Lys Val Asp Gln Asp Thr Leu Asp Cys Asp Asn Pro
                405                 410                 415

GAA GAA GAG CAG TTT GCT CTT GAA GTA CTG CCA GAT GTC CTG GAA AAA      1296
Glu Glu Glu Gln Phe Ala Leu Glu Val Leu Pro Asp Val Leu Glu Lys
                420                 425                 430

CAC TAT GGA TAT AAA CTC TTC ATC CCA GAA AGA GAC CTG ATT CCA AGT      1344
His Tyr Gly Tyr Lys Leu Phe Ile Pro Glu Arg Asp Leu Ile Pro Ser
            435                 440                 445

GGA AGT GCA TAC ATG GAA GAT CTC ACA AGA TAT GTT GAA CAA AGC AGA      1392
Gly Ser Ala Tyr Met Glu Asp Leu Thr Arg Tyr Val Glu Gln Ser Arg
            450                 455                 460

AGA CTT ATT ATC GTG CTA ACT CCA GAC TAT ATT CTC AGA CGG GGA TGG      1440
Arg Leu Ile Ile Val Leu Thr Pro Asp Tyr Ile Leu Arg Arg Gly Trp
465                 470                 475                 480

AGT ATT TTC GAA CTG GAA AGC AGA CTC CAT AAC ATG CTA GTC AGT GGA      1488
Ser Ile Phe Glu Leu Glu Ser Arg Leu His Asn Met Leu Val Ser Gly
                485                 490                 495

GAA ATC AAA GTG ATT TTG ATT GAG TGT ACA GAA TTA AAA GGG AAA GTG      1536
Glu Ile Lys Val Ile Leu Ile Glu Cys Thr Glu Leu Lys Gly Lys Val
                500                 505                 510

AAT TGC CAG GAA GTG GAA TCA CTA AAG CGT AGC ATC AAA CTT CTG TCC      1584
Asn Cys Gln Glu Val Glu Ser Leu Lys Arg Ser Ile Lys Leu Leu Ser
                515                 520                 525

CTG ATC AAG TGG AAG GGA TCC AAA AGC AGC AAA TTA AAT TCT AAG TTT      1632
Leu Ile Lys Trp Lys Gly Ser Lys Ser Ser Lys Leu Asn Ser Lys Phe
            530                 535                 540

TGG AAG CAC TTA GTA TAT GAA ATG CCC ATC AAG AAA AAA GAA ATG CTA      1680
Trp Lys His Leu Val Tyr Glu Met Pro Ile Lys Lys Lys Glu Met Leu
545                 550                 555                 560

CCT CGG TGC CAT GTT CTG GAC TCC GCA GAA CAA GGA CTT TTT GGA GAA      1728
Pro Arg Cys His Val Leu Asp Ser Ala Glu Gln Gly Leu Phe Gly Glu
                565                 570                 575

CTC CAG CCT                                                          1737
Leu Gln Pro
```

Updated and corrected nucleotide and amino acid sequences of primate, e.g., human, IL-1RD8 *SEQ ID NO: 3 and 4).

TABLE 1-continued

```
ATG AAG CCA CCA TTT CTT TTG GCC CTT GTG GTC TGT TCT GTA GTC AGC    48
Met Lys Pro Pro Phe Leu Leu Ala Leu Val Val Cys Ser Val Val Ser
 1               5                  10                  15

ACA AAT CTG AAG ATG GTG TCA AAG AGA AAT TCT GTG GAT GGC TGC ATT    96
Thr Asn Leu Lys Met Val Ser Lys Arg Asn Ser Val Asp Gly Cys Ile
             20                  25                  30

GAC TGG TCA GTG GAT CTC AAG ACA TAC ATG GCT TTG GCA GGT GAA CCA   144
Asp Trp Ser Val Asp Leu Lys Thr Tyr Met Ala Leu Ala Gly Glu Pro
         35                  40                  45

GTC CGA GTG AAA TGT GCC CTT TTC TAC AGT TAT ATT CGT ACC AAC TAT   192
Val Arg Val Lys Cys Ala Leu Phe Tyr Ser Tyr Ile Arg Thr Asn Tyr
     50                  55                  60

AGC ACG GCC CAG AGC ACT GGG CTC AGG CTT ATG TGG TAC AAA AAC AAA   240
Ser Thr Ala Gln Ser Thr Gly Leu Arg Leu Met Trp Tyr Lys Asn Lys
 65                  70                  75                  80

GGT GAT TTG GAA GAG CCC ATC ATC TTT TCA GAG GTC AGG ATG AGC AAA   288
Gly Asp Leu Glu Glu Pro Ile Ile Phe Ser Glu Val Arg Met Ser Lys
             85                  90                  95

GAG GAA GAT TCA ATA TGG TTT CAC TCA GCT GAG GCA CAA GAC AGT GGA   336
Glu Glu Asp Ser Ile Trp Phe His Ser Ala Glu Ala Gln Asp Ser Gly
        100                 105                 110

TTC TAC ACT TGT GTT TTA AGG AAC TCA ACA TAT TGC ATG AAG GTG TCA   384
Phe Tyr Thr Cys Val Leu Arg Asn Ser Thr Tyr Cys Met Lys Val Ser
    115                 120                 125

ATG TCC TTG ACT GTT GCA GAG AAT GAA TCA GGC CTG TGC TAC AAC AGC   432
Met Ser Leu Thr Val Ala Glu Asn Glu Ser Gly Leu Cys Tyr Asn Ser
        130                 135                 140

AGG ATC CGC TAT TTA GAA AAA TCT GAA GTC ACT AAA AGA AAG GAG ATC   480
Arg Ile Arg Tyr Leu Glu Lys Ser Glu Val Thr Lys Arg Lys Glu Ile
145                 150                 155                 160

TCC TGT CCA GAC ATG GAT GAC TTT AAA AAG TCC GAT CAG GAG CCT GAT   528
Ser Cys Pro Asp Met Asp Asp Phe Lys Lys Ser Asp Gln Glu Pro Asp
                165                 170                 175

GTT GTG TGG TAT AAG GAA TGC AAG CCA AAA ATG TGG AGA AGC ATA ATA   576
Val Val Trp Tyr Lys Glu Cys Lys Pro Lys Met Trp Arg Ser Ile Ile
            180                 185                 190

ATA CAG AAA GGA AAT GCT CTT CTG ATC CAA GAA GTT CAA GAA GAA GAT   624
Ile Gln Lys Gly Asn Ala Leu Leu Ile Gln Glu Val Gln Glu Glu Asp
        195                 200                 205

GGA GGA AAT TAC ACA TGT GAA CTT AAA TAT GAA GGA AAA CTT GTA AGA   672
Gly Gly Asn Tyr Thr Cys Glu Leu Lys Tyr Glu Gly Lys Leu Val Arg
    210                 215                 220

CGA ACA ACT GAA TTG AAA GTT ACA GCT TTA CTC ACA GAC AAG CCT CCC   720
Arg Thr Thr Glu Leu Lys Val Thr Ala Leu Leu Thr Asp Lys Pro Pro
225                 230                 235                 240

AAG CCA TTG TTC CCC ATG GAG AAT CAG CCA AGT GTT ATA GAT GTC CAG   768
Lys Pro Leu Phe Pro Met Glu Asn Gln Pro Ser Val Ile Asp Val Gln
                245                 250                 255

CTG GGT AAG CCT CTG AAC ATC CCC TGC AAA GCA TTC TTC GGA TTC AGT   816
Leu Gly Lys Pro Leu Asn Ile Pro Cys Lys Ala Phe Phe Gly Phe Ser
            260                 265                 270

GGA GAG TCT GGG CCA ATG ATC TAC TGG ATG AAA GGA GAA AAG TTT ATT   864
Gly Glu Ser Gly Pro Met Ile Tyr Trp Met Lys Gly Glu Lys Phe Ile
        275                 280                 285

GAA GAA CTG GCA GGT CAC ATT AGA GAA GGT GAA ATA AGG CTT CTC AAA   912
Glu Glu Leu Ala Gly His Ile Arg Glu Gly Glu Ile Arg Leu Leu Lys
    290                 295                 300

GAG CAT CTT GGA GAA AAA GAA GTT GAA TTG GCA CTC ATC TTT GAC TCA   960
Glu His Leu Gly Glu Lys Glu Val Glu Leu Ala Leu Ile Phe Asp Ser
```

TABLE 1-continued

```
      305                      310                      315                      320
GTT GTG GAA GCT GAC CTG GCG AAT TAT ACC TGC CAT GTT GAA AAC CGA  1008
Val Val Glu Ala Asp Leu Ala Asn Tyr Thr Cys His Val Glu Asn Arg
                    325                      330                  335

AAT GGA CGG AAA CAT GCC AGT GTT TTG CTG CGT AAA AAG GAT TTA ATC  1056
Asn Gly Arg Lys His Ala Ser Val Leu Leu Arg Lys Lys Asp Leu Ile
                340                      345                  350

TAT AAA ATT GAG CTT GCA GGG GGC CTG GGA GCA ATC TTC CTC CTC CTT  1104
Tyr Lys Ile Glu Leu Ala Gly Gly Leu Gly Ala Ile Phe Leu Leu Leu
                355                      360                  365

GTA CTG CTG GTG GTC ATT TAC AAA TGC TAC AAC ATT GAA TTG ATG CTC  1152
Val Leu Leu Val Val Ile Tyr Lys Cys Tyr Asn Ile Glu Leu Met Leu
                370                      375              380

TTC TAC AGG CAG CAC TTT GGA GCT GAT GAA ACT AAT GAT GAC AAC AAG  1200
Phe Tyr Arg Gln His Phe Gly Ala Asp Glu Thr Asn Asp Asp Asn Lys
385                      390                      395                  400

GAA TAT GAT GCC TAT CTC TCT TAC ACA AAA GTG GAC CAA GAT ACT TTA  1248
Glu Tyr Asp Ala Tyr Leu Ser Tyr Thr Lys Val Asp Gln Asp Thr Leu
                    405                      410                  415

GAC TGT GAC AAT CCT GAA GAA GAG CAG TTT GCT CTT GAA GTA CTG CCA  1296
Asp Cys Asp Asn Pro Glu Glu Glu Gln Phe Ala Leu Glu Val Leu Pro
                420                      425                  430

GAT GTC CTG GAA AAA CAC TAT GGA TAT AAA CTC TTC ATC CCA GAA AGA  1344
Asp Val Leu Glu Lys His Tyr Gly Tyr Lys Leu Phe Ile Pro Glu Arg
                435                      440                  445

GAC CTG ATT CCA AGT GGA ACA TAC ATG GAA GAT CTC ACA AGA TAT GTT  1392
Asp Leu Ile Pro Ser Gly Thr Tyr Met Glu Asp Leu Thr Arg Tyr Val
                450                      455              460

GAA CAA AGC AGA AGA CTT ATT ATC GTG CTA ACT CCA GAC TAT ATT CTC  1440
Glu Gln Ser Arg Arg Leu Ile Ile Val Leu Thr Pro Asp Tyr Ile Leu
465                      470                      475                  480

AGA CGG GGA TGG AGT ATT TTC GAA CTG GAA AGC AGA CTC CAT AAC ATG  1488
Arg Arg Gly Trp Ser Ile Phe Glu Leu Glu Ser Arg Leu His Asn Met
                    485                      490                  495

CTA GTC AGT GGA GAA ATC AAA GTG ATT TTG ATT GAG TGT ACA GAA TTA  1536
Leu Val Ser Gly Glu Ile Lys Val Ile Leu Ile Glu Cys Thr Glu Leu
                500                      505                  510

AAA GGG AAA GTG AAT TGC CAG GAA GTG GAA TCA CTA AAG CGT AGC ATC  1584
Lys Gly Lys Val Asn Cys Gln Glu Val Glu Ser Leu Lys Arg Ser Ile
                515                      520                  525

AAA CTT CTG TCC CTG ATC AAG TGG AAG GGA TCC AAA AGC AGC AAA TTA  1632
Lys Leu Leu Ser Leu Ile Lys Trp Lys Gly Ser Lys Ser Ser Lys Leu
                530                      535                  540

AAT TCT AAG TTT TGG AAG CAC TTA GTA TAT GAA ATG CCC ATC AAG AAA  1680
Asn Ser Lys Phe Trp Lys His Leu Val Tyr Glu Met Pro Ile Lys Lys
545                      550                      555                  560

AAA GAA ATG CTA CCT CGG TGC CAT GTT CTG GAC TCC GCA GAA CAA GGA  1728
Lys Glu Met Leu Pro Arg Cys His Val Leu Asp Ser Ala Glu Gln Gly
                    565                      570                  575

CTT TTT GGA GAA CTC CAG CCT ATA CCC TCT ATT GCC ATG ACC AGT ACT  1776
Leu Phe Gly Glu Leu Gln Pro Ile Pro Ser Ile Ala Met Thr Ser Thr
                580                      585                  590

TCA GCC ACT CTG GTG TCA TCT CAG GCT GAT CTC CCT GAA TTC CAC CCT  1824
Ser Ala Thr Leu Val Ser Ser Gln Ala Asp Leu Pro Glu Phe His Pro
                595                      600                  605

TCA GAT TCA ATG CAA ATC AGG CAC TGT TGC AGA GGT TAT AAA CAT GAG  1872
Ser Asp Ser Met Gln Ile Arg His Cys Cys Arg Gly Tyr Lys His Glu
                610                      615              620

ATA CCA GCC ACG ACC TTG CCA GTA CCT TCC TTA GGC AAC CAC CAT ACT  1920
```

TABLE 1-continued

```
Ile Pro Ala Thr Thr Leu Pro Val Pro Ser Leu Gly Asn His His Thr
625                 630                 635                 640

TAT TGT AAC CTG CCT CTG ACG CTA CTC AAC GGA CAG CTA CCC CTT AAT    1968
Tyr Cys Asn Leu Pro Leu Thr Leu Leu Asn Gly Gln Leu Pro Leu Asn
                645                 650                 655

AAC ACC CTG AAA GAT ACC CAG GAA TTT CAC AGG AAC AGT TCT TTG CTG    2016
Asn Thr Leu Lys Asp Thr Gln Glu Phe His Arg Asn Ser Ser Leu Leu
                660                 665                 670

CCT TTA TCC TCC AAA GAG CTT AGC TTT ACC AGT GAT ATT TGG            2058
Pro Leu Ser Ser Lys Glu Leu Ser Phe Thr Ser Asp Ile Trp
            675                 680                 685

TAG                                                                 2061
```

TABLE 2

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
AAA TAT GGC TAT AGC CTG TTT TTC CTT GAA AGA AAT GTG GCT CCA GGA      48
Lys Tyr Gly Tyr Ser Leu Phe Phe Leu Glu Arg Asn Val Ala Pro Gly
1                   5                   10                  15

GGA GTG TAT GCA GAA GAC ATT GTA AGC ATT ATT AAG AGA AGC AGA AGA      96
Gly Val Tyr Ala Glu Asp Ile Val Ser Ile Ile Lys Arg Ser Arg Arg
                20                  25                  30

GGA ATA TTT ATC TTA ACC CCC AAC TAT GTC AAT GGA CCC AGT ATC TTT     144
Gly Ile Phe Ile Leu Thr Pro Asn Tyr Val Asn Gly Pro Ser Ile Phe
                35                  40                  45

GAA CTA CAA GCA GCA GTG AAT CTT GCC TTG GAT GAT CAA ACA CTG AAA     192
Glu Leu Gln Ala Ala Val Asn Leu Ala Leu Asp Asp Gln Thr Leu Lys
            50                  55                  60

CTC ATT TTA ATT AAG TTC TGT TAC TTC CAA GAG CCA GAG TCT CTA CCT     240
Leu Ile Leu Ile Lys Phe Cys Tyr Phe Gln Glu Pro Glu Ser Leu Pro
65                  70                  75                  80

CAT CTC GTG AAA AAA GCT CTC AGG GTT TTG CCC ACA GTT ACT TGG AGA     288
His Leu Val Lys Lys Ala Leu Arg Val Leu Pro Thr Val Thr Trp Arg
                85                  90                  95

GGC TTA AAA TCA GTT CCT CCC AAT TCT AGG TTC TGG GCC AAA ATG CGC     336
Gly Leu Lys Ser Val Pro Pro Asn Ser Arg Phe Trp Ala Lys Met Arg
                100                 105                 110

TAC CAC ATG CCT GTG AAA AAT CTC TCA GGG ATT CAC GTG GGA ACC AGC     384
Tyr His Met Pro Val Lys Asn Leu Ser Gly Ile His Val Gly Thr Ser
            115                 120                 125

TCC AGA ATT ACC TCT AGG GAT TTT TTC AGT GGA AAG GAC TCC GTA GAA     432
Ser Arg Ile Thr Ser Arg Asp Phe Phe Ser Gly Lys Asp Ser Val Glu
            130                 135                 140

CAG AAA CCA TGG GGA GGA GCT CCC AGC CTC AAG GGA CGG TGC AAT GAG     480
Gln Lys Pro Trp Gly Gly Ala Pro Ser Leu Lys Gly Arg Cys Asn Glu
145                 150                 155                 160

CC                                                                  482
```

KYGYSLFFLERNVAPGGVYAEDIVSIIKRSRRGIFILTPNYVNGPSIFELQAAVNLALDDQTLKLILIK

FCYFQEPESLPHLVKKALRVLPTVTWRGLKSVPPNSRFWAKMRYHMPVKNLSGIHVGTSSRITSRDFFS

GKDSVEQKPWGGAP?LKG??NE?

Supplemental sequence of primate, e.g., human, IL-1RD9 (SEQ

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

ID NO: 7 and 8).

```
TTT CCT AGG AGC CCC TAT GAT GTA GCC TGT TGT GTC AAG ATG ATT TTA        48
Phe Pro Arg Ser Pro Tyr Asp Val Ala Cys Cys Val Lys Met Ile Leu
 1               5                  10                  15

GAA GTT AAG CCC CAG ACA AAT GCA TCC TGT GAG TAT TCC GCA TCA CAT        96
Glu Val Lys Pro Gln Thr Asn Ala Ser Cys Glu Tyr Ser Ala Ser His
             20                  25                  30

AAG CAA GAC CTA CTT CTT GGG AGC ACT GGC TCT ATT TCT TGC CCC AGT       144
Lys Gln Asp Leu Leu Leu Gly Ser Thr Gly Ser Ile Ser Cys Pro Ser
         35                  40                  45

CTC AGC TGC CAA AGT GAT GCA CAA AGT CCA GCG GTA ACC TGG TAC AAG       192
Leu Ser Cys Gln Ser Asp Ala Gln Ser Pro Ala Val Thr Trp Tyr Lys
     50                  55                  60

AAT GGA AAA CTC CTC TCT GTG GAA AGG AGC AAC CGA ATC GTA GTG GAT       240
Asn Gly Lys Leu Leu Ser Val Glu Arg Ser Asn Arg Ile Val Val Asp
 65                  70                  75                  80

GAA GTT TAT GAC TAT CAC CAG GGC ACA TAT GTA TGT GAT TAC ACT CAG       288
Glu Val Tyr Asp Tyr His Gln Gly Thr Tyr Val Cys Asp Tyr Thr Gln
                 85                  90                  95

TCG GAT ACT GTG AGT TCG TGG ACA GTC AGA GCT GTT GTT CAA GTG AGA       336
Ser Asp Thr Val Ser Ser Trp Thr Val Arg Ala Val Val Gln Val Arg
             100                 105                 110

ACC ATT GTG GGA GAC ACT AAA CTC AAA CCA GAT ATT CTG GAT CCT GTC       384
Thr Ile Val Gly Asp Thr Lys Leu Lys Pro Asp Ile Leu Asp Pro Val
         115                 120                 125

GAG GAC ACA CTG GAA GTA GAA CTT GGA AAG CCT TTA ACT ATT AGC TGC       432
Glu Asp Thr Leu Glu Val Glu Leu Gly Lys Pro Leu Thr Ile Ser Cys
     130                 135                 140

AAA GCA CGA TTT GGC TTT GAA AGG GTC TTT AAC CCT GTC ATA AAA TGG       480
Lys Ala Arg Phe Gly Phe Glu Arg Val Phe Asn Pro Val Ile Lys Trp
145                 150                 155                 160

TAC ATC AAA GAT TCT GAC CTA GAG TGG GAA GTC TCA GTA CCT GAG GCG       528
Tyr Ile Lys Asp Ser Asp Leu Glu Trp Glu Val Ser Val Pro Glu Ala
                 165                 170                 175

AAA AGT ATT AAA TCC ACT TTA AAG GAT GAA ATC ATT GAG CGT AAT ATC       576
Lys Ser Ile Lys Ser Thr Leu Lys Asp Glu Ile Ile Glu Arg Asn Ile
             180                 185                 190

ATC TTG GAA AAA GTC ACT CAG CGT GAT CTT CGC AGG AAG TTT GTT TGC       624
Ile Leu Glu Lys Val Thr Gln Arg Asp Leu Arg Arg Lys Phe Val Cys
         195                 200                 205

TTT GTC CAG AAC TCC ATT GGA AAC ACA ACC CAG TCC GTC CAA CTG AAA       672
Phe Val Gln Asn Ser Ile Gly Asn Thr Thr Gln Ser Val Gln Leu Lys
     210                 215                 220

GAA AAG AGA GGA GTG GTG CTC CTG TAC ATC CTG CTT GGC ACC ATC GGG       720
Glu Lys Arg Gly Val Val Leu Leu Tyr Ile Leu Leu Gly Thr Ile Gly
225                 230                 235                 240

ACC CTG GTG GCC GTG CTG GCG GCG AGT GCC CTC CTC TAC AGG CAC TGG       768
Thr Leu Val Ala Val Leu Ala Ala Ser Ala Leu Leu Tyr Arg His Trp
                 245                 250                 255

ATT GAA ATA GTG CTG CTG TAC CGG ACC TAC CAG AGC AAG GAT CAG ACG       816
Ile Glu Ile Val Leu Leu Tyr Arg Thr Tyr Gln Ser Lys Asp Gln Thr
             260                 265                 270

CTT GGG GAT AAA AAG GAT TTT GAT GCT TTC GTA TCC TAT GCA AAA TGG       864
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
Leu Gly Asp Lys Lys Asp Phe Asp Ala Phe Val Ser Tyr Ala Lys Trp
        275                 280                 285

AGC TCT TTT CCA AGT GAG GCC ACT TCA TCT CTG AGT GAA GAA CAC TTG            912
Ser Ser Phe Pro Ser Glu Ala Thr Ser Ser Leu Ser Glu Glu His Leu
        290                 295                 300

GCC CTG AGC CTA TTT CCT GAT GTT TTA GAA AAC AAA TAT GGA TAT AGC            960
Ala Leu Ser Leu Phe Pro Asp Val Leu Glu Asn Lys Tyr Gly Tyr Ser
305                 310                 315                 320

CTG TGT TTG CTT GAA AGA GAT GTG GCT CCA GGA GGA GTG TAT GCA GAA           1008
Leu Cys Leu Leu Glu Arg Asp Val Ala Pro Gly Gly Val Tyr Ala Glu
                325                 330                 335

GAC ATT GTG AGC ATT ATT AAG AGA AGC AGA GAG GTA ATA TTT ATC TTG           1056
Asp Ile Val Ser Ile Ile Lys Arg Ser Arg Glu Val Ile Phe Ile Leu
        340                 345                 350

AGC CCC AAC TAT GTC AAT GGA CCC AGT ATC TTT GAA CTA CAA GCA GCA           1104
Ser Pro Asn Tyr Val Asn Gly Pro Ser Ile Phe Glu Leu Gln Ala Ala
        355                 360                 365

GTG AAT CTT GCC TTG GAT GAT CAA ACA CTG AAA CTC ATT TTA ATT AAG           1152
Val Asn Leu Ala Leu Asp Asp Gln Thr Leu Lys Leu Ile Leu Ile Lys
        370                 375                 380

TTC TGT TAC TTC CAA GAG CCA GAG TCT CTA CCT CAT CTC GTG AAA AAA           1200
Phe Cys Tyr Phe Gln Glu Pro Glu Ser Leu Pro His Leu Val Lys Lys
385                 390                 395                 400

GCT CTC AGG GTT TTG CCC ACA GTT ACT TGG AGA GGA TTA AAA TCA GTT           1248
Ala Leu Arg Val Leu Pro Thr Val Thr Trp Arg Gly Leu Lys Ser Val
                405                 410                 415

CCT CCC AAT TCT AGG TTC TGG GCC AAA ATG CGC TAC CAC ATG CCT GTG           1296
Pro Pro Asn Ser Arg Phe Trp Ala Lys Met Arg Tyr His Met Pro Val
        420                 425                 430

AAA AAC TCT CAG GGA TTC ACG TGG AAC CAG CTC AGA ATT ACC TCT AGG           1344
Lys Asn Ser Gln Gly Phe Thr Trp Asn Gln Leu Arg Ile Thr Ser Arg
        435                 440                 445

ATT TTT CAG TGG AAA GGA CTC AGT AGA ACA GAA ACC ACT GGG GAG GAG           1392
Ile Phe Gln Trp Lys Gly Leu Ser Arg Thr Glu Thr Thr Gly Glu Glu
        450                 455                 460

CTC CCA GCC TAA                                                           1404
Leu Pro Ala
465
```

Supplemental sequence of primate, e.g., human, IL-1RD9 (SEQ ID NO: 9 and 10).

```
CCAGCGTGGT GGAATTCGGA TACTCAGGGC AGAGTTCTGA ATCTCAAAAC ACTTTAATCT            60

GGCAAAGGAA TGAAGTTATT GGAGTGATGA CAGGAACACG GGAGAACA ATG CTC TGT           117
                                                   Met Leu Cys
                                                        1

TTG GGC TGG ATA TTT CTT TGG CTT GTT GCA GGA GAG CGA ATT AAA GGA            165
Leu Gly Trp Ile Phe Leu Trp Leu Val Ala Gly Glu Arg Ile Lys Gly
        5                   10                  15

TTT AAT ATT TCA GGT TGT TCC ACA AAA AAA CTC CTT TGG ACA TAT TCT            213
Phe Asn Ile Ser Gly Cys Ser Thr Lys Lys Leu Leu Trp Thr Tyr Ser
20                  25                  30                  35

ACA AGG AGT GAA GAG GAA TTT GTC TTA TTT TGT GAT TTA CCA GAG CCA            261
Thr Arg Ser Glu Glu Glu Phe Val Leu Phe Cys Asp Leu Pro Glu Pro
        40                  45                  50
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

| | |
|---|---|
| CAG AAA TCA CAT TTC TGC CAC AGA AAT CGA CTC TCA CCA AAA CAA GTC<br>Gln Lys Ser His Phe Cys His Arg Asn Arg Leu Ser Pro Lys Gln Val<br>              55                    60                 65 | 309 |
| CCT GAG CAC CTG CCC TTC ATG GGT AGT AAC GAC CTA TCT GAT GTC CAA<br>Pro Glu His Leu Pro Phe Met Gly Ser Asn Asp Leu Ser Asp Val Gln<br>        70                    75                    80 | 357 |
| TGG TAC CAA CAA CCT TCG AAT GGA GAT CCA TTA GAG GAC ATT AGG AAA<br>Trp Tyr Gln Gln Pro Ser Asn Gly Asp Pro Leu Glu Asp Ile Arg Lys<br> 85                   90                    95 | 405 |
| AGC TAT CCT CAC ATC ATT CAG GAC AAA TGT ACC CTT CAC TTT TTG ACC<br>Ser Tyr Pro His Ile Ile Gln Asp Lys Cys Thr Leu His Phe Leu Thr<br>100               105              110             115 | 453 |
| CCA GGG GTG AAT AAT TCT GGG TCA TAT ATT TGT AGA CCC AAG ATG ATT<br>Pro Gly Val Asn Asn Ser Gly Ser Tyr Ile Cys Arg Pro Lys Met Ile<br>                120                  125             130 | 501 |
| AAG AGC CCC TAT GAT GTA GCC TGT TGT GTC AAG ATG ATT TTA GAA GTT<br>Lys Ser Pro Tyr Asp Val Ala Cys Cys Val Lys Met Ile Leu Glu Val<br>               135                 140            145 | 549 |
| AAG CCC CAG ACA AAT GCA TCC TGT GAG TAT TCC GCA TCA CAT AAG CAA<br>Lys Pro Gln Thr Asn Ala Ser Cys Glu Tyr Ser Ala Ser His Lys Gln<br>             150                 155             160 | 597 |
| GAC CTA CTT CTT GGG AGC ACT GGC TCT ATT TCT TGC CCC AGT CTC AGC<br>Asp Leu Leu Leu Gly Ser Thr Gly Ser Ile Ser Cys Pro Ser Leu Ser<br>     165                  170             175 | 645 |
| TGC CAA AGT GAT GCA CAA AGT CCA GCG GTA ACC TGG TAC AAG AAT GGA<br>Cys Gln Ser Asp Ala Gln Ser Pro Ala Val Thr Trp Tyr Lys Asn Gly<br>180               185              190             195 | 693 |
| AAA CTC CTC TCT GTG GAA AGG AGC AAC CGA ATC GTA GTG GAT GAA GTT<br>Lys Leu Leu Ser Val Glu Arg Ser Asn Arg Ile Val Val Asp Glu Val<br>             200              205            210 | 741 |
| TAT GAC TAT CAC CAG GGC ACA TAT GTA TGT GAT TAC ACT CAG TCG GAT<br>Tyr Asp Tyr His Gln Gly Thr Tyr Val Cys Asp Tyr Thr Gln Ser Asp<br>             215             220           225 | 789 |
| ACT GTG AGT TCG TGG ACA GTC AGA GCT GTT GTT CAA GTG AGA ACC ATT<br>Thr Val Ser Ser Trp Thr Val Arg Ala Val Val Gln Val Arg Thr Ile<br>         230              235           240 | 837 |
| GTG GGA GAC ACT AAA CTC AAA CCA GAT ATT CTG GAT CCT GTC GAG GAC<br>Val Gly Asp Thr Lys Leu Lys Pro Asp Ile Leu Asp Pro Val Glu Asp<br>245               250              255 | 885 |
| ACA CTG GAA GTA GAA CTT GGA AAG CCT TTA ACT ATT AGC TGC AAA GCA<br>Thr Leu Glu Val Glu Leu Gly Lys Pro Leu Thr Ile Ser Cys Lys Ala<br>260               265              270             275 | 933 |
| CGA TTT GGC TTT GAA AGG GTC TTT AAC CCT GTC ATA AAA TGG TAC ATC<br>Arg Phe Gly Phe Glu Arg Val Phe Asn Pro Val Ile Lys Trp Tyr Ile<br>             280              285            290 | 981 |
| AAA GAT TCT GAC CTA GAG TGG GAA GTC TCA GTA CCT GAG GCG AAA AGT<br>Lys Asp Ser Asp Leu Glu Trp Glu Val Ser Val Pro Glu Ala Lys Ser<br>             295              300            305 | 1029 |
| ATT AAA TCC ACT TTA AAG GAT GAA ATC ATT GAG CGT AAT ATC ATC TTG<br>Ile Lys Ser Thr Leu Lys Asp Glu Ile Ile Glu Arg Asn Ile Ile Leu<br>         310              315            320 | 1077 |
| GAA AAA GTC ACT CAG CGT GAT CTT CGC AGG AAG TTT GTT TGC TTT GTC<br>Glu Lys Val Thr Gln Arg Asp Leu Arg Arg Lys Phe Val Cys Phe Val<br>325               330              335 | 1125 |

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
CAG AAC TCC ATT GGA AAC ACA ACC CAG TCC GTC CAA CTG AAA GAA AAG     1173
Gln Asn Ser Ile Gly Asn Thr Thr Gln Ser Val Gln Leu Lys Glu Lys
340                 345                 350                 355

AGA GGA GTG GTG CTC CTG TAC ATC CTG CTT GGC ACC ATC GGG ACC CTG     1221
Arg Gly Val Val Leu Leu Tyr Ile Leu Leu Gly Thr Ile Gly Thr Leu
                360                 365                 370

GTG GCC GTG CTG GCG GCG AGT GCC CTC CTC TAC AGG CAC TGG ATT GAA     1269
Val Ala Val Leu Ala Ala Ser Ala Leu Leu Tyr Arg His Trp Ile Glu
            375                 380                 385

ATA GTG CTG CTG TAC CGG ACC TAC CAG AGC AAG GAT CAG ACG CTT GGG     1317
Ile Val Leu Leu Tyr Arg Thr Tyr Gln Ser Lys Asp Gln Thr Leu Gly
        390                 395                 400

GAT AAA AAG GAT TTT GAT GCT TTC GTA TCC TAT GCA AAA TGG AGC TCT     1365
Asp Lys Lys Asp Phe Asp Ala Phe Val Ser Tyr Ala Lys Trp Ser Ser
    405                 410                 415

TTT CCA AGT GAG GCC ACT TCA TCT CTG AGT GAA GAA CAC TTG GCC CTG     1413
Phe Pro Ser Glu Ala Thr Ser Ser Leu Ser Glu Glu His Leu Ala Leu
420                 425                 430                 435

AGC CTA TTT CCT GAT GTT TTA GAA AAC AAA TAT GGA TAT AGC CTG TGT     1461
Ser Leu Phe Pro Asp Val Leu Glu Asn Lys Tyr Gly Tyr Ser Leu Cys
                440                 445                 450

TTG CTT GAA AGA GAT GTG GCT CCA GGA GGA GTG TAT GCA GAA GAC ATT     1509
Leu Leu Glu Arg Asp Val Ala Pro Gly Gly Val Tyr Ala Glu Asp Ile
            455                 460                 465

GTG AGC ATT ATT AAG AGA AGC AGA AGA GGA ATA TTT ATC TTG AGC CCC     1557
Val Ser Ile Ile Lys Arg Ser Arg Arg Gly Ile Phe Ile Leu Ser Pro
        470                 475                 480

AAC TAT GTC AAT GGA CCC AGT ATC TTT GAA CTA CAA GCA GCA GTG AAT     1605
Asn Tyr Val Asn Gly Pro Ser Ile Phe Glu Leu Gln Ala Ala Val Asn
    485                 490                 495

CTT GCC TTG GAT GAT CAA ACA CTG AAA CTC ATT TTA ATT AAG TTC TGT     1653
Leu Ala Leu Asp Asp Gln Thr Leu Lys Leu Ile Leu Ile Lys Phe Cys
500                 505                 510                 515

TAC TTC CAA GAG CCA GAG TCT CTA CCT CAT CTC GTG AAA AAA GCT CTC     1701
Tyr Phe Gln Glu Pro Glu Ser Leu Pro His Leu Val Lys Lys Ala Leu
                520                 525                 530

AGG GTT TTG CCC ACA GTT ACT TGG AGA GGC TTA AAA TCA GTT CCT CCC     1749
Arg Val Leu Pro Thr Val Thr Trp Arg Gly Leu Lys Ser Val Pro Pro
            535                 540                 545

AAT TCT AGG TTC TGG GCC AAA ATG CGC TAC CAC ATG CCT GTG AAA AAC     1797
Asn Ser Arg Phe Trp Ala Lys Met Arg Tyr His Met Pro Val Lys Asn
        550                 555                 560

TCT CAG GGA TTC ACG TGG AAC CAG CTC AGA ATT ACC TCT AGG ATT TTT     1845
Ser Gln Gly Phe Thr Trp Asn Gln Leu Arg Ile Thr Ser Arg Ile Phe
    565                 570                 575

CAG TGG AAA GGA CTC AGT AGA ACA GAA ACC ACT GGG AGG AGC TCC CAG     1893
Gln Trp Lys Gly Leu Ser Arg Thr Glu Thr Thr Gly Arg Ser Ser Gln
580                 585                 590                 595

CCT AAG GAA TGG TGAAATGAGC CCTGGAGCCC CCTCCAGTCC AGTCCCTGGG         1945
Pro Lys Glu Trp

ATAGAGATGT TGCTGGACAG AACTCACAGC TCTGTGTGTG TGTGTTCAGG CTGATAGGAA   2005

ATTCAAAGAG TCTCCTGCCA GCACCAAGCA AGCTTGATGG ACAATGGAAT GGGATTGAGA   2065
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
CTGTGGTTTA GAGCCTTTGA TTTCCTGGAC TGGACAGACG GCGAGTGAAT TCTCTAGACC    2125

TTGGGTACTT TCAGTACACA ACACCCCTAA GATTTCCCAG TGGTCCGAGC AGAATCAGAA    2185

AATACAGCTA CTTCTGCCTT ATGGCTAGGG AACTGTCATG TCTACCATGT ATTGTACATA    2245

TGACTTTATG TATACTTGCA ATCAAATAAA TATTATTTTA TTAGAAAAAA AAAAAAAAAG    2305

GGCGGCCGC                                                            2314
```

MLCLGWIFLWLVAGERIKGFNISGCSTKKLLWTYSTRSEEEFVLFCDLPEPQKSHFCHRNRLSPKQVPE

HLPFMGSNDLSDVQWYQQPSNGDPLEDIRKSYPHIIQDKCTLHFLTPGVNNSGSYICRPKMIKSPYDVA

CCVKMILEVKPQTNASCEYSASHKQDLLLGSTGSISCPSLSCQSDAQSPAVTWYKNGKLLSVERSNRIV

VDEVYDYHQGTYVCDYTQSDTVSSWTVRAVVQVRTIVGDTKLKPDILDPVEDTLEVELGKPLTISCKAR

FGFERVFNPVIKWYIKDSDLEWEVSVPEAKSIKSTLKDEIIERNIILEKVTQRDLRRKFVCFVQNSIGN

TTQSVQLKEKRGVVLLYILLGTIGTLVAVLAASALLYRHWIEIVLLYRTYQSKDQTLGDKKDFDAFVSY

AKWSSFPSEATSSLSEEHLALSLFPDVLENKYGYSLCLLERDVAPGGVYAEDIVSIIKRSRRGIFILSP

NYVNGPSIFELQAAVNLALDDQTLKLILIKFCYFQEPESLPHLVKKALRVLPTVTWRGLKSVPPNSRFW

AKMRYHMPVKNSQGFTWNQLRITSRIFQWKGLSRTETTGRSSQPKEW

Nucleotide and amino acid sequences (see SEQ ID NO: 11 and 12) of a
rodent, e.g., mouse, embodiment of IL-1RD9. Single clone sequence
from thymus from 4 week old male C57BL/6J.
GCA GCA GTG AAT CTT GCC TTG GTT GAT CAG ACA CTG AAG TTG ATT TTA      48
Ala Ala Val Asn Leu Ala Leu Val Asp Gln Thr Leu Lys Leu Ile Leu
  1               5                  10                  15

ATT AAG TTC TGT TCC TTC CAA GAG CCA GAA TCT CTT CCT TAC CTT GTC      96
Ile Lys Phe Cys Ser Phe Gln Glu Pro Glu Ser Leu Pro Tyr Leu Val
                 20                  25                  30

AAA AAG GCT CTG CGG GTT CTC CCC ACA GTC ACA TGG AAA GGC TTG AAG     144
Lys Lys Ala Leu Arg Val Leu Pro Thr Val Thr Trp Lys Gly Leu Lys
         35                  40                  45

TCG GTC CAC GCC AGT TCC AGG TTC TGG ACC CAA ATT CGT TAC CAC ATG     192
Ser Val His Ala Ser Ser Arg Phe Trp Thr Gln Ile Arg Tyr His Met
    50                  55                  60

CCT GTG AAG AAC TCC AAC AGG TTT ATG TTC AAC GGG CTC AGA ATT TTC     240
Pro Val Lys Asn Ser Asn Arg Phe Met Phe Asn Gly Leu Arg Ile Phe
65                  70                  75                  80

CTG AAG GGC TTT TCC CCT GAA AAG GAC CTA GTG ACA CAG AAA CCC CTG     288
Leu Lys Gly Phe Ser Pro Glu Lys Asp Leu Val Thr Gln Lys Pro Leu
                 85                  90                  95

GAA GGA ATG CCC AAG TCT GGG AAT GAC CAC GGA GCT CAG AAC CTC CTT     336
Glu Gly Met Pro Lys Ser Gly Asn Asp His Gly Ala Gln Asn Leu Leu
            100                 105                 110

CTC TAC AGT GAC CAG AAG AGG TGC TGATGGGTAG AACTTGCTGT GTGGATCAGG    390
Leu Tyr Ser Asp Gln Lys Arg Cys
        115                 120

CTGATAGAAA TTGAGCCTTT CTGCTCTCAG TGCCAAGCAA GCTTGACAGG CAGTGGAATG   450

AAGCGGCATC TGTGGTTTTA GGGTCTGGGT TCCTGGAACA GACACAGAGC AATACTCCAG   510

ACCTCTGCCG TGTGCTTAGC ACACATTTCC CTGAGAGTTC CCAAGTAGCC TGAACAGAAT   570

CAACAGAAAT AGCTCCATGG GCTGTCCAAC ATTCATGCAC GCATGCCTGT TTTGCACTAT   630
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
ATATATGAAT TTATCATACG TTTGTGTGTG TATATGCATT CAGATAAATA GGATTTTATT    690

TTGTTCGATA CGAGTGATTG AAACTCCATT TAAAGCCCTT CTGTAAAGAA ATTTTGCTGC    750

AAAAAAAAAA AAAAAAAAA                                                  768

AAVNLALVDQTLKLILIKFCSFQEPESLPYLVKKALRVLPTVTWKGLKSVHASSRFWTQIRYHMPVKNS

NRFMFNGLRIFLKGFSPEKDLVTQKPLDRMPKSGNDHGAQNLLLYSD
```

Supplemental sequence of rodent, e.g., mouse, IL-1RD9 (SEQ ID NO: 13 and 14). Putative signal processing site is indicated, but actual may depend upon cell type, and may be at a different nearby site.

```
ATG TCT GTT TGG CTG GTG TTC TTG GTT TGT GCA GGA GAG AAG ACC ACA     48
Met Ser Val Trp Leu Val Phe Leu Val Cys Ala Gly Glu Lys Thr Thr
-17     -15             -10                 -5

GGA TTT AAT CAT TCA GCT TGT GCC ACC AAA AAT TCT GTG GAC ATA TTC     96
Gly Phe Asn His Ser Ala Cys Ala Thr Lys Asn Ser Val Asp Ile Phe
  1               5                   10                      15

GCA AGG GGT GCA GAG AAT TTT GTC TAT TTT GTG ACT TAC AAG AGC TTC    144
Ala Arg Gly Ala Glu Asn Phe Val Tyr Phe Val Thr Tyr Lys Ser Phe
              20                  25                  30

AGG AGC AAA AAT TCT CCC ATG CAA GTC AAC TGT CAC CAA CAC AAA GTC    192
Arg Ser Lys Asn Ser Pro Met Gln Val Asn Cys His Gln His Lys Val
              35                  40                  45

TGC TCA CAA ACT TGC AGT GGC AGT CAG AAG GAC TTA TCT GAT GTC CAG    240
Cys Ser Gln Thr Cys Ser Gly Ser Gln Lys Asp Leu Ser Asp Val Gln
              50                  55                  60

TGG TAC ATG CAA CCT CGG AGT GGA AGT CCA CTA GAG GAG ATC AGT AGA    288
Trp Tyr Met Gln Pro Arg Ser Gly Ser Pro Leu Glu Glu Ile Ser Arg
              65                  70                  75

AAC TCT CCC CAT ATG CAG AGT GAA GGC ATG CTG CAT ATA TTG GCC CCA    336
Asn Ser Pro His Met Gln Ser Glu Gly Met Leu His Ile Leu Ala Pro
 80               85                  90                      95

CAG ACG AAC AGC ATT TGG TCA TAT ATT TGT AGA CCC AGA ATT AGG AGC    384
Gln Thr Asn Ser Ile Trp Ser Tyr Ile Cys Arg Pro Arg Ile Arg Ser
                 100                 105                 110

CCC CAG GAT ATG GCC TGT TGT ATC AAG ACA GTC TTA GAA GTT AAG CCT    432
Pro Gln Asp Met Ala Cys Cys Ile Lys Thr Val Leu Glu Val Lys Pro
             115                 120                 125

CAG AGA AAC GTG TCC TGT GGG AAC ACA GCA CAA GAT GAA CAA GTC CTA    480
Gln Arg Asn Val Ser Cys Gly Asn Thr Ala Gln Asp Glu Gln Val Leu
             130                 135                 140

CTT CTT GGC AGT ACT GGC TCC ATT CAT TGT CCC AGT CTC AGC TGC CAA    528
Leu Leu Gly Ser Thr Gly Ser Ile His Cys Pro Ser Leu Ser Cys Gln
145                 150                 155

AGT GAT GTA CAG AGT CCA GAG ATG ACC TGG TAC AAG GAT GGA AGA CTA    576
Ser Asp Val Gln Ser Pro Glu Met Thr Trp Tyr Lys Asp Gly Arg Leu
160                 165                 170                 175

CTT CCT GAG CAC AAG AAA AAT CCA ATT GAG ATG GCA GAT ATT TAT GTT    624
Leu Pro Glu His Lys Lys Asn Pro Ile Glu Met Ala Asp Ile Tyr Val
                 180                 185                 190

TTT AAT CAA GGC TTG TAT GTA TGT GAT TAC ACA CAG TCA GAT AAT GTG    672
Phe Asn Gln Gly Leu Tyr Val Cys Asp Tyr Thr Gln Ser Asp Asn Val
             195                 200                 205
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
AGT TCC TGG ACA GTC CGA GCT GTG GTT AAA GTG AGA ACC ATT GGT AAG      720
Ser Ser Trp Thr Val Arg Ala Val Val Lys Val Arg Thr Ile Gly Lys
        210                 215                 220

GAC ATC AAT GTG AAG CCG GAA ATT CTG GAT CCC ATT ACA GAT ACA CTG      768
Asp Ile Asn Val Lys Pro Glu Ile Leu Asp Pro Ile Thr Asp Thr Leu
    225                 230                 235

GAC GTA GAG CTT GGA AAG CCT TTA ACT CTC CCC TGC AGA GTA CAG TTT      816
Asp Val Glu Leu Gly Lys Pro Leu Thr Leu Pro Cys Arg Val Gln Phe
240                 245                 250                 255

GGC TTC CAA AGA CTT TCA AAG CCT GTG ATA AAG TGG TAT GTC AAA GAA      864
Gly Phe Gln Arg Leu Ser Lys Pro Val Ile Lys Trp Tyr Val Lys Glu
                260                 265                 270

TCT ACA CAG GAG TGG GAA ATG TCA GTA TTT GAG GAG AAA AGA ATT CAA      912
Ser Thr Gln Glu Trp Glu Met Ser Val Phe Glu Glu Lys Arg Ile Gln
            275                 280                 285

TCC ACT TTC AAG AAT GAA GTC ATT GAA CGT ACC ATC TTC TTG AGA GAA      960
Ser Thr Phe Lys Asn Glu Val Ile Glu Arg Thr Ile Phe Leu Arg Glu
        290                 295                 300

GTT ACC CAG AGA GAT CTC AGC AGA AAG TTT GTT TGC TTT GCC CAG AAC     1008
Val Thr Gln Arg Asp Leu Ser Arg Lys Phe Val Cys Phe Ala Gln Asn
    305                 310                 315

TCC ATT GGG AAC ACA ACA CGG ACC ATA CGG CTG AGG AAG AAG GAA GAG     1056
Ser Ile Gly Asn Thr Thr Arg Thr Ile Arg Leu Arg Lys Lys Glu Glu
320                 325                 330                 335

GTG GTG TTT GTA TAC ATC CTT CTC GGC ACG GCC TTG ATG CTG GTG GGC     1104
Val Val Phe Val Tyr Ile Leu Leu Gly Thr Ala Leu Met Leu Val Gly
                340                 345                 350

GTT CTG GTG GCA GCT GCT TTC CTC TAC TGG TAC TGG ATT GAA GTT GTC     1152
Val Leu Val Ala Ala Ala Phe Leu Tyr Trp Tyr Trp Ile Glu Val Val
            355                 360                 365

CTG CTC TGT CGA ACC TAC AAG AAC AAA GAT GAG ACT CTG GGG GAT AAG     1200
Leu Leu Cys Arg Thr Tyr Lys Asn Lys Asp Glu Thr Leu Gly Asp Lys
        370                 375                 380

AAG GAA TTC GAT GCA TTT GTA TCC TAC TCG AAT TGG AGC TCT CCT GAG     1248
Lys Glu Phe Asp Ala Phe Val Ser Tyr Ser Asn Trp Ser Ser Pro Glu
    385                 390                 395

ACT GAC GCC GTG GGA TCT CTG AGT GAG GAA CAC CTG GCT CTG AAT CTT     1296
Thr Asp Ala Val Gly Ser Leu Ser Glu Glu His Leu Ala Leu Asn Leu
400                 405                 410                 415

TTC CCG GAA GTG CTA GAA GAC ACC TAT GGG TAC AGA TTG TGT TTG CTT     1344
Phe Pro Glu Val Leu Glu Asp Thr Tyr Gly Tyr Arg Leu Cys Leu Leu
                420                 425                 430

GAC CGA GAT GTG ACC CCA GGA GGA GTG TAT GCA GAT GAC ATT GTG AGC     1392
Asp Arg Asp Val Thr Pro Gly Gly Val Tyr Ala Asp Asp Ile Val Ser
            435                 440                 445

ATC ATT AAG AAA AGC CGA AGA GGA ATA TTT ATC CTG AGT CCC AGC TAC     1440
Ile Ile Lys Lys Ser Arg Arg Gly Ile Phe Ile Leu Ser Pro Ser Tyr
        450                 455                 460

CTC AAT GGA CCC CGT GTC TTT GAG CTA CAA GCA GCA GTG AAT CTT GCC     1488
Leu Asn Gly Pro Arg Val Phe Glu Leu Gln Ala Ala Val Asn Leu Ala
    465                 470                 475

TTG GTT GAT CAG ACA CTG AAG TTG ATT TTA ATT AAG TTC TGT TCC TTC     1536
Leu Val Asp Gln Thr Leu Lys Leu Ile Leu Ile Lys Phe Cys Ser Phe
480                 485                 490                 495
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
CAA GAG CCA GAA TCT CTT CCT TAC CTT GTC AAA AAG GCT CTG CGG GTT      1584
Gln Glu Pro Glu Ser Leu Pro Pyr Leu Val Lys Lys Ala Leu Arg Val
                500                 505                 510

CTC CCC ACA GTC ACA TGG AAA GGC TTG AAG TCG GTC CAC GCC AGT TCC      1632
Leu Pro Thr Val Thr Trp Lys Gly Leu Lys Ser Val His Ala Ser Ser
            515                 520                 525

AGG TTC TGG ACC CAA ATT CGT TAC CAC ATG CCT GTG AAG AAC TCC AAC      1680
Arg Phe Trp Thr Gln Ile Arg Tyr His Met Pro Val Lys Asn Ser Asn
        530                 535                 540

AGG TTT ATG TTC AAC GGG CTC AGA ATT TTC CTG AAG GGC TTT TCC CCT      1728
Arg Phe Met Phe Asn Gly Leu Arg Ile Phe Leu Lys Gly Phe Ser Pro
    545                 550                 555

GAA AAG GAC CTA GTG ACA CAG AAA CCC CTG GAA GGA ATG CCC AAG TCT      1776
Glu Lys Asp Leu Val Thr Gln Lys Pro Leu Glu Gly Met Pro Lys Ser
560                 565                 570                 575

GGG AAT GAC CAC GGA GCT CAG AAC CTC CTT CTC TAC AGT GAC CAG AAG      1824
Gly Asn Asp His Gly Ala Gln Asn Leu Leu Leu Tyr Ser Asp Gln Lys
                580                 585                 590

AGG TGC TGA                                                          1833
Arg Cys

Supplemental sequence of rodent, e.g., mouse, IL-1RD9 (SEQ
ID NO: 15 and 16).
TGACAGGAGC AAAGGGGAAC C ATG CTC TGT TTG GGC TGG GTG TTT CTT TGG        51
                         Met Leu Cys Leu Gly Trp Val Phe Leu Trp
                           1               5                  10

TTT GTT GCA GGA GAG AAG ACC ACA GGA TTT AAT CAT TCA GCT TGT GCC       99
Phe Val Ala Gly Glu Lys Thr Thr Gly Phe Asn His Ser Ala Cys Ala
                15                  20                  25

ACC AAA AAA CTT CTG TGG ACA TAT TCT GCA AGG GGT GCA GAG AAT TTT      147
Thr Lys Lys Leu Leu Trp Thr Tyr Ser Ala Arg Gly Ala Glu Asn Phe
            30                  35                  40

GTC CTA TTT TGT GAC TTA CAA GAG CTT CAG GAG CAA AAA TTC TCC CAT      195
Val Leu Phe Cys Asp Leu Gln Glu Leu Gln Glu Gln Lys Phe Ser His
        45                  50                  55

GCA AGT CAA CTG TCA CCA ACA CAA AGT CCT GCT CAC AAA CCT TGC AGT      243
Ala Ser Gln Leu Ser Pro Thr Gln Ser Pro Ala His Lys Pro Cys Ser
    60                  65                  70

GGC AGT CAG AAG GAC CTA TCT GAT GTC CAG TGG TAC ATG CAA CCT CGG      291
Gly Ser Gln Lys Asp Leu Ser Asp Val Gln Trp Tyr Met Gln Pro Arg
75                  80                  85                  90

AGT GGA AGT CCA CTA GAG GAG ATC AGT AGA AAC TCT CCC CAT ATG CAG      339
Ser Gly Ser Pro Leu Glu Glu Ile Ser Arg Asn Ser Pro His Met Gln
                95                 100                 105

AGT GAA GGC ATG CTG CAT ATA TTG GCC CCA CAG ACG AAC AGC ATT TGG      387
Ser Glu Gly Met Leu His Ile Leu Ala Pro Gln Thr Asn Ser Ile Trp
            110                 115                 120

TCA TAT ATT TGT AGA CCC AGA ATT AGG AGC CCC CAG GAT ATG GCC TGT      435
Ser Tyr Ile Cys Arg Pro Arg Ile Arg Ser Pro Gln Asp Met Ala Cys
        125                 130                 135

TGT ATC AAG ACA GTC TTA GAA GTT AAG CCT CAG AGA AAC GTG TCC TGT      483
Cys Ile Lys Thr Val Leu Glu Val Lys Pro Gln Arg Asn Val Ser Cys
    140                 145                 150

GGG AAC ACA GCA CAA GAT GAA CAA GTC CTA CTT CTT GGC AGT ACT GGC      531
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
Gly Asn Thr Ala Gln Asp Glu Gln Val Leu Leu Leu Gly Ser Thr Gly
155             160                 165                 170

TCC ATT CAT TGT CCC AGT CTC AGC TGC CAA AGT GAT GTA CAG AGT CCA      579
Ser Ile His Cys Pro Ser Leu Ser Cys Gln Ser Asp Val Gln Ser Pro
                175                 180                 185

GAG ATG ACC TGG TAC AAG GAT GGA AGA CTA CTT CCT GAG CAC AAG AAA      627
Glu Met Thr Trp Tyr Lys Asp Gly Arg Leu Leu Pro Glu His Lys Lys
            190                 195                 200

AAT CCA ATT GAG ATG GCA GAT ATT TAT GTT TTT AAT CAA GGC TTG TAT      675
Asn Pro Ile Glu Met Ala Asp Ile Tyr Val Phe Asn Gln Gly Leu Tyr
        205                 210                 215

GTA TGT GAT TAC ACA CAG TCA GAT AAT GTG AGT TCC TGG ACA GTC CGA      723
Val Cys Asp Tyr Thr Gln Ser Asp Asn Val Ser Ser Trp Thr Val Arg
    220                 225                 230

GCT GTG GTT AAA GTG AGA ACC ATT GGT AAG GAC ATC AAT GTG AAG CCG      771
Ala Val Val Lys Val Arg Thr Ile Gly Lys Asp Ile Asn Val Lys Pro
235                 240                 245                 250

GAA ATT CTG GAT CCC ATT ACA GAT ACA CTG GAC GTA GAG CTT GGA AAG      819
Glu Ile Leu Asp Pro Ile Thr Asp Thr Leu Asp Val Glu Leu Gly Lys
                255                 260                 265

CCT TTA ACT CTC CCC TGC AGA GTA CAG TTT GGC TTC CAA AGA CTT TCA      867
Pro Leu Thr Leu Pro Cys Arg Val Gln Phe Gly Phe Gln Arg Leu Ser
            270                 275                 280

AAG CCT GTG ATA AAG TGG TAT GTC AAA GAA TCT ACA CAG GAG TGG GAA      915
Lys Pro Val Ile Lys Trp Tyr Val Lys Glu Ser Thr Gln Glu Trp Glu
        285                 290                 295

ATG TCA GTA TTT GAG GAG AAA AGA ATT CAA TCC ACT TTC AAG AAT GAA      963
Met Ser Val Phe Glu Glu Lys Arg Ile Gln Ser Thr Phe Lys Asn Glu
    300                 305                 310

GTC ATT GAA CGT ACC ATC TTC TTG AGA GAA GTT ACC CAG AGA GAT CTC     1011
Val Ile Glu Arg Thr Ile Phe Leu Arg Glu Val Thr Gln Arg Asp Leu
315                 320                 325                 330

AGC AGA AAG TTT GTT TGC TTT GCC CAG AAC TCC ATT GGG AAC ACA ACA     1059
Ser Arg Lys Phe Val Cys Phe Ala Gln Asn Ser Ile Gly Asn Thr Thr
                335                 340                 345

CGG ACC ATA CGG CTC AGG AAG AAG GAA GAG GTG GTG TTT GTA TAC ATC     1107
Arg Thr Ile Arg Leu Arg Lys Lys Glu Glu Val Val Phe Val Tyr Ile
            350                 355                 360

CTT CTC GGC ACG GCC TTG ATG CTG GTG GGC GTT CTG GTG GCA GCT GCT     1155
Leu Leu Gly Thr Ala Leu Met Leu Val Gly Val Leu Val Ala Ala Ala
        365                 370                 375

TTC CTC TAC TGG TAC TGG ATT GAA GTT GTC CTG CTC TGT CGA ACC TAC     1203
Phe Leu Tyr Trp Tyr Trp Ile Glu Val Val Leu Leu Cys Arg Thr Tyr
    380                 385                 390

AAG AAC AAA GAT GAG ACT CTG GGG GAT AAG AAG GAA TTC GAT GCA TTT     1251
Lys Asn Lys Asp Glu Thr Leu Gly Asp Lys Lys Glu Phe Asp Ala Phe
395                 400                 405                 410

GTA TCC TAC TCG AAT TGG AGC TCT CCT GAG ACT GAC GCC GTG GGA TCT     1299
Val Ser Tyr Ser Asn Trp Ser Ser Pro Glu Thr Asp Ala Val Gly Ser
                415                 420                 425

CTG AGT GAG GAA CAC CTG GCT CTG AAT CTT TTC CCG GAA GTG CTA GAA     1347
Leu Ser Glu Glu His Leu Ala Leu Asn Leu Phe Pro Glu Val Leu Glu
            430                 435                 440
```

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

```
GAC ACC TAT GGG TAC AGA TTG TGT TTG CTT GAC CGA GAT GTG ACC CCA      1395
Asp Thr Tyr Gly Tyr Arg Leu Cys Leu Leu Asp Arg Asp Val Thr Pro
            445                 450                 455

GGA GGA GTG TAT GCA GAT GAC ATT GTG AGC ATC ATT AAG AAA AGC CGA      1443
Gly Gly Val Tyr Ala Asp Asp Ile Val Ser Ile Ile Lys Lys Ser Arg
        460                 465                 470

AGA GGA ATA TTT ATC CTG AGT CCC AGC TAC CTC AAT GGA CCC CGT GTC      1491
Arg Gly Ile Phe Ile Leu Ser Pro Ser Tyr Leu Asn Gly Pro Arg Val
475                 480                 485                 490

TTT GAG CTA CAA GCA GCA GTG AAT CTT GCC TTG GTT GAT CAG ACA CTG      1539
Phe Glu Leu Gln Ala Ala Val Asn Leu Ala Leu Val Asp Gln Thr Leu
                495                 500                 505

AAG TTG ATT TTA ATT AAG TTC TGT TCC TTC CAA GAG CCA GAA TCT CTT      1587
Lys Leu Ile Leu Ile Lys Phe Cys Ser Phe Gln Glu Pro Glu Ser Leu
            510                 515                 520

CCT TAC CTT GTC AAA AAG GCT CTG CGG GTT CTC CCC ACA GTC ACA TGG      1635
Pro Tyr Leu Val Lys Lys Ala Leu Arg Val Leu Pro Thr Val Thr Trp
        525                 530                 535

AAA GGC TTG AAG TCG GTC CAC GCC AGT TCC AGG TTC TGG ACC CAA ATT      1683
Lys Gly Leu Lys Ser Val His Ala Ser Ser Arg Phe Trp Thr Gln Ile
    540                 545                 550

CGT TAC CAC ATG CCT GTG AAG AAC TCC AAC AGG TTT ATG TTC AAC GGG      1731
Arg Tyr His Net Pro Val Lys Asn Ser Asn Arg Phe Met Phe Asn Gly
555                 560                 565                 570

CTC AGA ATT TTC CTG AAG GGC TTT TCC CCT GAA AAG GAC CTA GTG ACA      1779
Leu Arg Ile Phe Leu Lys Gly Phe Ser Pro Glu Lys Asp Leu Val Thr
                575                 580                 585

CAG AAA CCC CTG GAA GGA ATG CCC AAG TCT GGG AAT GAC CAC GGA GCT      1827
Gln Lys Pro Leu Glu Gly Met Pro Lys Ser Gly Asn Asp His Gly Ala
            590                 595                 600

CAG AAC CTC CTT CTC TAC AGT GAC CAG AAG AGG TGC TGATGGGTAG          1873
Gln Asn Leu Leu Leu Tyr Ser Asp Gln Lys Arg Cys
        605                 610

AACTTGCTGT GTGGATCAGG CTGATAGAAA TTGAGCCTTT CTGCTCTCAG TGCCAAGCAA    1933

GCTTGACAGG CAGTGGAATG AAGCGGCATC TGTGGTTTTA GGGTCTGGGT TCCTGGAACA    1993

GACACAGAGC AATACTCCAG ACCTCTGCCG TGTGCTTAGC ACACATTTCC CTGAGAGTTC    2053

CCAAGTAGCC TGAACAGAAT CAACAGAAAT AGCTCCATGG GCTGTCCAAC ATTCATGCAC    2113

GCATGCCTGT TTTGCACTAT ATATATGAAT TTATCATACG TTTGTGTGTG TATATGCATT    2173

CAGATAAATA GGATTTTATT TTGTTCGATA CGAGTGATTG AAACTCCATC TAAAGCCCTT    2233

CTGTAAAGAA AAAAAAAAA AAAAAA                                          2259
```

MLCLGWVFLWFVAGEKTTGFNHSACATKKLLWTYSARGAENFVLFCDLQELQEQKFSHASQLSPTQSPA

HKPCSGSQKDLSDVQWYMQPRSGSPLEEISRNSPHMQSEGMLHILAPQTNSIWSYICRPRIRSPQDMAC

CIKTVLEVKPQRNVSCGNTAQDEQVLLLGSTGSIHCPSLSCQSDVQSPEMTWYKDGRLLPEHKKNPIEM

ADIYVFNQGLYVCDYTQSDNVSSWTVRAVVKVRTIGKDINVKPEILDPITDTLDVELGKPLTLPCRVQF

GFQRLSKPVIKWYVKESTQEWEMSVFEEKRIQSTFKNEVIERTIFLREVTQRDLSRKFVCFAQNSIGNT

TRTIRLRKKEEWFVVYILLGTALMLVGVLAAAFLYYYWIEVVLLCRTYKNKDETLGDKKEFDAFVSYS

NWSSPETDAVGSLSEEHLALNLFPEVLEDTYGYRLCLLDRDVTPGGVYADDIVSIIKKSRRGIFILSPS

TABLE 2-continued

Nucleotide and amino acid sequences (see SEQ ID NO: 5 and 6) of primate, e.g., human, IL-1 receptor like embodiment DNAX designation 9 (IL-1RD9). Nucleotides 9, 459, 462, 469, and 474 are designated C, but may be A, C, G, or T. Nucleotide 246 is designated C, but may be C or G. Nucleotides 321, 336, 360, and 423 are designated C, but may be C or T. Nucleotide 426 is designated C, but may be A or C.

YLNGPRVFELQAAVNLALVDQTLKLILIKFCSFQEPESLPYLVKKALRVLPTVTWKGLKSVHASSRFWT

QIRYHMPVKNSNRFMFNGLRIFLKGFSPEKDLVTQKPLEGMPKSGNDHGAQNLLLYSDQKRC

TABLE 3

Nucleotide and amino acid sequences (see SEQ ID NO: 17 and 18) of primate, e.g., human, embodiment of IL-1RD10. Single sequence derived from human brain frontal cortex, epileptic; re-excision. Nucleotides 374, 383, 396, 403, 433, 458, 459, 483, and 515 are indicated as C, each may be A, C, G, or T.

```
C TGT GAA TTA AAA TAT GGA GGC TTT GTT GTG AGA AGA ACT ACT GAA          46
  Cys Glu Leu Lys Tyr Gly Gly Phe Val Val Arg Arg Thr Thr Glu
   1           5                  10                  15

TTA ACT GTT ACA GCC CCT CTG ACT GAT AAG CCA CCC AAG CTT TTG TAT        94
Leu Thr Val Thr Ala Pro Leu Thr Asp Lys Pro Pro Lys Leu Leu Tyr
                  20                  25                  30

CCT ATG GAA AGT AAA CTG ACA ATT CAG GAG ACC CAG CTG GGT GAC TCT       142
Pro Met Glu Ser Lys Leu Thr Ile Gln Glu Thr Gln Leu Gly Asp Ser
              35                  40                  45

GCT AAT CTA ACC TGC AGA GCT TTC TTT GGG TAC AGC GGA GAT GTC AGT       190
Ala Asn Leu Thr Cys Arg Ala Phe Phe Gly Tyr Ser Gly Asp Val Ser
          50                  55                  60

CCT TTA ATT TAC TGG ATG AAA GGA GAA AAA TTT ATT GAA GAT CTG GAT       238
Pro Leu Ile Tyr Trp Met Lys Gly Glu Lys Phe Ile Glu Asp Leu Asp
      65                  70                  75

GAA AAT CGA GTT TGG GAA AGT GAC ATT AGA ATT CTT AAG GAG CAT CTT       286
Glu Asn Arg Val Trp Glu Ser Asp Ile Arg Ile Leu Lys Glu His Leu
 80                  85                  90                  95

GGG GAA CAG GAA GTT TCC ATC TCA TTA ATT GTG GAC TCT GTG GAA GAA       334
Gly Glu Gln Glu Val Ser Ile Ser Leu Ile Val Asp Ser Val Glu Glu
                 100                 105                 110

GGT GAC TTG GGA AAT TAC TCC TGT TAT GTT GAA AAA TGG CAA TGG ACG       382
Gly Asp Leu Gly Asn Tyr Ser Cys Tyr Val Glu Lys Trp Gln Trp Thr
             115                 120                 125

CCG ACA CGC CAG CCG TCC CCC TTC ATA AAC GAG AGC CTA ATG TAC ACA       430
Pro Thr Arg Gin Pro Ser Pro Phe Ile Asn Glu Ser Leu Met Tyr Thr
         130                 135                 140

GTC GGA ACT TGC CTG GAG GCC CTT GGG CCA AAA CCT TGG TGG TTG AAT       478
Val Gly Thr Cys Leu Glu Ala Leu Gly Pro Lys Pro Trp Trp Leu Asn
     145                 150                 155

GTT TCG GGA CCA CCT TCA AAG TGT ACC AAG GTT GGA CC                    516
Val Ser Gly Pro Pro Ser Lys Cys Thr Lys Val Gly
160                 165                 170
```

CELKYGGFVVRRTTELTVTAPLTDKPPKLLYPMESKLTIQETQLGDSANLTCRAFFGYSGDVSPLIYWM

KGEKFIEDLDENRVWESDIRILKEHLGEQEVSISLIVDSVEEGDLGNYSCYVEKWXWTXTRQXSXFINE

SLMYTXGTCLEALGXKPWWLNVXGPPSKCTKVG

TABLE 3-continued

Supplemental sequence of primate, e.g., human, IL-1RD10
(SEQ ID NO: 19 and 20). Note nucleotides 1501, 1775, 1777,
1820, 1832, 1841, and 1844 are designated C;
each may be A, C, G, or T.

```
GAA TTC GGC ACG AGC TGT GAA TTA AAA TAT GGA GGC TTT GTT GTG AGA          48
Glu Phe Gly Thr Ser Cys Glu Leu Lys Tyr Gly Gly Phe Val Val Arg
  1               5                  10                  15

AGA ACT ACT GAA TTA ACT GTT ACA GCC CCT CTG ACT GAT AAG CCA CCC          96
Arg Thr Thr Glu Leu Thr Val Thr Ala Pro Leu Thr Asp Lys Pro Pro
             20                  25                  30

AAG CTT TTG TAT CCT ATG GAA AGT AAA CTG ACA ATT CAG GAG ACC CAG         144
Lys Leu Leu Tyr Pro Met Glu Ser Lys Leu Thr Ile Gln Glu Thr Gln
         35                  40                  45

CTG GGT GAC TCT GCT AAT CTA ACC TGC AGA GCT TTC TTT GGG TAC AGC         192
Leu Gly Asp Ser Ala Asn Leu Thr Cys Arg Ala Phe Phe Gly Tyr Ser
     50                  55                  60

GGA GAT GTC AGT CCT TTA ATT TAC TGG ATG AAA GGA GAA AAA TTT ATT         240
Gly Asp Val Ser Pro Leu Ile Tyr Trp Met Lys Gly Glu Lys Phe Ile
 65                  70                  75                  80

GAA GAT CTG GAT GAA AAT CGA GTT TGG GAA AGT GAC ATT AGA ATT CTT         288
Glu Asp Leu Asp Glu Asn Arg Val Trp Glu Ser Asp Ile Arg Ile Leu
                 85                  90                  95

AAG GAG CAT CTT GGG GAA CAG GAA GTT TCC ATC TCA TTA ATT GTG GAC         336
Lys Glu His Leu Gly Glu Gln Glu Val Ser Ile Ser Leu Ile Val Asp
             100                 105                 110

TCT GTG GAA GAA GGT GAC TTG GGA AAT TAC TCC TGT TAT GTT GAA AAT         384
Ser Val Glu Glu Gly Asp Leu Gly Asn Tyr Ser Cys Tyr Val Glu Asn
         115                 120                 125

GGA AAT GGA CGT CGA CAC GCC AGC GTT CTC CTT CAT AAA CGA GAG CTA         432
Gly Asn Gly Arg Arg His Ala Ser Val Leu Leu His Lys Arg Glu Leu
     130                 135                 140

ATG TAC ACA GTG GAA CTT GCT GGA GGC CTT GGT GCT ATA CTC TTG CTG         480
Met Tyr Thr Val Glu Leu Ala Gly Gly Leu Gly Ala Ile Leu Leu Leu
145                 150                 155                 160

CTT GTA TGT TTG GTG ACC ATC TAC AAG TGT TAC AAG ATA GAA ATC ATG         528
Leu Val Cys Leu Val Thr Ile Tyr Lys Cys Tyr Lys Ile Glu Ile Met
                 165                 170                 175

CTC TTC TAC AGG AAT CAT TTT GGA GCT GAA GAA CTC GAT GGA GAC AAT         576
Leu Phe Tyr Arg Asn His Phe Gly Ala Glu Glu Leu Asp Gly Asp Asn
             180                 185                 190

AAA GAT TAT GAT GCA TAC TTA TCA TAC ACC AAA GTG GAT CCT GAC CAG         624
Lys Asp Tyr Asp Ala Tyr Leu Ser Tyr Thr Lys Val Asp Pro Asp Gln
         195                 200                 205

TGG AAT CAA GAG ACT GGG GAA GAA GAA CGT TTT GCC CTT GAA ATC CTA         672
Trp Asn Gln Glu Thr Gly Glu Glu Glu Arg Phe Ala Leu Glu Ile Leu
     210                 215                 220

CCT GAT ATG CTT GAA AAG CAT TAT GGA TAT AAG TTG TTT ATA CCA GAT         720
Pro Asp Met Leu Glu Lys His Tyr Gly Tyr Lys Leu Phe Ile Pro Asp
225                 230                 235                 240

AGA GAT TTA ATC CCA ACT GGA ACA TAC ATT GAA GAT GTG GCA AGA TGT         768
Arg Asp Leu Ile Pro Thr Gly Thr Tyr Ile Glu Asp Val Ala Arg Cys
                 245                 250                 255

GTA GAT CAA AGC AAG CGG CTG ATT ATT GTC ATG ACC CCA AAT TAC GTA         816
Val Asp Gln Ser Lys Arg Leu Ile Ile Val Met Thr Pro Asn Tyr Val
             260                 265                 270

GTT AGA AGG GGC TGG AGC ATC TTT GAG CTG GAA ACC ACA CTT CTA AAT         864
Val Arg Arg Gly Trp Ser Ile Phe Glu Leu Glu Thr Thr Leu Leu Asn
         275                 280                 285

ATG CTT GTG ACT GGA GAA ATT AAA GTG ATT CTA ATT GAA TGC AGT GAA         912
```

TABLE 3-continued

```
Met Leu Val Thr Gly Glu Ile Lys Val Ile Leu Ile Glu Cys Ser Glu
    290                 295                 300

CTG AGA GGA ATT ATG AAC TAC CAC GAG GTG GAC GCC CTG AAG CAC ACC      960
Leu Arg Gly Ile Met Asn Tyr His Glu Val Asp Ala Leu Lys His Thr
305                 310                 315                 320

ATC AAG CTC CTG ACG GTC ATT AAA TGG CAT GGA CCA AAA TGC AAC AAG     1008
Ile Lys Leu Leu Thr Val Ile Lys Trp His Gly Pro Lys Cys Asn Lys
                325                 330                 335

TTG AAC TCC AAG TTC TGG AAA CGT TTA CAG TAT GAA ATG CCT TTT AAG     1056
Leu Asn Ser Lys Phe Trp Lys Arg Leu Gln Tyr Glu Met Pro Phe Lys
            340                 345                 350

AGG ATA GAA CCC ATT ACA CAT GAG CAG GCT TTA GAT GTC AGT CAG CAA     1104
Arg Ile Glu Pro Ile Thr His Glu Gln Ala Leu Asp Val Ser Gln Gln
        355                 360                 365

GGG CCT TTT GGG GAG CTG CAG ACT GTC TCG GCC ATT TCC ATG GCC GCG     1152
Gly Pro Phe Gly Glu Leu Gln Thr Val Ser Ala Ile Ser Met Ala Ala
    370                 375                 380

GCC ACC TCC ACA GCT CTA GCC ACT GCC CAT CCA GAT CTC CGT TGT ACC     1200
Ala Thr Ser Thr Ala Leu Ala Thr Ala His Pro Asp Leu Arg Cys Thr
385                 390                 395                 400

TTT CAC AAC ACG TAC CAT TCA CAA ATG CGT CAG AAA CAC TAC TAC CGA     1248
Phe His Asn Thr Tyr His Ser Gln Met Arg Gln Lys His Tyr Tyr Arg
                405                 410                 415

AGC TAT GAG TAC GAC GTA CCT CCT ACC GGC ACC CTG CCT CTT ACC TCC     1296
Ser Tyr Glu Tyr Asp Val Pro Pro Thr Gly Thr Leu Pro Leu Thr Ser
            420                 425                 430

ATA GGC AAT CAG CAT ACC TAC TGT AAC ATC CCT ATG ACA CTC ATC AAC     1344
Ile Gly Asn Gln His Thr Tyr Cys Asn Ile Pro Met Thr Leu Ile Asn
        435                 440                 445

GGG CAG CGG CCA CAG ACA AAA TCG AGC AGG GAG CAG AAT CCA GAT GAG     1392
Gly Gln Arg Pro Gln Thr Lys Ser Ser Arg Glu Gln Asn Pro Asp Glu
    450                 455                 460

GCC CAC ACA AAC AGT GCC ATC CTG CCG CTG TTG CCA AGG GAG ACC AGT     1440
Ala His Thr Asn Ser Ala Ile Leu Pro Leu Leu Pro Arg Glu Thr Ser
465                 470                 475                 480

ATA TCC AGT GTG ATA TGG TGACAGAAAA GCAAGGGACA TCCCGTCCCT            1488
Ile Ser Ser Val Ile Trp
                485

GGGAGGTTGA GTCGGAATCT GCAGTCCAGT GCCTGGAACT AAATCCTCGA CTGCTGCTGT   1548

TAAAAAACAT GCATTAGAAT CTTTAGAACA CGAGGAAAAA CAGGGTCTTG TACATATGTT   1608

TTTTGGAATT TCTTTGTAGC ATCAGTGTCC TCCTGTTTTA CCATGTCTTT TACCATTACA   1668

TTTTTTGACT TTGTTTTATA TGTCGTTGGA ATTTGTAAAT TTACATTTTT TTTAAAGAAG   1728

AGACTGATGT GTAGATAGAA AACCCTTTTT TTGCTTCATT AGTTTACGCT TTTAGAATGG   1788

GTTTTTATTT TATTTCCTTT TTTAAAATTT TCACTTTGCT TTTCAACATT TCCCTCTGGG   1848

GTGCTTGAAC AAATCTATCC GATGGGACAA GGAGCACCGG ATTCTTTCTC GGGTTCTGCC   1908

TAGCATCAAC TGGGCCACGT CGGCCTTCAG AGAACAGTGC AACAAATGCC AGCATTGCCA   1968

TTCGGGGGA AAAAAAAAAA AAAAAAAAAA CTCGAG                             2004
```

Supplemented sequence of primate IL-1RD10 (SEQ ID NO: 34 and 35):

```
GAT GGA TGC ACT GAC TGG TCT ATC GAT ATC AAG AAA TAT CAA GTT TTG       48
Asp Gly Cys Thr Asp Trp Ser Ile Asp Ile Lys Lys Tyr Gln Val Leu
1               5                   10                  15

GTG GGA GAG CCT GTT CGA ATC AAA TGT GCA CTC TTT TAT GGT TAT ATC       96
Val Gly Glu Pro Val Arg Ile Lys Cys Ala Leu Phe Tyr Gly Tyr Ile
            20                  25                  30
```

TABLE 3-continued

```
AGA ACA AAT TAC TCC CTT GCC CAA AGT GCT GGA CTC AGT TTG ATG TGG    144
Arg Thr Asn Tyr Ser Leu Ala Gln Ser Ala Gly Leu Ser Leu Met Trp
         35                  40                  45

TAC AAA AGT TCT GGT CCT GGA GAC TTT GAA GAG CCA ATA GCC TTT GAC    192
Tyr Lys Ser Ser Gly Pro Gly Asp Phe Glu Glu Pro Ile Ala Phe Asp
     50                  55                  60

GGA AGT AGA ATG AGC AAA GAA GAA GAC TCC ATT TGG TTC CGG CCA ACA    240
Gly Ser Arg Met Ser Lys Glu Glu Asp Ser Ile Trp Phe Arg Pro Thr
 65                  70                  75                  80

TTG CTA CAG GAC AGT GGT CTC TAC GCC TGT GTC ATC AGG AAC TCC ACT    288
Leu Leu Gln Asp Ser Gly Leu Tyr Ala Cys Val Ile Arg Asn Ser Thr
                 85                  90                  95

TAC TGT ATG AAA GTA TCC ATC TCA CTG ACA GTG GGT GAA AAT GAC ACT    336
Tyr Cys Met Lys Val Ser Ile Ser Leu Thr Val Gly Glu Asn Asp Thr
             100                 105                 110

GGA CTC TGC TAT AAT TCC AAG ATG AAG TAT TTT GAA AAA GCT GAA CTT    384
Gly Leu Cys Tyr Asn Ser Lys Met Lys Tyr Phe Glu Lys Ala Glu Leu
             115                 120                 125

AGC AAA AGC AAG GAA ATT TCA TGC CGT GAC ATA GAG GAT TTT CTA CTG    432
Ser Lys Ser Lys Glu Ile Ser Cys Arg Asp Ile Glu Asp Phe Leu Leu
    130                 135                 140

CCA ACC AGA GAA CCT GAA ATC CTT TGG TAC AAG GAA TGC AGG ACA AAA    480
Pro Thr Arg Glu Pro Glu Ile Leu Trp Tyr Lys Glu Cys Arg Thr Lys
145                 150                 155                 160

ACA TGG AGG CCA AGT ATT GTA TTC AAA AGA GAT ACT CTG CTT ATA AGA    528
Thr Trp Arg Pro Ser Ile Val Phe Lys Arg Asp Thr Leu Leu Ile Arg
                165                 170                 175

GAA GTC AGA GAA GAT GAC ATT GGA AAT TAT ACC TGT GAA TTA AAA TAT    576
Glu Val Arg Glu Asp Asp Ile Gly Asn Tyr Thr Cys Glu Leu Lys Tyr
            180                 185                 190

GGA GGC TTT GTT GTG AGA AGA ACT ACT GAA TTA ACT GTT ACA GCC CCT    624
Gly Gly Phe Val Val Arg Arg Thr Thr Glu Leu Thr Val Thr Ala Pro
            195                 200                 205

CTG ACT GAT AAG CCA CCC AAG CTT TTG TAT CCT ATG GAA AGT AAA CTG    672
Leu Thr Asp Lys Pro Pro Lys Leu Leu Tyr Pro Met Glu Ser Lys Leu
    210                 215                 220

ACA ATT CAG GAG ACC CAG CTG GGT GAC TCT GCT AAT CTA ACC TGC AGA    720
Thr Ile Gln Glu Thr Gln Leu Gly Asp Ser Ala Asn Leu Thr Cys Arg
225                 230                 235                 240

GCT TTC TTT GGG TAC AGC GGA GAT GTC AGT CCT TTA ATT TAC TGG ATG    768
Ala Phe Phe Gly Tyr Ser Gly Asp Val Ser Pro Leu Ile Tyr Trp Met
                245                 250                 255

AAA GGA GAA AAA TTT ATT GAA GAT CTG GAT GAA AAT CGA GTT TGG GAA    816
Lys Gly Glu Lys Phe Ile Glu Asp Leu Asp Glu Asn Arg Val Trp Glu
            260                 265                 270

AGT GAC ATT AGA ATT CTT AAG GAG CAT CTT GGG GAA CAG GAA GTT TCC    864
Ser Asp Ile Arg Ile Leu Lys Glu His Leu Gly Glu Gln Glu Val Ser
            275                 280                 285

ATC TCA TTA ATT GTG GAC TCT GTG GAA GAA GGT GAC TTG GGA AAT TAC    912
Ile Ser Leu Ile Val Asp Ser Val Glu Glu Gly Asp Leu Gly Asn Tyr
    290                 295                 300

TCC TGT TAT GTT GAA AAT GGA AAT GGA CGT CGA CAC GCC AGC GTT CTC    960
Ser Cys Tyr Val Glu Asn Gly Asn Gly Arg Arg His Ala Ser Val Leu
305                 310                 315                 320

CTT CAT AAA CGA GAG CTA ATG TAC ACA GTG GAA CTT GCT GGA GGC CTT    1008
Leu His Lys Arg Glu Leu Met Tyr Thr Val Glu Leu Ala Gly Gly Leu
                325                 330                 335

GGT GCT ATA CTC TTG CTG CTT GTA TGT TTG GTG ACC ATC TAC AAG TGT    1056
Gly Ala Ile Leu Leu Leu Leu Val Cys Leu Val Thr Ile Tyr Lys Cys
            340                 345                 350
```

TABLE 3-continued

```
TAC AAG ATA GAA ATC ATG CTC TTC TAC AGG AAT CAT TTT GGA GCT GAA    1104
Tyr Lys Ile Glu Ile Met Leu Phe Tyr Arg Asn His Phe Gly Ala Glu
        355                 360                 365

GAG CTC GAT GGA GAC AAT AAA GAT TAT GAT GCA TAC TTA TCA TAC ACC    1152
Glu Leu Asp Gly Asp Asn Lys Asp Tyr Asp Ala Tyr Leu Ser Tyr Thr
        370                 375                 380

AAA GTG GAT CCT GAC CAG TGG AAT CAA GAG ACT GGG GAA GAA GAA CGT    1200
Lys Val Asp Pro Asp Gln Trp Asn Gln Glu Thr Gly Glu Glu Glu Arg
385                 390                 395                 400

TTT GCC CTT GAA ATC CTA CCT GAT ATG CTT GAA AAG CAT TAT GGA TAT    1248
Phe Ala Leu Glu Ile Leu Pro Asp Met Leu Glu Lys His Tyr Gly Tyr
                405                 410                 415

AAG TTG TTT ATA CCA GAT AGA GAT TTA ATC CCA ACT GGA ACA TAC ATT    1296
Lys Leu Phe Ile Pro Asp Arg Asp Leu Ile Pro Thr Gly Thr Tyr Ile
        420                 425                 430

GAA GAT GTG GCA AGA TGT GTA GAT CAA AGC AAG CGG CTG ATT ATT GTC    1344
Glu Asp Val Ala Arg Cys Val Asp Gln Ser Lys Arg Leu Ile Ile Val
        435                 440                 445

ATG ACC CCA AAT TAC GTA GTT AGA AGG GGC TGG AGC ATC TTT GAG CTG    1392
Met Thr Pro Asn Tyr Val Val Arg Arg Gly Trp Ser Ile Phe Glu Leu
    450                 455                 460

GAA ACC AGA CTT CGA AAT ATG CTT GTG ACT GGA GAA ATT AAA GTG ATT    1440
Glu Thr Arg Leu Arg Asn Met Leu Val Thr Gly Glu Ile Lys Val Ile
465                 470                 475                 480

CTA ATT GAA TGC AGT GAA CTG AGA GGA ATT ATG AAC TAC CAG GAG GTG    1488
Leu Ile Glu Cys Ser Glu Leu Arg Gly Ile Met Asn Tyr Gln Glu Val
                485                 490                 495

GAG GCC CTG AAG CAC ACC ATC AAG CTC CTG ACG GTC ATT AAA TGG CAT    1536
Glu Ala Leu Lys His Thr Ile Lys Leu Leu Thr Val Ile Lys Trp His
        500                 505                 510

GGA CCA AAA TGC AAC AAG TTG AAC TCC AAG TTC TGG AAA CGT TTA CAG    1584
Gly Pro Lys Cys Asn Lys Leu Asn Ser Lys Phe Trp Lys Arg Leu Gln
        515                 520                 525

TAT GAA ATG CCT TTT AAG AGG ATA GAA CCC ATT ACA CAT GAG CAG GCT    1632
Tyr Glu Met Pro Phe Lys Arg Ile Glu Pro Ile Thr His Glu Gln Ala
        530                 535                 540

TTA GAT GTC AGT GAG CAA GGG CCT TTT GGG GAG CTG CAG ACT GTC TCG    1680
Leu Asp Val Ser Glu Gln Gly Pro Phe Gly Glu Leu Gln Thr Val Ser
545                 550                 555                 560

GCC ATT TCC ATG GCC GCG GCC ACC TCC ACA GCT CTA GCC ACT GCC CAT    1728
Ala Ile Ser Met Ala Ala Ala Thr Ser Thr Ala Leu Ala Thr Ala His
                565                 570                 575

CCA GAT CTC CGT TCT ACC TTT CAC AAC ACG TAC CAT TCA CAA ATG CGT    1776
Pro Asp Leu Arg Ser Thr Phe His Asn Thr Tyr His Ser Gln Met Arg
        580                 585                 590

CAG AAA CAC TAC TAC CGA AGC TAT GAG TAC GAC GTA CCT CCT ACC GGC    1824
Gln Lys His Tyr Tyr Arg Ser Tyr Glu Tyr Asp Val Pro Pro Thr Gly
        595                 600                 605

ACC CTG CCT CTT ACC TCC ATA GGC AAT CAG CAT ACC TAC TGT AAC ATC    1872
Thr Leu Pro Leu Thr Ser Ile Gly Asn Gln His Thr Tyr Cys Asn Ile
        610                 615                 620

CCT ATG ACA CTC ATC AAC GGG CAG CGG CCA CAG ACA AAA TCG AGC AGG    1920
Pro Met Thr Leu Ile Asn Gly Gln Arg Pro Gln Thr Lys Ser Ser Arg
625                 630                 635                 640

GAG CAG AAT CCA GAT GAG GCC CAC ACA AAC AGT GCC ATC CTG CCG CTG    1968
Glu Gln Asn Pro Asp Glu Ala His Thr Asn Ser Ala Ile Leu Pro Leu
                645                 650                 655

TTG CCA AGG GAG ACC AGT ATA TCC AGT GTG ATA TGG TGACAGAAAA         2014
Leu Pro Arg Glu Thr Ser Ile Ser Ser Val Ile Trp
```

TABLE 3-continued

|  | 660 | 665 |  |  |  |
|---|---|---|---|---|---|
| GCAAGGGACA | TCCCGTCCCT | GGGAGGTTGA | GTGGAATCTG | CAGTCCAGTG | CCTGGAACTA | 2074 |
| AATCCTCGAC | TGCTGCTGTT | AAAAAACATG | CATTAGAATC | TTTAGAACAC | GAGGAAAAAC | 2134 |
| AGGGTCTTGT | ACATATGTTT | TTTGGAATTT | CTTTGTAGCA | TCAGTGTCCT | CCTGTTTTAC | 2194 |
| CATGTCTTTT | ACCATTACAT | TTTTTGACTT | TGTTTTATAT | GTCGTTGGAA | TTTGTAAATT | 2254 |
| TACATTTTTT | TTAAAGAAGA | GACTGATGTG | TAGATAGAAA | ACCCTTTTTT | TGCTTCATTA | 2314 |
| GTTTAGTTTT | AGAATGGGTT | TTTATTTTAT | TTCCTTTTTT | AAAATTTTAC | TTTGCTTTTA | 2374 |
| ACATTTCCTT | GGGGTGCTTG | AACAAATCTA | TCCGATGGGA | CAAGGAGCAC | CGGATTCTTT | 2434 |
| CTCGGGTTCT | GCCTAGCATC | AACTGGGCCA | CGTCGGCCTT | CAGAGAACAG | TGCAACAAAT | 2494 |
| GCCAGCATTG | CCATTCGGGG | GGAAAAAAAA | AAAAAAAAAA | AAA |  | 2537 |

TABLE 4

Alignment of the extracellular domains of various IL-1RS.
hIL-1RD10 is SEQ ID NO: 20; hIL-1RD8 is SEQ ID NO: 3; mIL-1RD3
is GenBank x85999; hIL-1RD6 is GenBank u49065; mIL-1RD6 is
GenBank U49066; mIL-1RD4 is GenBank Y07519 and GenBank D13695;
hIL-1RD4 is GenBank D12763; hIL-1RD2 is GenBank x59770;
mIL-1RD2 is GenBank x59769; hIL-1RD5 is GenBank U43672;
mIL-1RD5 is GenBank U43673; mIL-1RD1 is GenBank M20658, M29752;
hIL-1RD1 is GenBank x16896; cIL-1RD1 is GenBank 86325; and
hFGR4 is GenBank P22455. Other species counterparts may be
obtained from public sequence databases.

```
mIL-1RD3   .......... ......MGLL WYLMSLSFYG ILQSHASERC DDWLDTMR..
hIL-1RD6   .......... .........M WSLLLCGLSI ALPLSVTADG CKDIFMKN..
rIL-1RD6   .......... .......MGM PPLLFCWVSF VLPLFVAAGN CTDVYMHH..
mIL-1RD4   .......... ........MI DRQRMGLWAL AILTLPMYLT VTEGSKSS..
hIL-1RD4   .......... .........MG FWILAILTIL MYSTAAKFSK QS........
hIL-1RD2   .......... ....MLRLYV LVMGVSAFTL QPAAHTGAAR SCRFRGRHYK
mIL-1RD2   MFILLVLVTG VSAFTTPTVV HTGKVSESPI TSEKPTVHGD NCQFRGREFK
hIL-1RD10  .......... .......... .......... .......... ..........
hIL-1RD5   .......... .....MNCRE LPLTLWVLIS VSTAESCTSR PHITVVE...
mIL-1RD5   .......... .....MHHEE LILTLCILIV KSASKSCIHR SQIHVVE...
mIL-1RD1   .......... .....MENMK VLLGLICLMV PLLSLEIDVC TEYPNQIVLF
hIL-1RD1   .......... ........MK VLLRLICFIA LLISSLEADK CKEREEKIIL
cIL-1RD1   .......... .....MHKMT STFLLIGHLI LLIPLFSAEE CVICNYFVLV
hIL-1RD8   .........M KPPFLLALVV CSVVSTNLKM VSKRNSVDGC IDWSVDLKTY
    hFGR4  ...MRLLLAL LGVLLSVPGP PVLSLEASEE VELEPCLAPS LEQQEQELTV mIL-1RD3   QIQVFEDEPA RIKCPLFEHF LKYNYSTAHS SGLTLLWYWT RQDRDLEEPI
hIL-1RD6   .EILSASQPF AFNCTFPPI. ........TS GEVSVTWYKN ....SSKIPV
rIL-1RD6   .EMISEGQPF PFNCTYPPV. ........TN GAVNLTWHRT ....PSKSPI
mIL-1RD4   ..WGLENEAL IVRCPQRG.. ..........R STYPVEWYYS ....DTNESI
hIL-1RD4   ..WGLENEAL IVRCPRQG.. ..........K PSYTVDWYYS ....QTNKSI
hIL-1RD2   REFRLGEPV  ALRCPQVPYW .......SVS PRINLTWHKN ....DSARTV
mIL-1RD2   SELRLEGEPV VLRCPLAPHS DIS.....SS SHSFLTWSKL ....DSSQLI
hIL-1RD10  .......... .......... .......... .......... ..........
hIL-1RD5   .....GEPFY LKHCSCSLAH ........EI ETTTKSWYKS ...SGSQEHV
mIL-1RD5   .....GEPFY LKPCGISAPV .......HRN ETATMRWFKG ...SASHEYR
mIL-1RD1   LSV...NEID IRKCPLTPN. ........KM HGDTIIWYKN ....DSKTPI
hIL-1RD1   VSS..ANEID VRPCPLNPN. ..........E HKGTITWYKD ....DSKTPV
cIL-1RD1   ......GEPT AISCPVITL. .......PMLH SDYNLTWYRN ....GSNMPI
hIL-1RD8   ..MALAGEPV RVKCALFYSY IRTNYSTAQS TGLRLMWYKN ..KGDLEEPI
    hFGR4  ....ALGQPV RLCCGRAERG G......... .....HWYKE ....GSRLAP mIL-1RD3   NFRLP.ENRI SKEDVLWFR  PTLLNDTGNY TCMLRNTTYC SKVAFPLEVV
hIL-1RD6   SKII..QSRI HQDETWILFL PMEWGDSGVY QCVIKGRDSC HRIHVNLTVF
rIL-1RD6   SINR..HVRI HQDQSWILFL PLALEDSGIY QCVIKDAHSC YRIAINLTVF
mIL-1RD4   PTQK..RNRI FVSRDRLKFL PARVEDSGIY ACVIRSPNLN KTGYLNVTIH
hIL-1RD4   PTQE..RNRV FASGQLLKFL PAEVADSGIY TCIVRSPTFN RTGYANVTIY
hIL-1RD2   PGEE..ETRM WAQDGALWLL PALQEDSGIY VCTTRNASYC DKMSIELRVF
mIL-1RD2   PRDEP...RM WVKGNILWIL PAVQQDSGTY ICTFRNASHC EQMSVELKVF
hIL-TRD10  .......... .......... .......... .......... ..........
hIL-1RDS   ELNPRSSSRI ALHDCVLEFW PVELNDTGSY FFQMKN..YT QKWKLNVIRR
mIL-1RD5   ELNNRSSPRV TFHDHTLEFW PVEMEDEGTY ISQVGN..DR RNWTLNVTKR
mIL-1RD1   SADR..DSRI HQQNEHLWFV PAKVEDSGYY YCIVRNSTYC LKTKVTVTVL
```

TABLE 4-continued

```
hIL-1RD1    STEQ..ASRI  HQHKEKLWFV  PAKVEDSGHY  YCVVRNSSYC  LRIKISAKFV
cIL-1RD1    TTER..RARI  HQRKGLLWFI  PAALEDSGLY  ECEVRSLNRS  KQKIINLKVF
hIL-1RD8    ......EVRM  SKEEDSIWFH  SAEAQDSGFY  TCVLRNSTYC  MKVSMSLTVA
   hFGR4    AG......RV  RGWRGRLEIA  SFLPEDAGRY  LCLARGSMIV  LQNLTLITGD mIL-1RD3    QK........  ..........  .......DSC  FNSAMRFPVH  KMYIEHGIHK
hIL-1RD6    EK........  ..........  .HWCDTSIGG  LP.NLSDEYK  QILHLGKDDS
rIL-1RD6    RK........  ..........  .HWCDSSNEE  SSINSSDEYQ  QWLPIGKSGS
mIL-1RD4    KK........  ..........  .....PPSCN  .IPDY.LMYS  TVRGSDKNFK
hIL-1RD4    KK........  ..........  .....QSDCN  .VPDY.LMYS  TVSGSEKNSK
hIL-1RD2    EN........  ..........  .......TDA  FLPFI..SYP  QILTLSTSGV
mIL-1RD2    KN........  ..........  .......TEA  SLPHV..SYL  QISALSTTGL
hIL-1RD10   ..........  ..........  ..........  ..........  ..........
hIL-1RD5    NK........  ..........  .......HSC  FTERQ..VTS  KIVEVKKFFQ
mIL-1RD5    NK........  ..........  .......HSC  FSDKL..VTS  RDVEVNKSLH
mIL-1RD1    EN........  ..........  .....DPGIC  .YSTQ.ATFP  QRLHIAGDGS
hIL-1RD1    EN........  ..........  .....EPNLC  .YNAQ.AIFK  QKLPVAGDGG
cIL-1RD1    KN........  ..........  .....DNGLC  .FNGE.MKYD  QIVKSANAGK
hIL-1RD8    EN........  ..........  .....ESGLC  .YNSR.IRYL  EKSEVTKRKE
   hFGR4    SLTSSNDDED  PKSHRDPSNR  HSYPQQAPYW  THPQRMEKKL  HAVPAGNTVK mIL-1RD3    ITCPNVDGYF  P.SSVKPSVT  WYKGCTEIVD  FHN...VLPE  GMNLSFFIPL
hIL-1RD6    LTCHLHFPKS  ...CVLGPIK  WYKDCNEIKG  E......RFT  VLETRLLVSN
rIL-1RD6    LTCHLYFPES  ...CVLDSIK  WYKGCEEIKV  S......KKFC  PTGTKLLVNN
mIL-1RD4    ITCPTIDLY.  ...NWTAPVQ  WFKNCKALQE  P......RFR  AHRSYLFIDN
hIL-1RD4    IYCPTIDLY.  ...NWTAPLE  WFKNCQALQG  S......RYR  AHKSFLVIDN
hIL-1RD2    LVCPDLSEFT  R.DKTDVKIQ  WYKDSLLLDK  DNEK..FLSV  RGTTHLLVHD
mIL-1RD2    LVCPDLKEFI  S.SNADGKIQ  WYKGAILLDK  GNKE..FLSA  GDPTRLLISN
hIL-1RD10   ..........  ..........  ..........  ..........  ..........
hIL-1RD5    ITCENSYYQ.  ...TLVNSTS  LYKNCKKLLL  ENN....KNP  TIKKNAEF..
mIL-1RD5    ITCKNPNYE.  ...ELIQDTW  LYKNCKEISK  TPRI...LKD  AEFGDAEF..
nIL-1RD1    LVCPYVSYFK  DENNELPEVQ  WYKNCKPLLL  DN.....VSFF  GVKDRLLVRN
hIL-1RD1    LVCPYMEFFK  NENNELPKLQ  WYKDCKPLLL  DN....IHFS  GVKDRLIVMN
cIL-1RD1    IICPDLENFK  DEDNINPEIH  WYKECKSGFL  EDKR..LVLA  EGENAILILN
hIL-1RD8    ISCPDMDDFK  KSD.QEPDVV  WYKECKPKMW  R.....SIII  QKGNALLIQE
   hFGR4    FRCPAAG...  ...NPTPTIR  WLKDGQAFHG  ENRIGGIRLR  HQHWSLVMES mIL-1RD3    VSNN..GNYT  CVVTYPENGR  LFHLTRTVTV  KVVGS.PKDA  LPPQIYSPND
hIL-1RD6    VSAEDRGNYA  CQAILTHSGK  QYEVLNGITV  SITERAGYGG  SVP.KIIYPK
rIL-1RDG    IDVEDSGSYA  CSARLTHLGR  IFTVRVYIAV  NTKE.VGSGG  RIP.NITYPK
mIL-1RD4    VTHDDEGDYT  CQFTHAENGT  NYIVTATRSF  TVE.EKGFS.  MFPVITNPPY
hIL-1RD4    VMTEDAGDYT  CKFIHNENGA  NYSVTATRSF  TVKDEQGFS.  LFPVIGAPAQ
hIL-1RD2    VALEDAGYYR  CVLTFAHEGQ  QYNITRSIEL  RIKKK..KEE  TIPVIISP..
mIL-1RD2    TSMDDAGYYR  CVMTFTYNGQ  EYNITRNIEL  RVKGT..TTE  PIPVIISP..
hIL-1RD10   ...EFG..TS  CEL..KYGGF  V..VRRTTEL  TVTAPLTDKP  PKLLYPMESK
hIL-1RD5    ...EDQGYYS  CVHFLHHNGK  LFNITKTFNI  TIVED..RSN  IVPVLLGP.K
mIL-1RD5    ...GDEGYYS  CVFSVHHNGT  RYNITKTVNI  TVIEG..RSK  VTPAILGP.K
mIL-1RD1    VAEEHRGDYI  CRMSYTFRGK  QYPVIRVIQF  ITIDE..NKR  DRPVILSP.R
hIL-1RD1    VAEKHRGNYT  CHASYTYLGK  QYPITRVIEF  ITLEE..NKP  TRPVIVSP.A
cIL-1RD1    VTIQDKGNYT  CRMVYTYMGK  QYNVSRTMNL  EVKES..PLK  MRPEFIYP.N
hIL-1RD8    VQEEDGGNYT  CEL..KYEGK  L..VRRTTEL  KVTALLTDKP  PKPLFPMENQ
   hFGR4    VVPSDRGTYT  CLVENAVGSI  RYNYLLDVLE  RSPH..RPIL  QAGLPANTT.

mIL-1RD3    RVVYEKEPGE  ELVIPCKVYF  SFIMD.SHNE  VWWTIDGKKP  .DDVTVDITI
hIL-1RD6    NHSIEVQLGT  TLIVDCNVTD  TK..D.NTNL  RCWRVNNTLV  DDYYDESKRI
rIL-1RD6    NNSIEVQLGS  TLIVDCNITD  TK..E.NTNL  RCWRVNNTLV  DDYYNDFKRI
mIL-1RD4    NHTMEVEIGK  PASIACSACF  GKGSH.FLAD  VLWQINKTVV  GNFGEARIQE
hIL-1RD4    NEIKEVEIGK  NANLTCSACF  GKGTQ.FLAA  VLWQLNGTKI  TDFGEPRIQQ
hIL-1RD2    LKTISASLGS  RLTIPCKVFL  GTGTP.LTTM  LWWTANDTHI  .ESAYPGGRV
mIL-1RD2    LETIPASLGS  RLIVPCKVFL  GTGTS.SNTI  VWWLANSTFI  .SAAYPRGRV
hIL-1RD10   LTIQETQLGD  SANLTCRAFF  GYSGD.VSPL  IYWMKGEKFI  EDLDENRVEW
hIL-1RD5    LNHVAVELGK  NVRLNCSALL  N.....EEDV  IYWMFGEENG  ...SDPNIHE
mIL-1RD5    CEKVGVELGK  DVELNCSASL  N.....KDDL  FYWSIRKEDS  ...SDPNVQE
mIL-1RD1    NETIEADPGS  MIQLICNVTG  Q.....FSDL  VYKWNGSEI  .EWNDPFLAE
hIL-1RD1    NETMEVDLGS  QIQLICNVTG  Q.....LSDI  AYWKWNGSVI  .DEDDPVLGE
cIL-1RD1    NNTIEVELGS  HVVMECNVSS  ......YGLL  PYWQVNDEDV  .DSFDSTYRE
hIL-1RD8    PSVIDVQLGK  PLNIPCKAFF  GFSGE.SGPM  IYWMKGEKFI  .EELAGHIRE
   hFGR4    ......AWGS  DVELLCKVYS  .....QPHIQ  ..WLKHIVIN  GSSFGA..DG mIL-1RD3    NESVSYSSTE  D..ETRTQIL  SIKKVTPEDL  RRNYVCHARN  TKGEAEQAAK
hIL-1RD6    REGVETHVSF  REHNLYTVNI  TFLEVKMEDY  GLPFMCHAG.  ...VSTAYII
rIL-1RD6    QEGIETNLSL  RNHILYTVNI  TFLEVKMEDY  GHPFTCHAA.  ...VSAAYII
mIL-1RD4    EEGRNESSSN  D.MDCLTSVL  RITGVTEKDL  SLEYDCLALN  LHGMIRHTIR
hIL-1RD4    EEGQNQSFSN  G.LACLDMVL  RIADVKEEDL  LLQYDCLALN  LHGLRRHTVR
hIL-1RD2    TEGPRQEYSE  NNENYIEVPL  IFDPVTREDL  HMDFKCVVHN  TLSFQTLRTT
mIL-1RD2    TEGLHHQYSE  NDENYVEVSL  IFDPVTREDL  HTDFKCVASN  PRSSQSLHTT
hIL-1RD10   SDIRILKEHL  G.EQEVSISL  IVDSVEEGDL  .GNYSCVYEN  GNGRRHASVL
hIL-1RDS    EKEMRIMTPE  G.KWHASKVL  RIENIGESNL  NVLYNCTVAS  TGGTDTKSFI
mIL-1RD5    DRKETTTWIS  EGKLHASKIL  RFQKITENYL  NVLYNCTVAN  EEAIDTKSFV
```

TABLE 4-continued

```
mIL-1RD1    DYQFVEHPST KRKYTLITTL NISEVKSQFY RYPFICVVKN TNIFESAHVQ
hIL-1RD1    DYYSVENPAN KRRSTLITVL NISEIESRFY KHPFTCFAKN THGIDAAYIQ
cIL-1RD1    QFYEEGMPHG ..IAVSGTKF NISEVKLKDY AYKFFCHFIY DSQEFTSYIK
hIL-1RD8    GEIRLLKEHL G.EKEVELAL IFDSVVEADL AN.YTCHVEN RNGRKHASVL
   hFGR4    FPYVQVLKTA DINSSEVEVL YLRNVSAED. AGEYTCLAGN SIGLSYQSAW mIL-1RD3    VKQKV....I PPRYTVELAC GFGATVFLVV VLIVVY
hIL-1RD6    LQLP.....A PDFRAYLIGG LIALVAVAVS VVYIYNIFKI DIVLWY
rIL-1RD6    LKRP.....A PDFRAYLIGG LMAFLLLAVS ILYIYNTFKV DIVLWY
mIL-1RD4    LRRK.....Q PSKECPSHIA IYYIVAGCSL LLMFINVLVI VL
hIL-1RD4    LSRK.....N PSKEC
hIL-1RD2    VKEASS.... .TFSWGIVLA PLSLAFLVLG GIWM
mIL-1RD2    VKEVSS.... .TFSWSIALA PLSLIILVVG AIW.
hIL-1RD10   LHKREL.... .MYTVELAGG LGAILLLLVC LVTIYKCY
hIL-1RD5    LVRKADMADI P..GHVFTRG MIIAVLILVA VVCLVTVCVI Y
mIL-1RD5    LVRKEIPDIP ...GHVFTGG VTVLVLASVA AVCIVILCVI Y
mIL-1RD1    LIYP.....V PDFKNYLIGG FIILTATIVC CVCIY
hIL-1RD1    LIYP.....V TNFQKHMIGI CVTLTVIIVC SVFIY
cIL-1RD1    LEHP.....V QNIRGYLIGG GISLIFLLFL ILIVY
hIL-1RD8    LRKKDL.... .IYKIELAGG LGAIFLLLVL LWIYKCY
   hFGR4    .........E EDPTWTAAAP EARYTDIILY ASGSLALAVL LLLAGLY
```

Alignment of the intracellular domains of various IL-1Rs.
hIL-1RD9 is SEQ ID NO: 8; mIL-1RD9 is SEQ ID NO: 14; hIL-
1RD1 is GenBank X16896; hIL-1RD6 is GenBank U49065;
mIL-1RD3 is GenBank X85999; huIL-1RD8 is SEQ ID NO: 3; and
mIL-1RD4 is GenBank Y07S19.

```
HuIL-1RD1   SDGKTYDAYI LYPKTVGEG. ..STSDCDIF VFKVLPEVLE KQCGYKLFIY
HuIL-1RD6   VDGKLYDAYV LYPKPHKES. ..QRHAVDAL VLNILPEVLE RQCGYKLFIF
MoIL-1RD3   LDGKEYDIYV SYAR...... ...NVEEEEF VLLTLRGVLE NEFGYKLCIF
HuIL-1RD8   DDNKEYDAYL SYTKVDQDTL DCDNPEEEQF ALEVLPDVLE KHYGYKLFIP
HuIL-1RD5   TDGKTYDAFV SYLKECRP.. ..ENGEEHTF AVEILPRVLE KHFGYKLCIF
MoIL-1RD9   .......... .......... .......... .......... ..........
HuIL-1RD9   .......... .......... .......... .......... .KYGYSLCLL
MoIL-1RD4   NDGKLYDAYI IYPRVFRGS. AAGTHSVEYF VHHTLPDVLE NKCGYKLCIY

HuIL-1RD1   GRDDYV.GED IVEVINENVK KSRRLIIILV RETSGFSWLG GSSEEQIAMY
HuIL-1RD6   GRDEFP.GQA VANVIDENVK LCRRLIVIVV PESLGFGLLK NLSEEQIAVY
MoIL-1RD3   DRDSLPGGIV TDETLS.FIQ KSRRLLVVLS PNYVLQG.TQ ALLELKAGLE
HuIL-1RD8   ERDLIPSG.T YMEDLTRYVE QSRRLIIVLT PDYILRR.GW SIFELESRLH
HuIL-1RDB   ERDVVPGGAV VDEIHS.LIE KSRRLIIVLS KSYMSN...E VRYELESGLH
MoIL-1RD9   DRDVTP.GGV YADDIVSIIK KSRRGIFILS PSYLNG...P RVFELQAAVN
HuIL-1RD9   ERDVAP.GGV YAEDIVSIIK RSRRGIFILS PNYVNG...P SIFELQAAVN
MoIL-1RD4   GRDLLP.GQD AATVVESSIQ NSRRQVFVLA PHMMHSK..E FAYEQEIALH

HuIL-1RD1   NALVQDGIKV VLLELEKIQ. .....DYEKM PESIKFIKQK HGAIRWSGDF
HuIL-1RD6   SALIQDGMKV ILIELEKIE. .....DYTVM PESIQYIKQK HGAIRWHGDF
MoIL-1RD3   NMASRGNINV ILVQYKAVK. ...DMKVKEL KRAKTVLT.. ..VIKWKGEK
HuIL-1RD8   NMLVSGEIKV ILIECTELKG KVNCQEVESL KRSIKLLS.. ..LIKWKGSK
HuIL-1RD5   EALVERKIKI ILIEFTPVT. .....DFTFL PQSLKLLKSH R.VLKWKADK
MoIL-1RD9   LALVDQTLKL ILIKFCSFQ. .....EPESL PYLVKKALRV LPTVTWKGLK
HuIL-1RD9   LALDDQTLKL ILIKFCYFQ. .....EPESL PHLVKKALRV LPTVTWRGLK
MoIL-1RD4   SALIQNNSKV ILIEMEPLG. EASRLQVGDL QDSLQHLVKI QGTIKWREDH

HuIL-1RD1   TQGPQSAKTR FWKNVRYHMP VQRRSPSSKH
HuIL-1RD6   TEQSQCMKTK FWKTVRYHMP PRRCRPFLRS
MoIL-1RD3   SKYPQ...GR FWKQLQVAMP VKKSPRWSSN
HuIL-1RD8   SSKLN...SK FWKHLVYEMP IKKKEMLPRC
HuIL-1RD5   ........SR FWKNLLYLMP AKTVKPGRDE
MoIL-1RD9   ........SR FWTQIRYHMP VKNSNRFMFN
HuIL-1RD9   SVPPN...SR FWAKMRYHMP VKNSQGFTWN
MoIL-1Rp4   VADKQSLSSK FWKHVRYQMP VPERASKTAS
```

Alignment of primate IL-1RD8, primate IL-1RD10, and primate and
rodent IL-1RD3 which are all beta type subunits

```
hRD8       MKPPFLLALVVCSVVSTNLKMVSKRNSVDGCIDWSVD-LKTYMALAGEPV
hRD10      --------------------------DGCTDWSID-IKKYQVLVGEPV
hRD3       ------MTLLWC-VVSLYFYGILQSDASERCDDWGLDTMRQIQVFEDEPA
mRD3       ------MGLLWY-LMSLSFYGILQSHASERCDDWGLDTMRQIQVFEDEPA
                         : * **.:* ::   .: .**.

hRD8       RVKCALFYSYIRTNYSTAQSTGLRLMWYKNKG--DLEEPIIFS--EVRMS
hRD10      RIKCALFYGYIRTNYSLAQSAGLSLMWYKSSGPGDFEEPIAFD--GSRMS
hRD3       RIKCPLFEHFLKFNYSTAHSAGLTLIWYWTRQDRDLEEPINFRLPENRIS
mRD3       RIKCPLFEHFLKYNYSTAHSSGLTLIWYWTRQDRDLEEPINFRLPENRIS
           *:.  ::: *** *:*:** *:**  .   *:**** *   *:*
```

TABLE 4-continued

```
hRD8    KEEDSIWFHSAEAQDSGFYTCVLRNSTYCMKVSMSLTVAENESGLCYNSR
hRD10   KEEDSIWFRPTLLQDSGLYACVIRNSTYCMKVSISLTVGENDTGLCYNSK
hRD3    KEKDVLWFRPTLLNDTGNYTCMLRNTTYCSKVAFPLEVVQKDS--CFNSP
mRD3    KEKDVLWFRPTLLNDTGNYTCMLRNTTYCSKVAFPLEVVQKDS--CFNSA
        **:* :**:.:   :*:* *:*:::* **::.*  * ::::  *:**

hRD8    IRY-LEKSEVTK-RKEISCPDMDDFKKSDQEPDVVWYKECKPKNWRSIII
hRD10   MKY-FEKAELSK-SKEISCRDIEDFLLPTREPEILWYKECRTKTWRPSIV
hRD3    MKLPVHKLYIEYGIQRITCPNVDGYFPSSVKPTITWYMGCYKIQNFNNVI
mRD3    MRFPVHKMYIEHGIHKITCPNVDGYFPSSVKPSVTWYKGCTEIVDFHNVL
        ::  ..*  :    :.*:* :::.: .  :* : **  *          ::

hRD8    QKGN--ALLIQEVQEEDGGNYTCELKY--EGKLVRRTTELKVTALLTDK-
hRD10   FKRD--TLLIREVREDDIGNYTCELKY--GGFVVRRTTELTVTAPLTDK-
hRD3    PEGMNLSFLIALISNN--GNYTCVVTYPENGRTFHLTRTLTVKVVGSPKN
mRD3    PEGMNLSFFIPLVSNN--GNYTCVVTYPENGRLFHLTRTVTVKVVGSPKD
         :    :::* : :: ***** ..*   *  ..: * :.*..  : * hRD8    --PPKPLFPMENQPSVIDVQLGKPLNIPCKAFFGFSGESGPMIYWMGKEK
hRD10   --PPKLLYPMESKLTIQETQLGDSANLTCRAFFGYSGDVSPLIYWMGKEK
hRD3    AVPPPVIHSPNDH--VVYEKEPGEELLIPCTVYFSFLMDSRNEVWWTIDGK
mRD3    ALPPPQIYSPNDR--VVYEKEPGEELVIPCKVYFSFIMDSHNEVWWTIDGK
          **    *  :    :  :   *.  :.* .:*.:  :    ::*  . * hRD8    FIEEL-AGHIREGEIRLLKEHLGEKEVELALIFDSVVEADLA-NYTCHVE
hRD10   FIEDLDDENRVWESDIRILKEHLGEQEVSISLIVDSVEEGDLG-NYSCYVE
hRD3    KPDDI-TIDVTINESISHSRTEDETRTQI-LSIKKVTSEDLKRSYVCHAR
mRD3    KPDDV-TVDITINESVSYSSTEDETRTQI-LSIKKVTPEDLRRNYVCHAR
         :::     :   .:      .*  ...:  *  ...*  **  .*  *:..

hRD8    NRNGR--KHASVLLRKKDLIYKIELAGGLGAIFLLLVLLVVIYKCYNIEL
hRD10   NGNGR--RHASVLLHKRELMYTVELAGGLGAILLLLVCLVTIYKCYKIEI
hRD3    SAKGEVAKAAKVKQKVPAPRYTVELACGFGATVLLVVILIVVYHVYWLEM
mRD3    NTKGEAEQAAKVKQKVIPPRYTVELACGFGATVFLVVVLIVVYHVYWLEM
        . :*.  :  *.*  :      *.:*** *:** .:*:* *:.:*: *  :*:

hRD8    MLFYRQHFGADETNDDNKEYDAYLSYTKVDQDTLDCDNPEEEQFALEVLP
hRD10   MLFYRNHFGAEELDGDNKDYDAYLSYTKVDDPDQWNQETGEEERFALEILP
hRD3    VLFYRAHFGTDETILDGKEYDIYVSYAR---------NAEEEEFVLLTLR
mRD3    VLFYRAHFGTDETILDGKEYDIYVSYAR---------NVEEEEFVLLTLR
        :** *::*  *.*:** *:::         . *.*.*   * hRD8    DVLEKHYGYKLFIPERDLIPSGTYMEDLTRYVEQSRRLIIVLTPDYILRR
hRD10   DMLEKHYGYKLFIPDRDLIPTGTYIEDVARCVDQSKRLIIVMTPNVVVRR
hRD3    GVLENEFGYKLCIFDRDSLPGGIVTDETLSFIQKSRRLVVLSPNYVLQG
mRD3    GVLENEFGYKLCIFDRDSLPGGIVTDETLSFIQKSRRLVVLSPNYVLQG
        .::.:** * :** :* *   ::     :::*:**:*:*:*:::

hRD8    GWSIFELESRLHNMLVSGEIKVILIECTELKGKVNCQEVESLKRSIKLLS
hRD10   GWSIFELETRLRNMLVTGEIKVILIECSELRGIMNYQEVEALKHTIKLLT
hRD3    TQALLELKAGLENMASRGNINVILVQYKAVK----ETKVKELKRAKTVLT
mRD3    TQALLELKAGLENMASRGNINVILVQYKAVK----DMKVKELKRAKTVLT
        :::*****:: *.**   *:*:*****::  . ::     :*: ** :: .:*:

hRD8    LIKWKGSKSSKLNSKFWKHLVYEMPIKKKEMLPRCHVLDSAEQGL-FGEL
hRD10   VIKWHGPKCNKLNSKFWKRLQYEMPFKRIEPITHEQALDVSEQGP-FGEL
hRD3    VIKWKGEKSKYPQGRFWKQLQVAMPVKKS---PRRSSSD--EQGLSYSSL
mRD3    VIKWKGEKSKYPQGRFWKQLQVAMPVKKS---PRWSSND--KQGLSYSSL
        :****:* *..  :.:***:*    **.*:    .:   *  :** :..* hRD8    QPIPSIAMTS-TSATLVSSQADLP-EFHPS--DSMQIRHCCRGYKHEIPA
hRD10   QTVSAISMAAATSTALATAHPDLRSTFHNTYHSQMRQKHYYRSYEYDVPP
hRD3    KNV-----------------------------------------------
mRD3    KNV-----------------------------------------------
        : :

hRD8    T-TLPVPSLGNHHTYCNLPLTLLNGQLPLNNTLKDT--QEFHRNSSLLPL
hRD10   TGTLPLTSIGNQHTYCNIPMTLINGQRPQTKSSREQNPDEAHTNSAILPL
hRD3    --------------------------------------------------
mRD3    -------------------------------------------------- hRD8    SSKELSFTSDIW
hRD10   LPRETSISSVIW
hRD3    ------------
mRD3    ------------

Alignment and comparison of primate and rodent IL-1RD9.
hIL-1RD9    MLCLGWIFLWLVAGERIKGFNISGCSTKKLLWTYSTRSEEEFVLFCDLPE
mIL-1RD9    MLCLGWVFLWFVAGEKTTGFNHSACATKKLLWTYSARGAENFVLFCDLQE
```

TABLE 4-continued

```
     ****.* **.  * * *.**********.* * ******* * hIL-1RD9  PQKSHFCHRNRLSPKQVPEHLPFMGSN-DLSDVQWYQQPSNGDPLEDIRK
mIL-RD9   LQEQKFSHASQLSPTQSPAHKPCSGSQKDLSDVQWYMQPRSGSPLEEISR
          *  .*.*  .*** * * * . ****   * ***.* .

hIL-1RD9  SYPHIIQDKCTLHFLTPGVNNSGSYICRPKMIKSPYDVACCVKMILEVKP
mIL-1RD9  NSPHMQSE-GMLHILAPQTNSIWSYICRPR-IRSPQDMACCIKTVLEVKP
           . .    *.*  *   ******. *.** *.***.* .***** hIL-1RD9  QTNASCEYSASHKQDLLLGSTGSISCPSLSCQSDAQSPAVTWYKNGKLLS
mIL-1RD9  QRNVSCGNTAQDEQVLLLGSTGSIHCPSLSCQSDVQSPEMTWYKDGRLLP
          * * **  .*  * ******* ***** * .**** *.**

hIL-1RD9  VERSNRIVVDEVYDYHQGTYVCDYTQSDTVSSWTVVAVVQVRTIVGDTKL
mIL-1RD9  EHKKNPIEMADIYVFNQGLYVCDYTQSDNVSSWTVRAVVKVRTIGKDINV
           . *  *  ...*  .. ******.******.**  *  .

hIL-1RD9  KPDILDPVEDTLEVELGKPLTISCKARFGFERVFNPVIKWYIKDSDLEWE
mIL-1RD9  KPEILDPITDTLDVELGKPLTLPCRVQFGFQRLSKPVIKWYVKESTQEWE
          .. *.********. *. .***.*.  ******.*.* *** hIL-1RD9  VSVPEAKSIKSTLKDEIIERNIILEKVTQRDLRRKFVCFVQNSIGNTTQS
mIL-1RD9  MSVFEEKRIQSTFKNEVIERTIFLREVTQRDLSRKFVCFAQNSIGNTTRT
          .** * * *.**  * *.***.* *  **** ** ******..

hIL-1RD9  VQLKEKRGVVLLYILLGTIGTLVAVLAASALLYRHWIEIVLLYRTYQSKD
mIL-1RD9  IRLRKKEEVVFVYILLGTALMLVGVLVAAAFLYYYWIEVVLLCRTYKNKD
          ..*. *   .**   ** *.*  *.*.*. **

hIL-1RD9  QTLGDKKDFDAFVSYAKWSSFPSEATSSLSEEHLALSLFPDVLENKYGYS
mIL-1RD9  ETLGDKKEFDAFVSYSNWSSPETDAVGSLSEEHLALNLFPEVLEDTYGYR
          .****.***. *   ..* ******* *.* * hIL-1RD9  LCLLERDVAPGGVYAEDIVSIIKRSRRGIFILSPNVVNGPSIFELQAAVN
mIL-1RD9  LCLLDRDVTPGGVYADDIVSIIKKSRRGIFILSPSYLNGPRVFELQAAVN
          **.*.****.**.******** *.* .****** hIL-1RD9  LALDDQTLKLILIKFCYFQEPESLPHLVKKALRVLPTVTWRGLKSVPPNS
mIL-1RD9  LALVDQTLKLILIKFCSFQEPESLPYLVKKALRVLPTVTWKGLKSVHASS
          * ******** **** ********* ***   * hIL-1RD9  RFWAKMRYHMPVKNSQGFTWNQLRITSRIFQ-------WKGLSRTETTGR
mIL-1RD9  RFWTQIRYHMPVKNSNRFMFNGLRIFLKGFSPEKDLVTQKPLEGMPKSGN
          *...******. * * ***  . *         * *    .* hIL-1RD9  ----------SSQPKEW
mIL-1RD9  DHGAQNLLLYSDQKRC
                    * * .
```

Structural analysis of the primate IL-1RD10 sequence (SEQ ID NO: 18, 20, and 35), in comparison with other IL-1Rs, shows characteristic features exist, which are conserved with the IL-1RD10 embodiment described herein. For example, there are characteristic Ig domains, and subdomains therein. The corresponding regions of the IL-1RD10 (SEQ ID NO: 18 and 20) are about: f2 to gly7; g2 from val10 to thr23; a3 from leu3O to met33; a3' from thr38 to gln40; b3 from ala48 to ala54; c3 from pro64 to lys70; c3' from glu72 to phe74; d3 from val83 to lys92; e3 from gln98 to val106; and f3 from tyrl117 to trp26.

Structural analysis of the rodent IL-1RD9 sequence (SEQ ID NO: 12, 14, and 16), in comparison with other IL-1Rs, shows characteristic features exist (see Table 4). For example, there are characteristic Ig domains, and subdomains therein. The corresponding regions of the IL-1RD9 (SEQ ID NO: 12, 14, and 16) are about: Ig1 domain from gly18 to pro127, with cys105 probably linked to cys52 (or possibly cys48); Ig2 domain from gly128 to pro229, with cys153 probably linked to cys199; and the Ig3 domain from glu230 to lys333, with cys251 probably linked to cys315; transmembrane segment from val336 to tyr360; THD domain from gly381 to val539; conserved trp residues probably correspond to residues 64, 169, and 267. Alignment of the IL-1RD9 embodiments is shown in Table 4. There are characteristic beta strand sections, and alpha helical structures, as described above for IL-1RD10. The corresponding segments of the human IL-1RD9 sequence (SEQ ID NO: 6, 8, and 10) are roughly: βB from gly3 to val13; α2 from pro15 to lys28; βc from ser30 to ser46; α3 from ile47 to gln61; βD from lys64 to glu75; α4 from glu77 to leu87;. βE from va193 to leu98; and α5 from arg106 to val117. The corresponding segments of the mouse IL-1RD9 sequence (SEQ ID NO: 12, 14, and 16) are roughly: α3 to gln10; βD from lys13 to glu24; α4 from glu26 to leu36; βE from va42 to leu47; and α5 from arg55 to val66.

As used herein, the terms IL-1 like receptor D8 (IL-1RD8), IL-1 like receptor D9 (IL-1RD9), or IL-1 like receptor D10 (IL-1RD10) shall be used to describe a polypeptide comprising a segment having or sharing the amino acid sequence shown in Tables 1, 2, or 3, or a substantial fragment thereof. The invention also includes a polypeptide variation of the respective IL-1RD8, IL-1RD9, IL-1RD10 alleles whose sequences are provided, e.g., a mutein or soluble extracellular or intracellular construct. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic, of the polypeptide described. Typically, it will bind to its corresponding biological ligand, perhaps in a dimerized state with an alpha receptor subunit, with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

This invention also encompasses polypeptides having substantial amino acid sequence identity with the amino acid sequences in Tables 1–3, preferably having segments of contiguous amino acid residues identical to segments of SEQ ID NO: 4, 10, or 35. It will include sequence variants with relatively few substitutions, e.g., typically less than about 25, ordinarily less than about 15, preferably less than about 3–5. Other embodiments include forms in association with an alpha subunit, e.g., an IL-1RD4, IL-1RD5, or IL-1RD6.

A substantial polypeptide "fragment", or "segment", is a stretch of amino acid residues of at least about 8 contiguous amino acids, generally at least 10 contiguous amino acids, more generally at least 12 contiguous amino acids, often at least 14 contiguous amino acids, more often at least 16 contiguous amino acids, typically at least 18 contiguous amino acids, more typically at least 20 contiguous amino acids, usually at least 22 contiguous amino acids, more usually at least 24 contiguous amino acids, preferably at least 26 contiguous amino acids, more preferably at least 28 contiguous amino acids, and, in particularly preferred embodiments, at least about 30 or more contiguous amino acids, usually 40, 50, 70, 90, 110, etc. Sequences of segments of different polypeptides can be compared to one another over appropriate length stretches. In many cases, the matching will involve a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12. Similar features apply to segments of nucleic acid.

Amino acid sequence homology, or sequence identity, is determined by optimizing residue matches, if necessary, by introducing gaps as required. See, e.g., Needleham, et al. (1970) *J. Mol. Biol.* 48:443–453; Sankoff, et al. (1983) chapter one in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous polypeptides will have from 50–100% homology (if gaps can be introduced), to 60–100% homology (if conservative substitutions are included) with an amino acid sequence segment of Table 1, 2, or 3. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous polypeptides, such as the allelic variants, will share most biological activities with the embodiments described in Table 1, 2, or 3.

As used herein, the term "biological activity" is used to describe, without limitation, effects on inflammatory responses, innate immunity, and/or morphogenic development by respective ligands. For example, these receptors should, like IL-1 receptors, mediate phosphatase or phosphorylase activities, which activities are easily measured by standard procedures. See, e.g., Hardie, et al. (eds. 1995) *The Protein Kinase FactBook* vols. I and II, Academic Press, San Diego, Calif.; Hanks, et al. (1991) *Meth. Enzymol.* 200:38–62; Hunter, et al. (1992) *Cell* 70:375–388; Lewin (1990) *Cell* 61:743–752; Pines, et al. (1991) *Cold Spring Harbor Symp. Quant. Biol.* 56:449–463; and Parker, et al. (1993) *Nature* 363:736–738. Other activities include antigenic or immunogenic functions. The receptors exhibit biological activities much like regulatable enzymes, regulated by ligand binding. However, the enzyme turnover number is more close to an enzyme than a receptor complex. Moreover, the numbers of occupied receptors necessary to induce such enzymatic activity is less than most receptor systems, and may number closer to dozens per cell, in contrast to most receptors which will trigger at numbers in the thousands per cell. The receptors, or portions thereof, may be useful as phosphate labeling enzymes to label general or specific substrates.

The terms ligand, agonist, antagonist, and analog of, e.g., an IL-1RD8, IL-1RD9, or IL-1RD10, include molecules that modulate the characteristic cellular responses to IL-1 ligand proteins, as well as molecules possessing the more standard structural binding competition features of ligand-receptor interactions, e.g., where the receptor is a natural receptor or an antibody. The cellular responses likely are mediated through binding of various IL-1 ligands to cellular receptors related to, but possibly distinct from, the type I or type II IL-1 receptors. See, e.g., Belvin and Anderson (1996) *Ann. Rev. Cell Dev. Biol.* 12:393–416; Morisato and Anderson (1995) *Ann. Rev. Genetics* 29:371–3991 and Hultmark (1994) *Nature* 367:116–117.

Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds. 1990) *Goodman & Gilman's: The Pharmacological Bases of Therapeutics*, Pergamon Press, New York.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

II. Activities

The IL-1 receptor-like polypeptides will have a number of different biological activities, e.g., in phosphate metabolism, being added to or removed from specific substrates, typically proteins. Such will generally result in modulation of an inflammatory function, other innate immunity response, or a morphological effect. For example, a human IL-1RD9 gene coding sequence probably has about 60–80% identity with the nucleotide coding sequence of mouse IL-1RD9. At the amino acid level, there is also likely to be reasonable identity.

The receptors will also exhibit immunogenic activity, e.g., in being capable of eliciting a selective immune response. Antiserum or antibodies resulting therefrom will exhibit both selectivity and affinity of binding. The polypeptides will also be antigenic, in binding antibodies raised thereto, in the native state, or in denatured.

The biological activities of the IL-1RDs will generally be related to addition or removal of phosphate moieties to substrates, typically in a specific manner, but occasionally in a non specific manner. Substrates may be identified, or conditions for enzymatic activity may be assayed by standard methods, e.g., as described in Hardie, et al. (eds. 1995) *The Protein Kinase FactBook* vols. I and II, Academic Press, San Diego, Calif.; Hanks, et al. (1991) *Meth. Enzymol.* 200:38–62; Hunter, et al. (1992) *Cell* 70:375–388; Lewin (1990) *Cell* 61:743–752; Pines, et al. (1991) *Cold Spring Harbor Symp. Quant. Biol.* 56:449–463; and Parker, et al. (1993) *Nature* 363:736–738.

III. Nucleic Acids

This invention contemplates use of isolated nucleic acid or fragments, e.g., which encode these or closely related proteins, or fragments thereof, e.g., to encode a corresponding polypeptide, preferably one which is biologically active. In addition, this invention covers isolated or recombinant DNA which encodes such polypeptides or polypeptides having characteristic sequences of the respective IL-1RDs, individually or as a group. Typically, the nucleic acid is capable of hybridizing, under appropriate conditions, with a nucleic acid coding sequence segment shown in Table 1, 2, or 3 but preferably not with a corresponding segment of other receptors. Said biologically active polypeptide can be a full length polypeptide, or fragment, and will typically have a segment of amino acid sequence highly homologous to one shown in Table 1, 2, or 3. Further, this invention covers the use of isolated or recombinant nucleic acid, or fragments thereof, which encode polypeptides having fragments which are equivalent to the IL-1RD9 proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is typically defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, for example, products made by transforming cells with an unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode equivalent polypeptides to fragments of, e.g, IL-1RD9, and fusions of sequences from various different related molecules, e.g., other IL-1 receptor family members.

A "fragment" in a nucleic acid context is a contiguous segment of at least about 17 contiguous nucleotides, generally at least 21 contiguous nucleotides, more generally at least 25 contiguous nucleotides, ordinarily at least 30 contiguous nucleotides, more ordinarily at least 35 contiguous nucleotides, often at least 39 contiguous nucleotides, more often at least 45 contiguous nucleotides, typically at least 50 contiguous nucleotides, more typically at least 55 contiguous nucleotides, usually at least 60 contiguous nucleotides, more usually at least 66 contiguous nucleotides, preferably at least 72 contiguous nucleotides, more preferably at least 79 contiguous nucleotides, and in particularly preferred embodiments will be at least 85 or more contiguous nucleotides, e.g., 100, 120, 140, etc. Typically, fragments of different genetic sequences can be compared to one another over appropriate length stretches, particularly defined segments such as the domains described below.

A nucleic acid which codes for an IL-1RD8, IL-1RD9, or IL-1RD10 will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous, or highly identical, nucleic acid sequences, when compared to one another, e.g., IL-1RD9 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from Table 1, 2, or 3. Typically, selective hybridization will occur when there is at least about 55% homology over a stretch of at least about 14 nucleotides, more typically at least about 65%, preferably at least about 75%, and more preferably at least about 90%. See, Kanehisa (1984) Nuc. Acids Res. 12:203–213, which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is much more important than the measure of any single parameter. See, e.g., Wetmur and Davidson (1968) J. Mol. Biol. 31:349–370, which is hereby incorporated herein by reference. The signal should be at least 2×over background, generally at least 5–10×over background, and preferably even more.

For sequence comparison, typically one sequence acts as a reference sequence, to which test sequences are compared. When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Nat'l Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) J. Mol. Evol. 35:351–360. The method used is similar to the method described by Higgins and Sharp (1989) CABIOS 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) J. Mol. Biol. 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules hybridize to each other under stringent conditions, as described below.

The isolated DNA can be readily modified by nucleotide substitutions, nucleotide deletions, nucleotide insertions, and inversions of nucleotide stretches. These modifications result in novel DNA sequences which encode this polypeptide or its derivatives. These modified sequences can be used to produce mutant proteins (muteins) or to enhance the expression of variant species. Enhanced expression may involve gene amplification, increased transcription, increased translation, and other mechanisms. Such mutant IL-1RD9-like derivatives include predetermined or site-specific mutations of the polypeptide or its fragments, including silent mutations using genetic code degeneracy. "Mutant IL-1RD9" as used herein encompasses a polypeptide otherwise falling within the homology definition of the IL-lR9 as set forth above, but having an amino acid sequence which differs from that of other IL-1RD-like polypeptides as found in nature, whether by way of deletion, substitution, or insertion. In particular, "site specific mutant IL-1RD9" encompasses a polypeptide having substantial homology with a polypeptide of Table 2, and typically shares most of the biological activities or effects of the forms disclosed herein.

Although site specific mutation sites are predetermined, mutants need not be site specific. Mammalian IL-1RD9 mutagenesis can be achieved by making amino acid insertions or deletions in the gene, coupled with expression. Substitutions, deletions, insertions, or many combinations may be generated to arrive at a final construct. Insertions include amino- or carboxy-terminal fusions. Random mutagenesis can be conducted at a target codon and the expressed mammalian IL-1RD9 mutants can then be screened for the desired activity, providing some aspect of a structure-activity relationship. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (1995; eds.) *PCR Primer: A Laboratory Manual* Cold Spring Harbor Press, CSH, N.Y. Appropriate primers of length, e.g., 15, 20, 25, or longer can be made using sequence provided.

IV. Proteins, Peptides

As described above, the present invention encompasses primate IL-1RD8, primate or rodent IL-1RD9, and primate IL-1RD10, e.g., whose sequences are disclosed, e.g., in Tables 1–3, and described herein. Descriptions of features of IL-1RD9 are applicable in most cases, with appropriate modifications, also to IL-1RD8 and/or to IL-1RD10. Allelic and other variants are also contemplated, including, e.g., fusion proteins combining portions of such sequences with others, including epitope tags and functional domains. Particularly interesting constructs will be intact extracellular or intracellular domains.

The present invention also provides recombinant polypeptides, e.g., heterologous fusion proteins using segments from these rodent proteins. A heterologous fusion protein is a fusion of proteins or segments which are naturally not normally fused in the same manner. Thus, the fusion product of, e.g., an IL-1RD9 with another IL-1 receptor is a continuous protein molecule having sequences fused in a typical polypeptide linkage, typically made as a single translation product and exhibiting properties, e.g., sequence or antigenicity, derived from each source peptide. A similar concept applies to heterologous nucleic acid sequences.

In addition, new constructs may be made from combining similar functional or structural domains from other related proteins, e.g., IL-1 receptors or Toll-like receptors, including species variants. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of this or related proteins. The resulting protein will often have hybrid function and properties. For example, a fusion protein may include a targeting domain which may serve to provide sequestering of the fusion protein to a particular subcellular organelle.

Candidate fusion partners and sequences can be selected from various sequence data bases, e.g., GenBank, c/o NCBI, and BCG, University of Wisconsin Biotechnology Computing Group, Madison, Wis., which are each incorporated herein by reference.

The present invention particularly provides muteins which bind IL-1-like ligands, and/or which are affected in signal transduction. Structural alignment of human IL-1RD9 with other members of the IL-1R family show conserved features/residues. See Table 4. Alignment of the human IL-1RD9 sequence with other members of the IL-1R family indicates various structural and functionally shared features. See also, Bazan, et al. (1996) *Nature* 379:591; Lodi, et al. (1994) *Science* 263:1762–1766; Sayle and Milner-White (1995) *TIBS* 20:374–376; and Gronenberg, et al. (1991) *Protein Engineering* 4:263–269.

The IL-1α and IL-1β ligands bind an IL-1 receptor type I (IL-1RD1) as the primary receptor and this complex then forms a high affinity receptor complex with the IL-1 receptor type III (IL-1RD3). Such receptor subunits are probably shared with the receptors for the new IL-1 ligand family members. See, e.g., U.S. Ser. No. 60/044,165 and U.S. Ser. No. 60/055,111. It is likely that the IL-1γ ligand signals through a receptor comprising the association of IL-1RD9 (alpha component) with IL-1RD5 (beta component). The IL-1δ and IL-1ε ligands each probably signal through a receptor comprising the association of one of IL-1RD4, IL-1RD6, or IL-1RD9 (alpha components) with one of IL-1RD3, IL-1RD5, IL-1RD7, IL-1RD8, or IL-1RD10 (beta components).

Similar variations in other species counterparts of IL-1R sequences, e.g., receptors D1–D6, D8, D9, or D10, in the corresponding regions, should provide similar interactions with ligand or substrate. Substitutions with either rodent or primate, e.g., mouse sequences or human sequences, are particularly preferred. Conversely, conservative substitutions away from the ligand binding interaction regions will probably preserve most signaling activities; and conservative substitutions away from the intracellular domains will probably preserve most ligand binding properties.

"Derivatives" of the primate or mouse IL-1RD9 include amino acid sequence mutants, glycosylation variants, metabolic derivatives and covalent or aggregative conjugates with other chemical moieties. Covalent derivatives can be prepared by linkage of functionalities to groups which are found in the IL-1RD9 amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the receptors or fragments thereof with other polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the receptors and other homologous or heterologous proteins are also provided. Homologous polypeptides may be fusions between different receptors, resulting in, for instance, a hybrid protein exhibiting binding specificity for multiple different IL-1 ligands, or a receptor which may have broadened or weakened specificity of substrate effect. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), Vols. 1–3, Cold Spring Harbor Laboratory, and Ausubel, et al. (eds. 1987 and periodic supplements) *Current Protocols in Molecular Biology,* Greene/Wiley, New York, which are each incorporated herein by reference. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach,* IRL Press, Oxford; each of which is incorporated herein by reference. See also Dawson, et al. (1994) *Science* 266:776–779 for methods to make larger polypeptides.

This invention also contemplates the use of derivatives of an IL-1RD8, IL-1RD9, or IL-1RD10 other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of a receptor or other binding molecule, e.g., an antibody. For example, an IL-1 ligand can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of an IL-1 receptor, antibodies, or other similar molecules. The ligand can also be labeled with a detectable group, e.g., radioiodinated by the chloramine T procedure, covalently bound to rare earth chelates, or conjugated to another fluorescent moiety for use in diagnostic assays.

An IL-1RD8, IL-1RD9, or IL-1RD10 of this invention can be used as an immunogen for the production of antisera or antibodies specific, e.g., capable of distinguishing between other IL-1 receptor family members, for the IL-1RD8, IL-1RD9, or IL-1RD10 or various fragments thereof. The purified IL-1RD8, IL-1RD9, or IL-1RD10 can be used to screen monoclonal antibodies or antigen-binding fragments prepared by immunization with various forms of impure preparations containing the protein. In particular, the term "antibodies" also encompasses antigen binding fragments of natural antibodies, e.g., Fab, Fab2, Fv, etc. The purified IL-1RD9 can also be used as a reagent to detect antibodies generated in response to the presence of elevated levels of expression, or immunological disorders which lead to antibody production to the endogenous receptor. Additionally, IL-1RD8, IL-1RD9, or IL-1RD10 fragments may also serve as immunogens to produce the antibodies of the present invention, as described immediately below. For example, this invention contemplates antibodies having binding affinity to or being raised against the amino acid sequences shown, e.g., in Tables 1, 2, or 3, fragments thereof, or various homologous peptides. In particular, this invention contemplates antibodies having binding affinity to, or having been raised against, specific fragments which are predicted to be, or actually are, exposed at the exterior polypeptide surface of the native IL-1RD8, IL-1RD9, or IL-1RD10. Various preparations of desired selectivity in binding can be prepared by appropriate cross absorptions, etc.

The blocking of physiological response to the receptor ligands may result from the inhibition of binding of the ligand to the receptor, likely through competitive inhibition. Thus, in vitro assays of the present invention will often use antibodies or antigen binding segments of these antibodies, or fragments attached to solid phase substrates. These assays will also allow for the diagnostic determination of the effects of either ligand binding region mutations and modifications, or other mutations and modifications, e.g., which affect signaling or enzymatic function.

This invention also contemplates the use of competitive drug screening assays, e.g., where neutralizing antibodies to the receptor or fragments compete with a test compound for binding to a ligand or other antibody. In this manner, the neutralizing antibodies or fragments can be used to detect the presence of a polypeptide which shares one or more binding sites to a receptor and can also be used to occupy binding sites on a receptor that might otherwise bind a ligand.

V. Making Nucleic Acids and Protein

DNA which encodes the polypeptides or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Tables 1–3. Other species counterparts can be identified by hybridization techniques, or by various PCR techniques, combined with or by searching in sequence databases, e.g., GenBank.

This DNA can be expressed in a wide variety of host cells for the synthesis of a full-length receptor or fragments which can in turn, e.g., be used to generate polyclonal or monoclonal antibodies; for binding studies; for construction and expression of modified ligand binding or kinase/phosphatase domains; and for structure/function studies. Variants or fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a polypeptide in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the polypeptide or its fragments in various hosts using vectors that do not contain a replication origin that is recognized by the host cell. It is also possible to use vectors that cause integration of the polypeptide encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual,* Elsevier, N.Y., and Rodriquez, et al. (eds. 1988) *Vectors: A Survey of Molecular Cloning Vectors and Their Uses,* Buttersworth, Boston, which are incorporated herein by reference.

Transformed cells are cells, preferably mammalian, that have been transformed or transfected with receptor vectors constructed using recombinant DNA techniques. Transformed host cells usually express the desired polypeptide or its fragments, but for purposes of cloning, amplifying, and manipulating its DNA, do not need to express the subject protein. This invention further contemplates culturing transformed cells in a nutrient medium, thus permitting the receptor to accumulate in the cell membrane. The polypeptide can be recovered, either from the culture or, in certain instances, from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis.* Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses,* (eds. Rodriguez and Denhardt), Buttersworth, Boston, Chapter 10, pp. 205–236, which is incorporated herein by reference.

Lower eukaryotes, e.g., yeasts and Dictvostelium, may be transformed with IL-1RD9 sequence containing vectors. For purposes of this invention, the most common lower eukaryotic host is the baker's yeast, *Saccharomyces cerevisiae.* It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, many higher eukaryotic tissue culture cell lines are workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo PolyA, see Thomas, et al. (1987) *Cell* 51:503–512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683–4690 and Nielsen, et al. (1997) *Protein Eng.* 10:1–12, and the precise amino acid composition of the signal peptide often does not appear to be critical to its function, e.g., Randall, et al. (1989) *Science* 243:1156–1159; Kaiser, et al. (1987) *Science* 235:312–317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells.

The source of IL-1RD8, IL-1RD9, or IL-1RD10 can be a eukaryotic or prokaryotic host expressing recombinant IL-1RD8, IL-1RD9, or IL-1RD10 such as is described above. The source can also be a cell line such as mouse Swiss 3T3 fibroblasts, but other mammalian cell lines are also contemplated by this invention, with the preferred cell line being from the human species.

Now that the sequences are known, the primate IL-lRs, fragments, or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Prac-* tice of Peptide Synthesis, Springer-Verlag, New York; and Bodanszky (1984) The Principles of Peptide Synthesis, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with partial IL-1RD9 sequences.

The IL-1RD8, IL-1RD9, or IL-1RD10 proteins, polypeptides, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in J. Am. Chem. Soc. 85:2149–2156, which is incorporated herein by reference.

The prepared protein and fragments thereof can be isolated and purified from the reaction mixture by means of peptide separation, e.g., by extraction, precipitation, electrophoresis, various forms of chromatography, and the like. The receptors of this invention can be obtained in varying degrees of purity depending upon desired uses. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the receptor, or lysates or supernatants of cells producing the polypeptide as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%–99% or more. Purity will usually be on a weight basis, but can also be on a molar basis. Different assays will be applied as appropriate. Similar concepts apply to polynucleotides and antibodies.

VI. Antibodies

Antibodies can be raised to the various mammalian IL-1RD8, IL-1RD9, or IL-1RD10 described herein, e.g., primate IL-1RD9 polypeptides and fragments thereof, both in naturally occurring native forms and in their recombinant forms, the difference being that antibodies to the active receptor are more likely to recognize epitopes which are only present in the native conformations. Denatured antigen detection can also be useful in, e.g., Western analysis. Anti-idiotypic antibodies are also contemplated, which would be useful as agonists or antagonists of a natural receptor or an antibody.

Antibodies, including binding fragments and single chain versions, against predetermined fragments of the polypeptide can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to the receptor and inhibit binding to ligand or inhibit the ability of the receptor to elicit a biological response, e.g., act on its substrate. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they might bind to the receptor without inhibiting ligand or substrate binding. As neutralizing antibodies, they can be useful in competitive binding assays. They will also be useful in detecting or quantifying ligand. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian IL-1Rs and fragments may be fused or covalently linked to a variety of immunogens, such as keyhole limpet hemocyanin, bovine serum albumin, tetanus toxoid, etc. See Microbiology, Hoeber Medical Division, Harper and Row, 1969; Landsteiner (1962) Specificity of Serological Reactions, Dover Publications, New York; and Williams, et al. (1967) Methods in Immunology and Immunochemistry, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunologoy (4th ed.), Lange Medical Publications, Los Altos, Calif., and references cited therein; Harlow and Lane (1988) Antibodies: A Laboratory Manual, CSH Press; Goding (1986) Monoclonal Antibodies: Principles and Practice (2d ed.)

Academic Press, New York; and particularly in Kohler and Milstein (1975) in *Nature* 256:495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant or chimeric immunoglobulins may be produced, see Cabilly, U.S. Pat. No. 4,816,567; or made in transgenic mice, see Mendez, et al. (1997) *Nature Genetics* 15:146–156. These references are incorporated herein by reference.

The antibodies of this invention can also be used for affinity chromatography in isolating the IL-1Rs. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified protein will be released. The protein may be used to purify antibody.

The antibodies may also be used to screen expression libraries for particular expression products. Usually the antibodies used in such a procedure will be labeled with a moiety allowing easy detection of presence of antigen by antibody binding.

Antibodies raised against an IL-1R will also be used to raise anti-idiotypic antibodies. These will be useful in detecting or diagnosing various immunological conditions related to expression of the protein or cells which express the protein. They also will be useful as agonists or antagonists of the ligand, which may be competitive inhibitors or substitutes for naturally occurring ligands.

An IL-1R polypeptide that specifically binds to or that is specifically immunoreactive with an antibody generated against a defined immunogen, such as an immunogen consisting of the amino acid sequence of, e.g., SEQ ID NO: 4, 10, or 35, is typically determined in an immunoassay. The immunoassay typically uses a polyclonal antiserum which was raised, e.g., to a polypeptide of SEQ ID NO: 4, 10, or 35. This antiserum is selected to have low crossreactivity against other IL-1R family members, e.g., IL-1Rs D1 through D8, preferably from the same species, and any such crossreactivity is removed by immunoabsorption prior to use in the immunoassay.

To produce antisera for use in an immunoassay, the polypeptide of, e.g., SEQ ID NO: 4, 10, or 35, is isolated as described herein. For example, recombinant polypeptide may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier polypeptide can be used an immunogen. Polyclonal sera are collected and titered against the immunogen polypeptide in an immunoassay, e.g., a solid phase immunoassay with the immunogen immobilized on a solid support. Polyclonal antisera with a titer of $10^4$ or greater are selected and tested for their cross reactivity against other IL-1R family members, e.g., IL-1RD1 through IL-1RD6, using a competitive binding immunoassay such as the one described in Harlow and Lane, supra, at pages 570–573. Preferably at least two IL-1R family members are used in this determination. These IL-1R family members can be produced as recombinant polypeptides and isolated using standard molecular biology and protein chemistry techniques as described herein.

Immunoassays in the competitive binding format can be used for the crossreactivity determinations. For example, the polypeptide of SEQ ID NO: 4, 10, or 35 can be immobilized to a solid support. Polypeptides added to the assay compete with the binding of the antisera to the immobilized antigen. The ability of the above polypeptides to compete with the binding of the antisera to the immobilized polypeptide is compared to the polypeptides of IL-1RD1 through IL-1RD6. The percent crossreactivity for the above polypeptides is calculated, using standard calculations. Those antisera with less than 10% crossreactivity with each of the polypeptides listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second polypeptide to the immunogen polypeptide (e.g., the IL-1RD8, IL-1RD9, or IL-1RD10 like polypeptide of SEQ ID NO: 4, 10, or 35). To make this comparison, the two polypeptides are each assayed at a wide range of concentrations and the amount of each polypeptide required to inhibit 50% of the binding of the antisera to the immobilized polypeptide is determined. If the amount of the second polypeptide required is less than twice the amount of the polypeptide of the selected polypeptide or polypeptides that is required, then the second polypeptide is said to specifically bind to an antibody generated to the immunogen.

It is understood that these IL-1R polypeptides are members of a family of homologous polypeptides that comprise at least 7 genes previously identified. For a particular gene product, such as, e.g., IL-1RD9, the term refers not only to the amino acid sequences disclosed herein, but also to other polypeptides that are allelic, non-allelic, or species variants. It is also understood that the terms include nonnatural mutations introduced by deliberate mutation using conventional recombinant technology such as single site mutation, or by excising short sections of DNA encoding the respective proteins, or by substituting new amino acids, or adding new amino acids. Such minor alterations typically will substantially maintain the immunoidentity of the original molecule and/or its biological activity. Thus, these alterations include polypeptides that are specifically immunoreactive with a designated naturally occurring IL-1RD8, IL-1RD9, or IL-1RD10 protein. The biological properties of the altered polypeptides can be determined by expressing the polypeptide in an appropriate cell line and measuring the appropriate effect, e.g., upon transfected lymphocytes. Particular polypeptide modifications considered minor would include conservative substitution of amino acids with similar chemical properties, as described above for the IL-1R family as a whole. By aligning a polypeptide optimally with the polypeptide of the IL-1Rs and by using the conventional immunoassays described herein to determine immunoidentity, one can determine the polypeptide compositions of the invention.

VII. Kits and Quantitation

Both naturally occurring and recombinant forms of the IL-1R like molecules of this invention are particularly useful in kits and assay methods. For example, these methods would also be applied to screening for binding activity, e.g., ligands for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767–773, which is incorporated herein by reference. The latter describes means for testing binding by a plurality of defined polymers synthesized on a solid substrate. The development of suitable assays to screen for a ligand or agonist/antagonist homologous polypeptides can be greatly facilitated by the availability of large amounts of purified, soluble IL-1Rs in an active state such as is provided by this invention.

Purified IL-1RD8, IL-1RD9, or IL-1RD10 can be coated directly onto plates for use in the aforementioned ligand screening techniques. However, non-neutralizing antibodies to these polypeptides can be used as capture antibodies to immobilize the respective receptor on the solid phase, useful, e.g., in diagnostic uses.

This invention also contemplates use of IL-1RD8, IL-1RD9, or IL-1RD10 fragments thereof, peptides, and their fusion products in a variety of diagnostic kits and methods for detecting the presence of the protein or its ligand. Alternatively, or additionally, antibodies against the molecules may be incorporated into the kits and methods. Typically the kit will have a compartment containing, e.g., either an IL-1RD9 peptide or gene segment or a reagent which recognizes one or the other. Typically, recognition reagents, in the case of peptide, would be a ligand or antibody, or in the case of a gene segment, would usually be a hybridization probe.

A preferred kit for determining the concentration of IL-1RD8, IL-1RD9, or IL-1RD10 in a sample would typically comprise a labeled compound, e.g., ligand or antibody, having known binding affinity for IL-1RD9, a source of IL-1RD9 (naturally occurring or recombinant) as a positive control, and a means for separating the bound from free labeled compound, for example a solid phase for immobilizing the IL-1RD9 in the test sample. Compartments containing reagents, and instructions, will normally be provided.

Antibodies, including antigen binding fragments, specific for mammalian IL-1RD8 or a peptide fragment, or receptor fragments are useful in diagnostic applications to detect the presence of elevated levels of ligand and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to an IL-1R or to a particular fragment thereof. These assays have also been extensively discussed in the literature. See, e.g., Harlow and Lane (1988) *Antibodies: A Laboratory Manual,* CSH., and Coligan (ed. 1991) and periodic supplements, *Current Protocols In Immunology* Greene/Wiley, New York.

Anti-idiotypic antibodies may have similar use to serve as agonists or antagonists of IL-1Rs. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. In many of these assays, a test compound, IL-1R, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The IL-1R can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion polypeptides will also find use in these applications.

Another diagnostic aspect of this invention involves use of oligonucleotide or polynucleotide sequences taken from the sequence of an IL-1R. These sequences can be used as probes for detecting levels of the respective IL-1R in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly 32p. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

VIII. Therapeutic Utility

This invention provides reagents with significant therapeutic value. The IL-1Rs (naturally occurring or recombinant), fragments thereof, mutein receptors, and antibodies, along with compounds identified as having binding affinity to the receptors or antibodies, should be useful in the treatment of conditions exhibiting abnormal expression of the receptors of their ligands. Such abnormality will typically be manifested by immunological disorders. Additionally, this invention should provide therapeutic value in various diseases or disorders associated with abnormal expression or abnormal triggering of response to the ligand. The IL-1 ligands have been suggested to be involved in morphologic development, e.g., dorso-ventral polarity determination, and immune responses, particularly the primitive innate responses. See, e.g., Sun, et al. (1991) *Eur. J. Biochem.* 196:247–254; Hultmark (1994) *Nature* 367:116–117.

Recombinant IL-1Rs, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Ligand screening using IL-1R or fragments thereof can be performed to identify molecules having binding affinity to the receptors. Subsequent biological assays can then be utilized to determine if a putative ligand can provide competitive binding, which can block intrinsic stimulating activity. Receptor fragments can be used as a blocker or antagonist in that it blocks the activity of ligand. Likewise, a compound having intrinsic stimulating activity can activate the receptor and is thus an agonist in that it simulates the activity of ligand, e.g., inducing signaling. This invention further contemplates the therapeutic use of antibodies to IL-1Rs as antagonists.

The quantities of reagents necessary for effective therapy will depend upon many different factors, including means of administration, target site, reagent physiological life, pharmacological life, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Because of the likely high affinity binding, or turnover numbers, between a putative ligand and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

IL-1Rs, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. However, combinations of the compositions of the inventions with each other and with other compositions or reagents are also contemplated and encompassed by the present specification e.g., IL-1RD5 combined with IL-1RD9, Additionally, both agonists or antagonists, are contemplated in combination with compositions of the invention. Every carrier should be both pharmaceutically and physiologically acceptable in the sense of being compatible with the other ingredients and not injurious to the patient. Formulations comprise at least one active ingredient, as defined above, together with one or more acceptable carriers thereof. Formulations include those suitable for oral, rectal, nasal, or parenteral (including subcutaneous, intramuscular, intravenous and intradermal) administration. The formulations may conveniently be presented in unit dosage form and may be prepared by methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Penn.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y. The therapy of this invention may be combined with or used in association with other therapeutic agents, particularly agonists or antagonists of other IL-1 family members.

IX. Ligands

The description of the IL-1 receptors herein provide means to identify ligands, as described above. Such ligand should bind specifically to the respective receptor with reasonably high affinity. Typical ligand receptor binding constants will be at least about 30 mM, e.g., generally at least about 3 mM, more generally at least about 300 $\mu$M, typically at least about 30 $\mu$M, 3 $\mu$M, 300 nM, 30 nM, etc. Various constructs are made available which allow either labeling of the receptor to detect its ligand. For example, directly labeling IL-1R, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available IL-1R sequences. See, e.g., Fields and Song (1989) *Nature* 340:245–246.

Generally, descriptions of IL-1Rs will be analogously applicable to individual specific embodiments directed to IL-1RD8, IL-1RD9, or IL-1RD10 reagents and compositions.

The broad scope of this invention is best understood with reference to the following examples, which are not intended to limit the inventions to the specific embodiments.

EXAMPLES

I. General Methods

Some of the standard methods are described or referenced, e.g., in Maniatis, et al. (1982) *Molecular Cloning A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, N.Y.; Ausubel, et al. *Biology* Greene Publishing Associates, Brooklyn, N.Y.; or Ausubel, et al. (1987 and Supplements) *Current Protocols in Molecular Biology,* Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Coligan, et al. (ed. 1996 and periodic supplements) *Current Protocols In Protein Science* Greene/Wiley, New York; Deutscher (1990) "Guide to Protein Purification" in *Methods in Enzymology,* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering. Principle and Methods* 12:87–98, Plenum Press, N.Y.; and Crowe, et al. (1992) *OIAexpress: The High Level Expression & Protein Purification System* QUIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank, NCBI, SWISSPROT, and others.

Many techniques applicable to IL-10 receptors may be applied to IL-1Rs, as described, e.g., in U.S. Ser. No. 08/110,683 (IL-10 receptor), which is incorporated herein by reference for all purposes. Also, while many of the techniques described are directed to the IL-1RD9 reagents, corresponding methods will typically be applicable with the IL-1RD8, and IL-1RD10 reagents. See also, U.S. Ser. No. 60/065,776, filed Nov. 17, 1997, and U.S. Ser. No. 60/078, 008, filed Mar. 12, 1998, both of which are incorporated herein by reference.

II. Computational Analysis

Human sequences related to IL-1Rs were identified from various EST databases using, e.g., the BLAST server (Altschul, et al. (1994) *Nature Genet.* 6:119–129). More sensitive pattern- and profile-based methods (Bork and Gibson (1996) *Meth. Enzymol.* 266:162–184) were used to identify a fragment of a gene which exhibited certain homology to the IL-1Rs.

III. Cloning of Full-length Human IL-1R cDNAs

PCR primers derived from the IL-1RD8, IL-1RD9, or IL-1RD10 sequences are used (Nomura, et al. (1994) *DNA Res.* 1:27–35) to probe an appropriate human cDNA library to yield a full length IL-1RD9 or IL-1RD10 cDNA sequence or to probe a human erythroleukemic, TF-1 cell line-derived cDNA library (Kitamura, et al. (1989) *Blood* 73:375–380) to yield the IL-1R8 cDNA sequence. Full length cDNAs for human IL-1RD9 are cloned, e.g., by DNA hybridization screening of $\lambda$gt10 phage. PCR reactions were conducted using T. aquaticus Taqplus DNA polymerase (Stratagene) under appropriate conditions.

IV. Localization of IL-1RD8, IL-1RD9, and IL-1RD10 mRNA

Human multiple tissue (Cat#1, 2) and cancer cell line blots (Cat#7757–1), containing approximately 2 $\mu$g of poly (A)$^+$ RNA per lane, are purchased from Clontech (Palo Alto, Clif.). Probes are radiolabeled with [$\alpha$-$^{32}$P] dATP, e.g., using the Amersham Rediprime random primer labeling kit (RPN1633). Prehybridization and hybridizations are performed at 65° C. in 0.5 M Na$_2$HPO$_4$, 7% SDS, 0.5 M EDTA (pH 8.0). High stringency washes are conducted, e.g., at 65° C. with two initial washes in 2×SSC, 0.1% SDS for 40 min followed by a subsequent wash in 0.1×SSC, 0.1% SDS for 20 min. Membranes are then exposed at −70° C. to X-Ray film (Kodak) in the presence of intensifying screens. More detailed studies by cDNA library Southerns are performed with selected human IL-1RD9 clones to examine their expression in hemopoietic or other cell subsets.

Two prediction algorithms that take advantage of the patterns of conservation and variation in multiply aligned sequences, PHD (Rost and Sander (1994) *Proteins* 19:55–72) and DSC (King and Sternberg (1996) *Protein Sci.* 5:2298–2310), are used.

Alternatively, two appropriate primers are selected from Tables 1, 2, or 3. RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal. Northern blots can be performed.

Message for genes encoding, e.g., IL-1RD9 will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described. And the identification of functional receptor subunit pairings will allow for prediction of what cells express the combination of receptor subunits which will result in a physiological responsiveness to each of the IL-1 ligands.

The message for IL-1RD9 is quite rare, as it is not found with a degree of frequency in the available sequence databases. This suggests, e.g., a very rare message, or a highly restricted distribution. IL-1R9 is expressed predominantly on T cells, NK cells, monocytes and dendritic cells.

Southern Analysis on cDNA libraries can be performed: DNA (5 μg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation may include, e.g.: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO- T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 h (D102); DC 70% CD1a+, from CD34+GM-CSF, TNFα 12 days, activated with PMA and ionomycin for 6 h (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 h pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte super for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); tonsil inflamed, from 12 year old (X100); psoriasis human skin sample; normal human skin sample; pool of rheumatioid arthritis human; Hashimoto's thryroiditis thryroid; normal human throid; ulcerativel colitis human colon; normal human colon; normal weight monkey colon; pheumocysitc carnii pneumonia lung; allergic lung; poll of three heavy smoker human lung; pool of two normal human lung; Ascaris-challenged monkey lung, 24hr; Ascaris-challenged monkey lung, 4hr; normal weight monkey lung.

IL-1RD8 message is described below in Table 5. There appears to be a correlation between developmental stage of tissues and the levels of messages: fetal and transformed tissues express high levels, whereas normal, adult tissues express low levels (with the exception of skeletal muscle). Further insights into this phenomenon will need further experiments.

Message for genes encoding IL-1RD8 will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described. And the identification of functional receptor subunit pairings will allow for prediction of what cells express the combination of receptor subunits which will result in a physiological responsiveness to each of the IL-1 ligands.

Table 5: Multiple Tissue Northern Blots were screened with a radiolabeled probe, encompassing the cytoplasmic region of Interleukin-1 receptor R8 (IL-1RD8). The results are summarized below:

In all cases listed there is a smaller band at 3.4 Kb and in a few cases a larger band at 4.0 Kb as well.

| Tissue | 3.4 kb | 4.0 kb |
|---|---|---|
| Spleen | weak | |
| Thymus | weak | |
| Prostate | weak | |
| Testis | weak | |
| Ovary | weak | |
| Small Intestine | weak | |
| Colon (mucosal lining) | weak | |
| Peripheral Blood Leukocyte | weak | |
| Heart | moderate | |
| Brain | weak | |
| Placenta | moderate | |
| Lung | weak | |
| Liver | weak | |
| Skeletal Muscle | strong | |
| Kidney | weak | |
| Pancreas | weak | |
| Fetal brain | strong | weak |
| Fetal lung | strong | weak |
| Fetal Liver | strong | weak |
| Fetal Kidney | strong | weak |
| proleukocytic leukemia HL-60 | strong | |
| HeLa Cell S3 | very strong | weak |
| Chronic myelogenous leukemia, K-562 | very strong | weak |
| Lymphoblastic leukemia, MOLT-4 | weak | |
| Burkitt's lymphoma Rajii | moderate | |
| Colorectal adenocarcinoma SW40 | very strong | strong |
| Lung carcinoma A549 | strong | strong |
| Melanoma | very strong | weak |

V. Cloning of Species Counterparts of IL-1RDs

Various strategies are used to obtain species counterparts of IL-1RD8, IL-1RD9, and IL-1RD10 preferably from other primates. One method is by cross hybridization using closely related species DNA probes. It may be useful to go into evolutionarily similar species as intermediate steps. Another method is by using specific PCR primers based on the identification of blocks of similarity or difference between genes, e.g., areas of highly conserved or nonconserved polypeptide or nucleotide sequence. In addition, gene sequence databases may be screened for related sequences from other species.

VI. Production of Mammalian IL-1RD Protein

An appropriate, e.g., GST, fusion construct is engineered for expression, e.g., in E. coli. For example, a mouse IGIF pGex plasmid is constructed and transformed into E. coli. Freshly transformed cells are grown, e.g., in LB medium containing 50 $\mu$g/ml ampicillin and induced with IPTG (Sigma, St. Louis, Mo.). After overnight induction, the bacteria are harvested and the pellets containing, e.g., the IL-1R8 polypeptide are isolated. The pellets are homogenized, e.g., in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the IL-1R polypeptide is filtered and passed over a glutathione-SEPHAROSE column equilibrated in 50 mM Tris-base pH 8.0. The fractions containing the IL-1RD9-GST fusion protein are pooled and cleaved, e.g., with thrombin (Enzyme Research Laboratories, Inc., South Bend, Ind.). The cleaved pool is then passed over a Q-SEPHAROSE column equilibrated in 50 mM Tris-base. Fractions containing IL-1RD9 are pooled and diluted in cold distilled $H_2O$, to lower the conductivity, and passed back over a fresh Q-Sepharose column, alone or in succession with an immunoaffinity antibody column. Fractions containing the IL-1RD9 polypeptide are pooled, aliquoted, and stored in the −70° C. freezer.

Comparison of the CD spectrum with IL-1R polypeptide may suggest that the protein is correctly folded. See Hazuda, et al. (1969) J. Biol. Chem. 264:1689–1693.

VII. Determining Physiological Forms of Receptors

The IL-1$\alpha$ and IL-1$\beta$ ligands bind an IL-1RD1 as the primary receptor and this complex then forms a high affinity receptor complex with the IL-1RD3. Such receptor subunits are probably shared with the receptors for the new IL-1 ligand family members. See, e.g., U.S. Ser. No. 60/044,165 and U.S. Ser. No. 60/055,111. Combination of the IL-1RD9 (a subunit type, based upon sequence analysis) will combine with the IL-1RD5 ( subunit type, based upon sequence analysis) to form a heterodimer receptor. The IL-1$\delta$ and IL-1$\epsilon$ ligands each probably signal through a receptor comprising the association of IL-1RD4, IL-1RD6, or IL-1RD9 (alpha components) with IL-1RD3, IL-1RD8, or IL-1RD10 (beta components).

These defined subunit combinations can be tested now with the provided reagents. In particular, appropriate constructs can be made for transformation or transfection of subunits into cells. Constructs for the alpha chains, e.g., IL-1RD1, IL-1RD4, IL-1RD6, and IL-1RD9 forms can be made. Likewise for the beta subunits IL-1RD3, IL-1RD5, IL-1RD7, and IL-1RD8. Structurally, the IL-1RD10 is most similar to the IL-1RD8, suggesting that it may also be a beta receptor subunit. Combinatorial transfections of transformations can make cells expressing defined subunits, which can be tested for response to each of the IL-1 ligands. Appropriate cell types can be used, e.g., 293 T cells, Jurkat cells, with, e.g., a nuclear kappa B (NF$\kappa$b) controlled luciferase reporter construct such as described e.g., in Otieno et al.,(1997) Am J Physiol 273:F136–F143.

Such combinations of various IL-1 ligands and receptors were tested to determine if a functional signaling complex had been formed using an NF$\kappa$b-controlled luciferase reporter construct to indicate formation of a functional signaling complex (+) or failure to form a functional signaling complex (−). The results, presented below, $IL$-1$\alpha$+$IL$-1$\beta$+$IL$-1$RD$1+$IL$-1$RD$3=+;

$IL$-1$\alpha$+$IL$-1$\beta$+$IL$-1$RD$1+$IL$-1$RD$5=+;

$IL$-1$\alpha$+$IL$-1$\beta$+$IL$-1$RD$1+$IL$-1$RD$8=+;

$IL$-1$\alpha$+$IL$-1$\beta$+$IL$-1$RD$1+$IL$-1$RD$10 may =+/?;

suggest that IL-1RD3, IL-1RD5, IL-1RD8, and IL-1RD10 may functionally substitute for each other when in combination with IL-1$\alpha$+IL-1$\beta$+IL-1RD1.

Other combinations (below) demonstrate a failure of functional substitution; suggesting the importance of contextual dependence on substitution e.g., IL-1RD3, and IL-1RD8 cannot functionally replace IL-1RD5 in the following combination: IL-1$\gamma$+IL-1RD9 +IL-1RD5.

$IL$-1$\gamma$+$IL$-1$RD$9+$IL$-1$RD$5=+;

$IL$-1$\gamma$+$IL$-1$RD$9+$IL$-1$RD$3=−;

$IL$-1$\gamma$+$IL$-1$RD$9+$IL$-1$RD$8=−;

A further series of experiments tested the ability of mouse (m) and human (h) homologues to functionally substitute for each other. The results, shown below, $mIL$-1$\gamma$+$mIL$-1$RD$5+$mIL$-1$RD$9=+;

$mIL$-1$\gamma$+$mIL$-1$RD$5+$hIL$-1$RD$9=−;

$mIL$-1$\gamma$+$hIL$-1$RD$5+$hIL$-1$RD$9=−;

mIL-1γ+hIL-1RD5+mIL-1RD9=−;

hIL-1γ+mIL-1RD5+mIL-1RD9=−;

hIL-1γ+mIL-1RD5+hIL-1RD9=−;

hIL-1γ+hIL-1RD5+mIL-1RD9=−;

hIL-1γ+hIL-1RD5+hIL-1RD9=+;

suggest that species homogeneity is required to form a functioning complex in this particular constellation of ligand and receptor units partner, i.e., ligand, preferably membrane associated. Standard staining techniques are used to detect or sort surface expressed ligand, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3 \times 10^5$ cells per chamber in 1.5 ml of growth media. Incubate overnight at 37° C.

On day 1 for each sample, prepare 0.5 ml of a solution of 66 μg/ml DEAE-dextran, 66 μm chloroquine, and 4 μg DNA in serum free DME. For each set, a positive control is prepared, e.g., of IL-1R-FLAG cDNA at 1 and 1/200 dilution, and a negative mock. Rinse cells with serum free DME. Add the DNA solution and incubate 5 h at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 μl/ml of 1 M NaN$_3$ for 20 min. Cells are then washed with HBSS/saponin 1×. Add appropriate IL-1R or IL-1R/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85–90° C.

Evaluate positive staining of pools and progressively subclone to isolation of single genes responsible for the binding.

Alternatively, IL-1R reagents are used to affinity purify or sort out cells expressing a putative ligand. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of an IL-1R fusion construct, or by use of antibodies raised against the first antibodies. Recursive cycles of selection and amplification lead to enrichment of appropriate clones and eventual isolation of receptor expressing clones.

Phage expression libraries can be screened by mammalian IL-1Rs. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 1737 base pairs
      (B) TYPE: nucleic acid
      (C) STRANDEDNESS: single
      (D) TOPOLOGY: linear (ii) MOLECULE TYPE: cDNA (iii) HYPOTHETICAL: YES (ix) FEATURE:
      (A) NAME/KEY: CDS
      (B) LOCATION: 1..1737

(ix) FEATURE:
      (A) NAME/KEY: misc_feature
      (B) LOCATION: 342..343
      (D) OTHER INFORMATION: /note= "splice junction"

```
    (ix) FEATURE:
         (A) NAME/KEY: misc_feature
         (B) LOCATION: 453..454
         (D) OTHER INFORMATION: /note= "splice junction"

(ix) FEATURE:
         (A) NAME/KEY: misc_feature
         (B) LOCATION: 756..757
         (D) OTHER INFORMATION: /note= "splice junction"

(ix) FEATURE:
         (A) NAME/KEY: misc_feature
         (B) LOCATION: 885..886
         (D) OTHER INFORMATION: /note= "splice junction"

(ix) FEATURE:
         (A) NAME/KEY: misc_feature
         (B) LOCATION: 1033..1034
         (D) OTHER INFORMATION: /note= "splice junction"

(ix) FEATURE:
         (A) NAME/KEY: misc_feature
         (B) LOCATION: 1177..1178
         (D) OTHER INFORMATION: /note= "splice junction"

(ix) FEATURE:
         (A) NAME/KEY: misc_feature
         (B) LOCATION: 1350..1351
         (D) OTHER INFORMATION: /note= "splice junction"

(xi) SEQUENCE DESCRIPTION: SEQ ID NO:1:

TTA CTG CTC ACA CTA TTA GTG TCA ACA ATG CTC ACT GTA TCT TAT ACC        48
Leu Leu Leu Thr Leu Leu Val Ser Thr Met Leu Thr Val Ser Tyr Thr
 1               5                  10                  15

TCT TCT GAT TTT CTT TCA GTG GAT GGC TGC ATT GAC TGG TCA GTG GAT        96
Ser Ser Asp Phe Leu Ser Val Asp Gly Cys Ile Asp Trp Ser Val Asp
             20                  25                  30

CTC AAG ACA TAC ATG GCT TTG GCA GGT GAA CCA GTC CGA GTG AAA TGT       144
Leu Lys Thr Tyr Met Ala Leu Ala Gly Glu Pro Val Arg Val Lys Cys
         35                  40                  45

GCC CTT TTC TAC AGT TAT ATT CGT ACC AAC TAT AGC ACG GCC CAG AGC       192
Ala Leu Phe Tyr Ser Tyr Ile Arg Thr Asn Tyr Ser Thr Ala Gln Ser
     50                  55                  60

ACT GGG CTC AGG CTT ATG TGG TAC AAA AAC AAA GGT GAT TTG GAA GAG       240
Thr Gly Leu Arg Leu Met Trp Tyr Lys Asn Lys Gly Asp Leu Glu Glu
 65                  70                  75                  80

CCC ATC ATC TTT TCA GAG GTC AGG ATG AGC AAA GAG GAA GAT TCA ATA       288
Pro Ile Ile Phe Ser Glu Val Arg Met Ser Lys Glu Glu Asp Ser Ile
                 85                  90                  95

TGG TTT CAC TCA GCT GAG GCA CAA GAC AGT GGA TTC TAC ACT TGT GTT       336
Trp Phe His Ser Ala Glu Ala Gln Asp Ser Gly Phe Tyr Thr Cys Val
             100                 105                 110

TTA AGG AAC TCA ACA TAT TGC ATG AAG GTG TCA ATG TCC TTG ACT GTT       384
Leu Arg Asn Ser Thr Tyr Cys Met Lys Val Ser Met Ser Leu Thr Val
         115                 120                 125

GCA GAG AAT GAA TCA GGC CTG TGC TAC AAC AGC AGG ATC CGC TAT TTA       432
Ala Glu Asn Glu Ser Gly Leu Cys Tyr Asn Ser Arg Ile Arg Tyr Leu
     130                 135                 140

GAA AAA TCT GAA GTC ACT AAA AGA AAG GAG ATC TCC TGT CCA GAC ATG       480
Glu Lys Ser Glu Val Thr Lys Arg Lys Glu Ile Ser Cys Pro Asp Met
145                 150                 155                 160

GAT GAC TTT AAA AAG TCC GAT CAG GAG CCT GAT GTT GTG TGG TAT AAG       528
Asp Asp Phe Lys Lys Ser Asp Gln Glu Pro Asp Val Val Trp Tyr Lys
                 165                 170                 175

GAA TGC AAG CCA AAA ATG TGG AGA AGC ATA ATA ATA CAG AAA GGA AAT       576
Glu Cys Lys Pro Lys Met Trp Arg Ser Ile Ile Ile Gln Lys Gly Asn
             180                 185                 190
```

```
GCT CTT CTG ATC CAA GAA GTT CAA GAA GAA GAT GGA GGA AAT TAC ACA    624
Ala Leu Leu Ile Gln Glu Val Gln Glu Glu Asp Gly Gly Asn Tyr Thr
        195                 200                 205

TGT GAA CTT AAA TAT GAA GGA AAA CTT GTA AGA CGA ACA ACT GAA TTG    672
Cys Glu Leu Lys Tyr Glu Gly Lys Leu Val Arg Arg Thr Thr Glu Leu
        210                 215                 220

AAA GTT ACA GCT TTA CTC ACA GAC AAG CCT CCC AAG CCA TTG TTC CCC    720
Lys Val Thr Ala Leu Leu Thr Asp Lys Pro Pro Lys Pro Leu Phe Pro
225                 230                 235                 240

ATG GAG AAT CAG CCA AGT GTT ATA GAT GTC CAG CTG GGT AAG CCT CTG    768
Met Glu Asn Gln Pro Ser Val Ile Asp Val Gln Leu Gly Lys Pro Leu
                245                 250                 255

AAC ATC CCC TGC AAA GCA TTC TTC GGA TTC AGT GGA GAG TCT GGG CCA    816
Asn Ile Pro Cys Lys Ala Phe Phe Gly Phe Ser Gly Glu Ser Gly Pro
            260                 265                 270

ATG ATC TAC TGG ATG AAA GGA GAA AAG TTT ATT GAA GAA CTG GCA GGT    864
Met Ile Tyr Trp Met Lys Gly Glu Lys Phe Ile Glu Glu Leu Ala Gly
        275                 280                 285

CAC ATT AGA GAA GGT GAA ATA AGG CTT CTC AAA GAG CAT CTT GGA GAA    912
His Ile Arg Glu Gly Glu Ile Arg Leu Leu Lys Glu His Leu Gly Glu
        290                 295                 300

AAA GAA GTT GAA TTG GCA CTC ATC TTT GAC TCA GTT GTG GAA GCT GAC    960
Lys Glu Val Glu Leu Ala Leu Ile Phe Asp Ser Val Val Glu Ala Asp
305                 310                 315                 320

CTG GCG AAT TAT ACC TGC CAT GTT GAA AAC CGA AAT GGA CGG AAA CAT   1008
Leu Ala Asn Tyr Thr Cys His Val Glu Asn Arg Asn Gly Arg Lys His
                325                 330                 335

GCC AGT GTT TTG CTG CGT AAA AAG GAT TTA ATC TAT AAA ATT GAG CTT   1056
Ala Ser Val Leu Leu Arg Lys Lys Asp Leu Ile Tyr Lys Ile Glu Leu
                340                 345                 350

GCA GGG GGC CTG GGA GCA ATC TTC CTC CTC CTT GTA CTG CTG GTG GTC   1104
Ala Gly Gly Leu Gly Ala Ile Phe Leu Leu Leu Val Leu Leu Val Val
                355                 360                 365

ATT TAC AAA TGC TAC AAC ATT GAA TTG ATG CTC TTC TAC AGG CAG CAC   1152
Ile Tyr Lys Cys Tyr Asn Ile Glu Leu Met Leu Phe Tyr Arg Gln His
        370                 375                 380

TTT GGA GCT GAT GAA ACT AAT GAT GAC AAC AAG GAA TAT GAT GCC TAT   1200
Phe Gly Ala Asp Glu Thr Asn Asp Asp Asn Lys Glu Tyr Asp Ala Tyr
385                 390                 395                 400

CTC TCT TAC ACA AAA GTG GAC CAA GAT ACT TTA GAC TGT GAC AAT CCT   1248
Leu Ser Tyr Thr Lys Val Asp Gln Asp Thr Leu Asp Cys Asp Asn Pro
                405                 410                 415

GAA GAA GAG CAG TTT GCT CTT GAA GTA CTG CCA GAT GTC CTG GAA AAA   1296
Glu Glu Glu Gln Phe Ala Leu Glu Val Leu Pro Asp Val Leu Glu Lys
                420                 425                 430

CAC TAT GGA TAT AAA CTC TTC ATC CCA GAA AGA GAC CTG ATT CCA AGT   1344
His Tyr Gly Tyr Lys Leu Phe Ile Pro Glu Arg Asp Leu Ile Pro Ser
                435                 440                 445

GGA AGT GCA TAC ATG GAA GAT CTC ACA AGA TAT GTT GAA CAA AGC AGA   1392
Gly Ser Ala Tyr Met Glu Asp Leu Thr Arg Tyr Val Glu Gln Ser Arg
        450                 455                 460

AGA CTT ATT ATC GTG CTA ACT CCA GAC TAT ATT CTC AGA CGG GGA TGG   1440
Arg Leu Ile Ile Val Leu Thr Pro Asp Tyr Ile Leu Arg Arg Gly Trp
465                 470                 475                 480

AGT ATT TTC GAA CTG GAA AGC AGA CTC CAT AAC ATG CTA GTC AGT GGA   1488
Ser Ile Phe Glu Leu Glu Ser Arg Leu His Asn Met Leu Val Ser Gly
                485                 490                 495

GAA ATC AAA GTG ATT TTG ATT GAG TGT ACA GAA TTA AAA GGG AAA GTG   1536
Glu Ile Lys Val Ile Leu Ile Glu Cys Thr Glu Leu Lys Gly Lys Val
```

```
                500                 505                 510
AAT TGC CAG GAA GTG GAA TCA CTA AAG CGT AGC ATC AAA CTT CTG TCC    1584
Asn Cys Gln Glu Val Glu Ser Leu Lys Arg Ser Ile Lys Leu Leu Ser
            515                 520                 525

CTG ATC AAG TGG AAG GGA TCC AAA AGC AGC AAA TTA AAT TCT AAG TTT    1632
Leu Ile Lys Trp Lys Gly Ser Lys Ser Ser Lys Leu Asn Ser Lys Phe
530                 535                 540

TGG AAG CAC TTA GTA TAT GAA ATG CCC ATC AAG AAA AAA GAA ATG CTA    1680
Trp Lys His Leu Val Tyr Glu Met Pro Ile Lys Lys Lys Glu Met Leu
545                 550                 555                 560

CCT CGG TGC CAT GTT CTG GAC TCC GCA GAA CAA GGA CTT TTT GGA GAA    1728
Pro Arg Cys His Val Leu Asp Ser Ala Glu Gln Gly Leu Phe Gly Glu
            565                 570                 575

CTC CAG CCT                                                        1737
Leu Gln Pro
```

(2) INFORMATION FOR SEQ ID NO:2:

(i) SEQUENCE CHARACTERISTICS:
        (A) LENGTH: 579 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Leu Leu Thr Leu Leu Val Ser Thr Met Leu Thr Val Ser Tyr Thr
1               5                   10                  15

Ser Ser Asp Phe Leu Ser Val Asp Gly Cys Ile Asp Trp Ser Val Asp
                20                  25                  30

Leu Lys Thr Tyr Met Ala Leu Ala Gly Glu Pro Val Arg Val Lys Cys
            35                  40                  45

Ala Leu Phe Tyr Ser Tyr Ile Arg Thr Asn Tyr Ser Thr Ala Gln Ser
        50                  55                  60

Thr Gly Leu Arg Leu Met Trp Tyr Lys Asn Lys Gly Asp Leu Glu Glu
65                  70                  75                  80

Pro Ile Ile Phe Ser Glu Val Arg Met Ser Lys Glu Glu Asp Ser Ile
                85                  90                  95

Trp Phe His Ser Ala Glu Ala Gln Asp Ser Gly Phe Tyr Thr Cys Val
                100                 105                 110

Leu Arg Asn Ser Thr Tyr Cys Met Lys Val Ser Met Ser Leu Thr Val
            115                 120                 125

Ala Glu Asn Glu Ser Gly Leu Cys Tyr Asn Ser Arg Ile Arg Tyr Leu
        130                 135                 140

Glu Lys Ser Glu Val Thr Lys Arg Lys Glu Ile Ser Cys Pro Asp Met
145                 150                 155                 160

Asp Asp Phe Lys Lys Ser Asp Gln Glu Pro Asp Val Val Trp Tyr Lys
                165                 170                 175

Glu Cys Lys Pro Lys Met Trp Arg Ser Ile Ile Gln Lys Gly Asn
                180                 185                 190

Ala Leu Leu Ile Gln Glu Val Gln Glu Asp Gly Gly Asn Tyr Thr
            195                 200                 205

Cys Glu Leu Lys Tyr Glu Gly Lys Leu Val Arg Arg Thr Thr Glu Leu
        210                 215                 220

Lys Val Thr Ala Leu Leu Thr Asp Lys Pro Pro Lys Pro Leu Phe Pro
225                 230                 235                 240

Met Glu Asn Gln Pro Ser Val Ile Asp Val Gln Leu Gly Lys Pro Leu
```

-continued

```
                245                 250                 255
Asn Ile Pro Cys Lys Ala Phe Phe Gly Phe Ser Gly Glu Ser Gly Pro
            260                 265                 270
Met Ile Tyr Trp Met Lys Gly Glu Lys Phe Ile Glu Glu Leu Ala Gly
        275                 280                 285
His Ile Arg Glu Gly Glu Ile Arg Leu Leu Lys Glu His Leu Gly Glu
    290                 295                 300
Lys Glu Val Glu Leu Ala Leu Ile Phe Asp Ser Val Val Glu Ala Asp
305                 310                 315                 320
Leu Ala Asn Tyr Thr Cys His Val Glu Asn Arg Asn Gly Arg Lys His
                325                 330                 335
Ala Ser Val Leu Leu Arg Lys Lys Asp Leu Ile Tyr Lys Ile Glu Leu
            340                 345                 350
Ala Gly Gly Leu Gly Ala Ile Phe Leu Leu Val Leu Leu Val Val
        355                 360                 365
Ile Tyr Lys Cys Tyr Asn Ile Glu Leu Met Leu Phe Tyr Arg Gln His
    370                 375                 380
Phe Gly Ala Asp Glu Thr Asn Asp Asp Asn Lys Glu Tyr Asp Ala Tyr
385                 390                 395                 400
Leu Ser Tyr Thr Lys Val Asp Gln Asp Thr Leu Asp Cys Asp Asn Pro
                405                 410                 415
Glu Glu Glu Gln Phe Ala Leu Glu Val Leu Pro Asp Val Leu Glu Lys
            420                 425                 430
His Tyr Gly Tyr Lys Leu Phe Ile Pro Glu Arg Asp Leu Ile Pro Ser
        435                 440                 445
Gly Ser Ala Tyr Met Glu Asp Leu Thr Arg Tyr Val Glu Gln Ser Arg
    450                 455                 460
Arg Leu Ile Ile Val Leu Thr Pro Asp Tyr Ile Leu Arg Arg Gly Trp
465                 470                 475                 480
Ser Ile Phe Glu Leu Glu Ser Arg Leu His Asn Met Leu Val Ser Gly
                485                 490                 495
Glu Ile Lys Val Ile Leu Ile Glu Cys Thr Glu Leu Lys Gly Lys Val
            500                 505                 510
Asn Cys Gln Glu Val Glu Ser Leu Lys Arg Ser Ile Lys Leu Leu Ser
        515                 520                 525
Leu Ile Lys Trp Lys Gly Ser Lys Ser Ser Lys Leu Asn Ser Lys Phe
    530                 535                 540
Trp Lys His Leu Val Tyr Glu Met Pro Ile Lys Lys Lys Glu Met Leu
545                 550                 555                 560
Pro Arg Cys His Val Leu Asp Ser Ala Glu Gln Gly Leu Phe Gly Glu
                565                 570                 575
Leu Gln Pro (2) INFORMATION FOR SEQ ID NO:3:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2058
```

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | AAG | CCA | CCA | TTT | CTT | TTG | GCC | CTT | GTG | GTC | TGT | TCT | GTA | GTC | AGC | 48 |
| Met | Lys | Pro | Pro | Phe | Leu | Leu | Ala | Leu | Val | Val | Cys | Ser | Val | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ACA | AAT | CTG | AAG | ATG | GTG | TCA | AAG | AGA | AAT | TCT | GTG | GAT | GGC | TGC | ATT | 96 |
| Thr | Asn | Leu | Lys | Met | Val | Ser | Lys | Arg | Asn | Ser | Val | Asp | Gly | Cys | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| GAC | TGG | TCA | GTG | GAT | CTC | AAG | ACA | TAC | ATG | GCT | TTG | GCA | GGT | GAA | CCA | 144 |
| Asp | Trp | Ser | Val | Asp | Leu | Lys | Thr | Tyr | Met | Ala | Leu | Ala | Gly | Glu | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| GTC | CGA | GTG | AAA | TGT | GCC | CTT | TTC | TAC | AGT | TAT | ATT | CGT | ACC | AAC | TAT | 192 |
| Val | Arg | Val | Lys | Cys | Ala | Leu | Phe | Tyr | Ser | Tyr | Ile | Arg | Thr | Asn | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| AGC | ACG | GCC | CAG | AGC | ACT | GGG | CTC | AGG | CTT | ATG | TGG | TAC | AAA | AAC | AAA | 240 |
| Ser | Thr | Ala | Gln | Ser | Thr | Gly | Leu | Arg | Leu | Met | Trp | Tyr | Lys | Asn | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GGT | GAT | TTG | GAA | GAG | CCC | ATC | ATC | TTT | TCA | GAG | GTC | AGG | ATG | AGC | AAA | 288 |
| Gly | Asp | Leu | Glu | Glu | Pro | Ile | Ile | Phe | Ser | Glu | Val | Arg | Met | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| GAG | GAA | GAT | TCA | ATA | TGG | TTT | CAC | TCA | GCT | GAG | GCA | CAA | GAC | AGT | GGA | 336 |
| Glu | Glu | Asp | Ser | Ile | Trp | Phe | His | Ser | Ala | Glu | Ala | Gln | Asp | Ser | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| TTC | TAC | ACT | TGT | GTT | TTA | AGG | AAC | TCA | ACA | TAT | TGC | ATG | AAG | GTG | TCA | 384 |
| Phe | Tyr | Thr | Cys | Val | Leu | Arg | Asn | Ser | Thr | Tyr | Cys | Met | Lys | Val | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| ATG | TCC | TTG | ACT | GTT | GCA | GAG | AAT | GAA | TCA | GGC | CTG | TGC | TAC | AAC | AGC | 432 |
| Met | Ser | Leu | Thr | Val | Ala | Glu | Asn | Glu | Ser | Gly | Leu | Cys | Tyr | Asn | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| AGG | ATC | CGC | TAT | TTA | GAA | AAA | TCT | GAA | GTC | ACT | AAA | AGA | AAG | GAG | ATC | 480 |
| Arg | Ile | Arg | Tyr | Leu | Glu | Lys | Ser | Glu | Val | Thr | Lys | Arg | Lys | Glu | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TCC | TGT | CCA | GAC | ATG | GAT | GAC | TTT | AAA | AAG | TCC | GAT | CAG | GAG | CCT | GAT | 528 |
| Ser | Cys | Pro | Asp | Met | Asp | Asp | Phe | Lys | Lys | Ser | Asp | Gln | Glu | Pro | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| GTT | GTG | TGG | TAT | AAG | GAA | TGC | AAG | CCA | AAA | ATG | TGG | AGA | AGC | ATA | ATA | 576 |
| Val | Val | Trp | Tyr | Lys | Glu | Cys | Lys | Pro | Lys | Met | Trp | Arg | Ser | Ile | Ile | |
| | | | 180 | | | | | 185 | | | | | 190 | | | |

| | | | | | | | | | | | | | | | | |
|---|---|---|---|---|---|---|---|---|---|---|---|---|---|---|---|---|
| ATA | CAG | AAA | GGA | AAT | GCT | CTT | CTG | ATC | CAA | GAA | GTT | CAA | GAA | GAA | GAT | 624 |
| Ile | Gln | Lys | Gly | Asn | Ala | Leu | Leu | Ile | Gln | Glu | Val | Gln | Glu | Glu | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| GGA | GGA | AAT | TAC | ACA | TGT | GAA | CTT | AAA | TAT | GAA | GGA | AAA | CTT | GTA | AGA | 672 |
| Gly | Gly | Asn | Tyr | Thr | Cys | Glu | Leu | Lys | Tyr | Glu | Gly | Lys | Leu | Val | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| CGA | ACA | ACT | GAA | TTG | AAA | GTT | ACA | GCT | TTA | CTC | ACA | GAC | AAG | CCT | CCC | 720 |
| Arg | Thr | Thr | Glu | Leu | Lys | Val | Thr | Ala | Leu | Leu | Thr | Asp | Lys | Pro | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| AAG | CCA | TTG | TTC | CCC | ATG | GAG | AAT | CAG | CCA | AGT | GTT | ATA | GAT | GTC | CAG | 768 |
| Lys | Pro | Leu | Phe | Pro | Met | Glu | Asn | Gln | Pro | Ser | Val | Ile | Asp | Val | Gln | |
| | | | | 245 | | | | | 250 | | | | | 255 | | |

| | | | | | | | | | | | | | | | | |
|---|---|---|---|---|---|---|---|---|---|---|---|---|---|---|---|---|
| CTG | GGT | AAG | CCT | CTG | AAC | ATC | CCC | TGC | AAA | GCA | TTC | TTC | GGA | TTC | AGT | 816 |
| Leu | Gly | Lys | Pro | Leu | Asn | Ile | Pro | Cys | Lys | Ala | Phe | Phe | Gly | Phe | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| GGA | GAG | TCT | GGG | CCA | ATG | ATC | TAC | TGG | ATG | AAA | GGA | GAA | AAG | TTT | ATT | 864 |
| Gly | Glu | Ser | Gly | Pro | Met | Ile | Tyr | Trp | Met | Lys | Gly | Glu | Lys | Phe | Ile | |
| | | 275 | | | | | 280 | | | | | 285 | | | | |

| | | | | | | | | | | | | | | | | |
|---|---|---|---|---|---|---|---|---|---|---|---|---|---|---|---|---|
| GAA | GAA | CTG | GCA | GGT | CAC | ATT | AGA | GAA | GGT | GAA | ATA | AGG | CTT | CTC | AAA | 912 |
| Glu | Glu | Leu | Ala | Gly | His | Ile | Arg | Glu | Gly | Glu | Ile | Arg | Leu | Leu | Lys | |
| | 290 | | | | | 295 | | | | | 300 | | | | | |

| | | | | | | | | | | | | | | | | |
|---|---|---|---|---|---|---|---|---|---|---|---|---|---|---|---|---|
| GAG | CAT | CTT | GGA | GAA | AAA | GAA | GTT | GAA | TTG | GCA | CTC | ATC | TTT | GAC | TCA | 960 |

```
                                                          -continued

Glu His Leu Gly Glu Lys Glu Val Glu Leu Ala Leu Ile Phe Asp Ser
305                 310                 315                 320

GTT GTG GAA GCT GAC CTG GCG AAT TAT ACC TGC CAT GTT GAA AAC CGA        1008
Val Val Glu Ala Asp Leu Ala Asn Tyr Thr Cys His Val Glu Asn Arg
            325                 330                 335

AAT GGA CGG AAA CAT GCC AGT GTT TTG CTG CGT AAA AAG GAT TTA ATC        1056
Asn Gly Arg Lys His Ala Ser Val Leu Leu Arg Lys Lys Asp Leu Ile
            340                 345                 350

TAT AAA ATT GAG CTT GCA GGG GGC CTG GGA GCA ATC TTC CTC CTC CTT        1104
Tyr Lys Ile Glu Leu Ala Gly Gly Leu Gly Ala Ile Phe Leu Leu Leu
        355                 360                 365

GTA CTG CTG GTG GTC ATT TAC AAA TGC TAC AAC ATT GAA TTG ATG CTC        1152
Val Leu Leu Val Val Ile Tyr Lys Cys Tyr Asn Ile Glu Leu Met Leu
370                 375                 380

TTC TAC AGG CAG CAC TTT GGA GCT GAT GAA ACT AAT GAT GAC AAC AAG        1200
Phe Tyr Arg Gln His Phe Gly Ala Asp Glu Thr Asn Asp Asp Asn Lys
385                 390                 395                 400

GAA TAT GAT GCC TAT CTC TCT TAC ACA AAA GTG GAC CAA GAT ACT TTA        1248
Glu Tyr Asp Ala Tyr Leu Ser Tyr Thr Lys Val Asp Gln Asp Thr Leu
                405                 410                 415

GAC TGT GAC AAT CCT GAA GAA GAG CAG TTT GCT CTT GAA GTA CTG CCA        1296
Asp Cys Asp Asn Pro Glu Glu Glu Gln Phe Ala Leu Glu Val Leu Pro
            420                 425                 430

GAT GTC CTG GAA AAA CAC TAT GGA TAT AAA CTC TTC ATC CCA GAA AGA        1344
Asp Val Leu Glu Lys His Tyr Gly Tyr Lys Leu Phe Ile Pro Glu Arg
        435                 440                 445

GAC CTG ATT CCA AGT GGA ACA TAC ATG GAA GAT CTC ACA AGA TAT GTT        1392
Asp Leu Ile Pro Ser Gly Thr Tyr Met Glu Asp Leu Thr Arg Tyr Val
450                 455                 460

GAA CAA AGC AGA AGA CTT ATT ATC GTG CTA ACT CCA GAC TAT ATT CTC        1440
Glu Gln Ser Arg Arg Leu Ile Ile Val Leu Thr Pro Asp Tyr Ile Leu
465                 470                 475                 480

AGA CGG GGA TGG AGT ATT TTC GAA CTG GAA AGC AGA CTC CAT AAC ATG        1488
Arg Arg Gly Trp Ser Ile Phe Glu Leu Glu Ser Arg Leu His Asn Met
                485                 490                 495

CTA GTC AGT GGA GAA ATC AAA GTG ATT TTG ATT GAG TGT ACA GAA TTA        1536
Leu Val Ser Gly Glu Ile Lys Val Ile Leu Ile Glu Cys Thr Glu Leu
            500                 505                 510

AAA GGG AAA GTG AAT TGC AGG GAA GTG GAA TCA CTA AAG CGT AGC ATC        1584
Lys Gly Lys Val Asn Cys Gln Glu Val Glu Ser Leu Lys Arg Ser Ile
        515                 520                 525

AAA CTT CTG TCC CTG ATC AAG TGG AAG GGA TCC AAA AGC AGC AAA TTA        1632
Lys Leu Leu Ser Leu Ile Lys Trp Lys Gly Ser Lys Ser Ser Lys Leu
530                 535                 540

AAT TCT AAG TTT TGG AAG CAC TTA GTA TAT GAA ATG CCC ATC AAG AAA        1680
Asn Ser Lys Phe Trp Lys His Leu Val Tyr Glu Met Pro Ile Lys Lys
545                 550                 555                 560

AAA GAA ATG CTA CCT CGG TGC CAT GTT CTG GAC TCC GCA GAA CAA GGA        1728
Lys Glu Met Leu Pro Arg Cys His Val Leu Asp Ser Ala Glu Gln Gly
                565                 570                 575

CTT TTT GGA GAA CTC CAG CCT ATA CCC TCT ATT GCC ATG ACC AGT ACT        1776
Leu Phe Gly Glu Leu Gln Pro Ile Pro Ser Ile Ala Met Thr Ser Thr
            580                 585                 590

TCA GCC ACT CTG GTG TCA TCT CAG GCT GAT CTC CCT GAA TTC CAC CCT        1824
Ser Ala Thr Leu Val Ser Ser Gln Ala Asp Leu Pro Glu Phe His Pro
        595                 600                 605

TCA GAT TCA ATG CAA ATC AGG CAC TGT TGC AGA GGT TAT AAA CAT GAG        1872
Ser Asp Ser Met Gln Ile Arg His Cys Cys Arg Gly Tyr Lys His Glu
610                 615                 620
```

```
ATA CCA GCC ACG ACC TTG CCA GTA CCT TCC TTA GGC AAC CAC CAT ACT     1920
Ile Pro Ala Thr Thr Leu Pro Val Pro Ser Leu Gly Asn His His Thr
625                 630                 635                 640

TAT TGT AAC CTG CCT CTG ACG CTA CTC AAC GGA CAG CTA CCC CTT AAT     1968
Tyr Cys Asn Leu Pro Leu Thr Leu Leu Asn Gly Gln Leu Pro Leu Asn
                645                 650                 655

AAC ACC CTG AAA GAT ACC CAG GAA TTT CAC AGG AAC AGT TCT TTG CTG     2016
Asn Thr Leu Lys Asp Thr Gln Glu Phe His Arg Asn Ser Ser Leu Leu
            660                 665                 670

CCT TTA TCC TCC AAA GAG CTT AGC TTT ACC AGT GAT ATT TGG             2058
Pro Leu Ser Ser Lys Glu Leu Ser Phe Thr Ser Asp Ile Trp
        675                 680                 685

TAG                                                                  2061
```

(2) INFORMATION FOR SEQ ID NO:4:

(i) SEQUENCE CHARACTERISTICS:
        (A) LENGTH: 686 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Pro Pro Phe Leu Leu Ala Leu Val Val Cys Ser Val Val Ser
1               5                   10                  15

Thr Asn Leu Lys Met Val Ser Lys Arg Asn Ser Val Asp Gly Cys Ile
            20                  25                  30

Asp Trp Ser Val Asp Leu Lys Thr Tyr Met Ala Leu Ala Gly Glu Pro
        35                  40                  45

Val Arg Val Lys Cys Ala Leu Phe Tyr Ser Tyr Ile Arg Thr Asn Tyr
    50                  55                  60

Ser Thr Ala Gln Ser Thr Gly Leu Arg Leu Met Trp Tyr Lys Asn Lys
65              70                  75                  80

Gly Asp Leu Glu Glu Pro Ile Ile Phe Ser Glu Val Arg Met Ser Lys
            85                  90                  95

Glu Glu Asp Ser Ile Trp Phe His Ser Ala Glu Ala Gln Asp Ser Gly
        100                 105                 110

Phe Tyr Thr Cys Val Leu Arg Asn Ser Thr Tyr Cys Met Lys Val Ser
    115                 120                 125

Met Ser Leu Thr Val Ala Glu Asn Glu Ser Gly Leu Cys Tyr Asn Ser
130             135                 140

Arg Ile Arg Tyr Leu Glu Lys Ser Glu Val Thr Lys Arg Lys Glu Ile
145             150                 155                 160

Ser Cys Pro Asp Met Asp Asp Phe Lys Lys Ser Asp Gln Glu Pro Asp
            165                 170                 175

Val Val Trp Tyr Lys Glu Cys Lys Pro Lys Met Trp Arg Ser Ile Ile
        180                 185                 190

Ile Gln Lys Gly Asn Ala Leu Leu Ile Gln Glu Val Gln Glu Glu Asp
    195                 200                 205

Gly Gly Asn Tyr Thr Cys Glu Leu Lys Tyr Glu Gly Lys Leu Val Arg
    210                 215                 220

Arg Thr Thr Glu Leu Lys Val Thr Ala Leu Leu Thr Asp Lys Pro Pro
225             230                 235                 240

Lys Pro Leu Phe Pro Met Glu Asn Gln Pro Ser Val Ile Asp Val Gln
            245                 250                 255

Leu Gly Lys Pro Leu Asn Ile Pro Cys Lys Ala Phe Phe Gly Phe Ser
```

```
                    260                 265                 270
Gly Glu Ser Gly Pro Met Ile Tyr Trp Met Lys Gly Glu Lys Phe Ile
            275                 280                 285
Glu Glu Leu Ala Gly His Ile Arg Glu Gly Ile Arg Leu Leu Lys
    290                 295                 300
Glu His Leu Gly Glu Lys Glu Val Glu Leu Ala Leu Ile Phe Asp Ser
305                 310                 315                 320
Val Val Glu Ala Asp Leu Ala Asn Tyr Thr Cys His Val Glu Asn Arg
                325                 330                 335
Asn Gly Arg Lys His Ala Ser Val Leu Leu Arg Lys Lys Asp Leu Ile
            340                 345                 350
Tyr Lys Ile Glu Leu Ala Gly Gly Leu Gly Ala Ile Phe Leu Leu Leu
            355                 360                 365
Val Leu Leu Val Val Ile Tyr Lys Cys Tyr Asn Ile Glu Leu Met Leu
    370                 375                 380
Phe Tyr Arg Gln His Phe Gly Ala Asp Glu Thr Asn Asp Asp Asn Lys
385                 390                 395                 400
Glu Tyr Asp Ala Tyr Leu Ser Tyr Thr Lys Val Asp Gln Asp Thr Leu
                405                 410                 415
Asp Cys Asp Asn Pro Glu Glu Glu Gln Phe Ala Leu Glu Val Leu Pro
                420                 425                 430
Asp Val Leu Glu Lys His Tyr Gly Tyr Lys Leu Phe Ile Pro Glu Arg
            435                 440                 445
Asp Leu Ile Pro Ser Gly Thr Tyr Met Glu Asp Leu Thr Arg Tyr Val
    450                 455                 460
Glu Gln Ser Arg Arg Leu Ile Ile Val Leu Thr Pro Asp Tyr Ile Leu
465                 470                 475                 480
Arg Arg Gly Trp Ser Ile Phe Glu Leu Glu Ser Arg Leu His Asn Met
                485                 490                 495
Leu Val Ser Gly Glu Ile Lys Val Ile Leu Ile Glu Cys Thr Glu Leu
                500                 505                 510
Lys Gly Lys Val Asn Cys Gln Glu Val Glu Ser Leu Lys Arg Ser Ile
            515                 520                 525
Lys Leu Leu Ser Leu Ile Lys Trp Lys Gly Ser Lys Ser Ser Lys Leu
    530                 535                 540
Asn Ser Lys Phe Trp Lys His Leu Val Tyr Glu Met Pro Ile Lys Lys
545                 550                 555                 560
Lys Glu Met Leu Pro Arg Cys His Val Leu Asp Ser Ala Glu Gln Gly
                565                 570                 575
Leu Phe Gly Glu Leu Gln Pro Ile Pro Ser Ile Ala Met Thr Ser Thr
            580                 585                 590
Ser Ala Thr Leu Val Ser Ser Gln Ala Asp Leu Pro Glu Phe His Pro
            595                 600                 605
Ser Asp Ser Met Gln Ile Arg His Cys Cys Arg Gly Tyr Lys His Glu
    610                 615                 620
Ile Pro Ala Thr Thr Leu Pro Val Pro Ser Leu Gly Asn His His Thr
625                 630                 635                 640
Tyr Cys Asn Leu Pro Leu Thr Leu Leu Asn Gly Gln Leu Pro Leu Asn
                645                 650                 655
Asn Thr Leu Lys Asp Thr Gln Glu Phe His Arg Asn Ser Ser Leu Leu
            660                 665                 670
Pro Leu Ser Ser Lys Glu Leu Ser Phe Thr Ser Asp Ile Trp
    675                 680                 685
```

(2) INFORMATION FOR SEQ ID NO:5:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..480

(ix) FEATURE:
        (A) NAME/KEY: misc_feature
        (B) LOCATION: 9
        (D) OTHER INFORMATION: /note= "residues 9, 459, 462, 469,
            and 474 each may be A, C, G, or T; translated as C "

(ix) FEATURE:
        (A) NAME/KEY: misc_feature
        (B) LOCATION: 246
        (D) OTHER INFORMATION: /note= "residue 246 may be C or G;
            translated as C"

(ix) FEATURE:
        (A) NAME/KEY: misc_feature
        (B) LOCATION: 321
        (D) OTHER INFORMATION: /note= "residues 321, 335, 360, and
            423 each may be C or T; translated as C"

(ix) FEATURE:
        (A) NAME/KEY: misc_feature
        (B) LOCATION: 426
        (D) OTHER INFORMATION: /note= "residue 426 may be A or C;
            translated as C"

(xi) SEQUENCE DESCRIPTION: SEQ ID NO:5:

```
AAA TAT GGN TAT AGC CTG TTT TTC CTT GAA AGA AAT GTG GCT CCA GGA           48
Lys Tyr Gly Tyr Ser Leu Phe Phe Leu Glu Arg Asn Val Ala Pro Gly
  1               5                  10                  15

GGA GTG TAT GCA GAA GAC ATT GTA AGC ATT ATT AAG AGA AGC AGA AGA           96
Gly Val Tyr Ala Glu Asp Ile Val Ser Ile Ile Lys Arg Ser Arg Arg
                 20                  25                  30

GGA ATA TTT ATC TTA ACC CCC AAC TAT GTC AAT GGA CCC AGT ATC TTT          144
Gly Ile Phe Ile Leu Thr Pro Asn Tyr Val Asn Gly Pro Ser Ile Phe
             35                  40                  45

GAA CTA CAA GCA GCA GTG AAT CTT GCC TTG GAT GAT CAA ACA CTG AAA          192
Glu Leu Gln Ala Ala Val Asn Leu Ala Leu Asp Asp Gln Thr Leu Lys
 50                  55                  60

CTC ATT TTA ATT AAG TTC TGT TAC TTC CAA GAG CCA GAG TCT CTA CCT          240
Leu Ile Leu Ile Lys Phe Cys Tyr Phe Gln Glu Pro Glu Ser Leu Pro
 65                  70                  75                  80

CAT CTS GTG AAA AAA GCT CTC AGG GTT TTG CCC ACA GTT ACT TGG AGA          288
His Leu Val Lys Lys Ala Leu Arg Val Leu Pro Thr Val Thr Trp Arg
                 85                  90                  95

GGC TTA AAA TCA GTT CCT CCC AAT TCT AGG TTY TGG GCC AAA ATG CGY          336
Gly Leu Lys Ser Val Pro Pro Asn Ser Arg Phe Trp Ala Lys Met Arg
                100                 105                 110

TAC CAC ATG CCT GTG AAA AAT CTY TCA GGG ATT CAC GTG GGA ACC AGC          384
Tyr His Met Pro Val Lys Asn Leu Ser Gly Ile His Val Gly Thr Ser
            115                 120                 125

TCC AGA ATT ACC TCT AGG GAT TTT TTC AGT GGA AAG GAY TCM GTA GAA          432
Ser Arg Ile Thr Ser Arg Asp Phe Phe Ser Gly Lys Asp Ser Val Glu
130                 135                 140

CAG AAA CCA TGG GGA GGA GCT CCC AGN CTN AAG GGA NGG TGN AAT GAG          480
```

```
Gln Lys Pro Trp Gly Gly Ala Pro Ser Leu Lys Gly Arg Cys Asn Glu
145                 150                 155                 160

CC                                                                      482

(2) INFORMATION FOR SEQ ID NO:6:

(i) SEQUENCE CHARACTERISTICS:
        (A) LENGTH: 160 amino acids
        (B) TYPE: amino acid
        (D) TOPOLOGY: linear (ii) MOLECULE TYPE: protein (xi) SEQUENCE DESCRIPTION: SEQ ID NO:6:

Lys Tyr Gly Tyr Ser Leu Phe Phe Leu Glu Arg Asn Val Ala Pro Gly
1               5                   10                  15

Gly Val Tyr Ala Glu Asp Ile Val Ser Ile Ile Lys Arg Ser Arg Arg
                20                  25                  30

Gly Ile Phe Ile Leu Thr Pro Asn Tyr Val Asn Gly Pro Ser Ile Phe
            35                  40                  45

Glu Leu Gln Ala Ala Val Asn Leu Ala Leu Asp Asp Gln Thr Leu Lys
50                  55                  60

Leu Ile Leu Ile Lys Phe Cys Tyr Phe Gln Glu Pro Glu Ser Leu Pro
65                  70                  75                  80

His Leu Val Lys Lys Ala Leu Arg Val Leu Pro Thr Val Thr Trp Arg
                85                  90                  95

Gly Leu Lys Ser Val Pro Pro Asn Ser Arg Phe Trp Ala Lys Met Arg
            100                 105                 110

Tyr His Met Pro Val Lys Asn Leu Ser Gly Ile His Val Gly Thr Ser
        115                 120                 125

Ser Arg Ile Thr Ser Arg Asp Phe Phe Ser Gly Lys Asp Ser Val Glu
130                 135                 140

Gln Lys Pro Trp Gly Gly Ala Pro Ser Leu Lys Gly Arg Cys Asn Glu
145                 150                 155                 160

(2) INFORMATION FOR SEQ ID NO:7:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1401

(xi) SEQUENCE DESCRIPTION: SEQ ID NO:7:

TTT CCT AGG AGC CCC TAT GAT GTA GCC TGT TGT GTC AAG ATG ATT TTA        48
Phe Pro Arg Ser Pro Tyr Asp Val Ala Cys Cys Val Lys Met Ile Leu
1               5                   10                  15

GAA GTT AAG CCC CAG ACA AAT GCA TCC TGT GAG TAT TCC GCA TCA CAT        96
Glu Val Lys Pro Gln Thr Asn Ala Ser Cys Glu Tyr Ser Ala Ser His
                20                  25                  30

AAG CAA GAC CTA CTT CTT GGG AGC ACT GGC TCT ATT TCT TGC CCC AGT       144
Lys Gln Asp Leu Leu Leu Gly Ser Thr Gly Ser Ile Ser Cys Pro Ser
            35                  40                  45

CTC AGC TGC CAA AGT GAT GCA CAA AGT CCA GCG GTA ACC TGG TAC AAG       192
Leu Ser Cys Gln Ser Asp Ala Gln Ser Pro Ala Val Thr Trp Tyr Lys
50                  55                  60
```

```
AAT GGA AAA CTC CTC TCT GTG GAA AGG AGC AAC CGA ATC GTA GTG GAT        240
Asn Gly Lys Leu Leu Ser Val Glu Arg Ser Asn Arg Ile Val Val Asp
 65              70                  75                  80

GAA GTT TAT GAC TAT CAC CAG GGC ACA TAT GTA TGT GAT TAC ACT CAG        288
Glu Val Tyr Asp Tyr His Gln Gly Thr Tyr Val Cys Asp Tyr Thr Gln
                    85                  90                  95

TCG GAT ACT GTG AGT TCG TGG ACA GTC AGA GCT GTT GTT CAA GTG AGA        336
Ser Asp Thr Val Ser Ser Trp Thr Val Arg Ala Val Val Gln Val Arg
                100                 105                 110

ACC ATT GTG GGA GAC ACT AAA CTC AAA CCA GAT ATT CTG GAT CCT GTC        384
Thr Ile Val Gly Asp Thr Lys Leu Lys Pro Asp Ile Leu Asp Pro Val
            115                 120                 125

GAG GAC ACA CTG GAA GTA GAA CTT GGA AAG CCT TTA ACT ATT AGC TGC        432
Glu Asp Thr Leu Glu Val Glu Leu Gly Lys Pro Leu Thr Ile Ser Cys
        130                 135                 140

AAA GCA CGA TTT GGC TTT GAA AGG GTC TTT AAC CCT GTC ATA AAA TGG        480
Lys Ala Arg Phe Gly Phe Glu Arg Val Phe Asn Pro Val Ile Lys Trp
145                 150                 155                 160

TAC ATC AAA GAT TCT GAC CTA GAG TGG GAA GTC TCA GTA CCT GAG GCG        528
Tyr Ile Lys Asp Ser Asp Leu Glu Trp Glu Val Ser Val Pro Glu Ala
                165                 170                 175

AAA AGT ATT AAA TCC ACT TTA AAG GAT GAA ATC ATT GAG CGT AAT ATC        576
Lys Ser Ile Lys Ser Thr Leu Lys Asp Glu Ile Ile Glu Arg Asn Ile
            180                 185                 190

ATC TTG GAA AAA GTC ACT CAG CGT GAT CTT CGC AGG AAG TTT GTT TGC        624
Ile Leu Glu Lys Val Thr Gln Arg Asp Leu Arg Arg Lys Phe Val Cys
        195                 200                 205

TTT GTC CAG AAC TCC ATT GGA AAC ACA ACC CAG TCC GTC CAA CTG AAA        672
Phe Val Gln Asn Ser Ile Gly Asn Thr Thr Gln Ser Val Gln Leu Lys
    210                 215                 220

GAA AAG AGA GGA GTG GTG CTC CTG TAC ATC CTG CTT GGC ACC ATC GGG        720
Glu Lys Arg Gly Val Val Leu Leu Tyr Ile Leu Leu Gly Thr Ile Gly
225                 230                 235                 240

ACC CTG GTG GCC GTG CTG GCG GCG AGT GCC CTC CTC TAC AGG CAC TGG        768
Thr Leu Val Ala Val Leu Ala Ala Ser Ala Leu Leu Tyr Arg His Trp
                245                 250                 255

ATT GAA ATA GTG CTG CTG TAC CGG ACC TAC CAG AGC AAG GAT CAG ACG        816
Ile Glu Ile Val Leu Leu Tyr Arg Thr Tyr Gln Ser Lys Asp Gln Thr
            260                 265                 270

CTT GGG GAT AAA AAG GAT TTT GAT GCT TTC GTA TCC TAT GCA AAA TGG        864
Leu Gly Asp Lys Lys Asp Phe Asp Ala Phe Val Ser Tyr Ala Lys Trp
        275                 280                 285

AGC TCT TTT CCA AGT GAG GCC ACT TCA TCT CTG AGT GAA GAA CAC TTG        912
Ser Ser Phe Pro Ser Glu Ala Thr Ser Ser Leu Ser Glu Glu His Leu
    290                 295                 300

GCC CTG AGC CTA TTT CCT GAT GTT TTA GAA AAC AAA TAT GGA TAT AGC        960
Ala Leu Ser Leu Phe Pro Asp Val Leu Glu Asn Lys Tyr Gly Tyr Ser
305                 310                 315                 320

CTG TGT TTG CTT GAA AGA GAT GTG GCT CCA GGA GGA GTG TAT GCA GAA       1008
Leu Cys Leu Leu Glu Arg Asp Val Ala Pro Gly Gly Val Tyr Ala Glu
                325                 330                 335

GAC ATT GTG AGC ATT ATT AAG AGA AGC AGA GAG GTA ATA TTT ATC TTG       1056
Asp Ile Val Ser Ile Ile Lys Arg Ser Arg Glu Val Ile Phe Ile Leu
            340                 345                 350

AGC CCC AAC TAT GTC AAT GGA CCC AGT ATC TTT GAA CTA CAA GCA GCA       1104
Ser Pro Asn Tyr Val Asn Gly Pro Ser Ile Phe Glu Leu Gln Ala Ala
        355                 360                 365

GTG AAT CTT GCC TTG GAT GAT CAA ACA CTG AAA CTC ATT TTA ATT AAG       1152
Val Asn Leu Ala Leu Asp Asp Gln Thr Leu Lys Leu Ile Leu Ile Lys
```

```
                370                375                380
TTC TGT TAC TTC CAA GAG CCA GAG TCT CTA CCT CAT CTC GTG AAA AAA    1200
Phe Cys Tyr Phe Gln Glu Pro Glu Ser Leu Pro His Leu Val Lys Lys
385                390                395                400

GCT CTC AGG GTT TTG CCC ACA GTT ACT TGG AGA GGC TTA AAA TCA GTT    1248
Ala Leu Arg Val Leu Pro Thr Val Thr Trp Arg Gly Leu Lys Ser Val
                405                410                415

CCT CCC AAT TCT AGG TTC TGG GCC AAA ATG CGC TAC CAC ATG CCT GTG    1296
Pro Pro Asn Ser Arg Phe Trp Ala Lys Met Arg Tyr His Met Pro Val
                420                425                430

AAA AAC TCT CAG GGA TTC ACG TGG AAC CAG CTC AGA ATT ACC TCT AGG    1344
Lys Asn Ser Gln Gly Phe Thr Trp Asn Gln Leu Arg Ile Thr Ser Arg
                435                440                445

ATT TTT CAG TGG AAA GGA CTC AGT AGA ACA GAA ACC ACT GGG GAG GAG    1392
Ile Phe Gln Trp Lys Gly Leu Ser Arg Thr Glu Thr Thr Gly Glu Glu
450                455                460

CTC CCA GCC TAA                                                    1404
Leu Pro Ala
465

(2) INFORMATION FOR SEQ ID NO:8:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:8:

Phe Pro Arg Ser Pro Tyr Asp Val Ala Cys Cys Val Lys Met Ile Leu
1               5                   10                  15

Glu Val Lys Pro Gln Thr Asn Ala Ser Cys Glu Tyr Ser Ala Ser His
            20                  25                  30

Lys Gln Asp Leu Leu Gly Ser Thr Gly Ser Ile Ser Cys Pro Ser
        35                  40                  45

Leu Ser Cys Gln Ser Asp Ala Gln Ser Pro Ala Val Thr Trp Tyr Lys
    50                  55                  60

Asn Gly Lys Leu Leu Ser Val Glu Arg Ser Asn Arg Ile Val Val Asp
65                  70                  75                  80

Glu Val Tyr Asp Tyr His Gln Gly Thr Tyr Val Cys Asp Tyr Thr Gln
                85                  90                  95

Ser Asp Thr Val Ser Ser Trp Thr Val Arg Ala Val Val Gln Val Arg
            100                 105                 110

Thr Ile Val Gly Asp Thr Lys Leu Lys Pro Asp Ile Leu Asp Pro Val
        115                 120                 125

Glu Asp Thr Leu Glu Val Glu Leu Gly Lys Pro Leu Thr Ile Ser Cys
130                 135                 140

Lys Ala Arg Phe Gly Phe Glu Arg Val Phe Asn Pro Val Ile Lys Trp
145                 150                 155                 160

Tyr Ile Lys Asp Ser Asp Leu Glu Trp Glu Val Ser Val Pro Glu Ala
                165                 170                 175

Lys Ser Ile Lys Ser Thr Leu Lys Asp Glu Ile Ile Glu Arg Asn Ile
            180                 185                 190

Ile Leu Glu Lys Val Thr Gln Arg Asp Leu Arg Arg Lys Phe Val Cys
        195                 200                 205

Phe Val Gln Asn Ser Ile Gly Asn Thr Thr Gln Ser Val Gln Leu Lys
210                 215                 220
```

```
Glu Lys Arg Gly Val Val Leu Leu Tyr Ile Leu Leu Gly Thr Ile Gly
225                 230                 235                 240

Thr Leu Val Ala Val Leu Ala Ala Ser Ala Leu Leu Tyr Arg His Trp
            245                 250                 255

Ile Glu Ile Val Leu Leu Tyr Arg Thr Tyr Gln Ser Lys Asp Gln Thr
            260                 265                 270

Leu Gly Asp Lys Lys Asp Phe Asp Ala Phe Val Ser Tyr Ala Lys Trp
            275                 280                 285

Ser Ser Phe Pro Ser Glu Ala Thr Ser Ser Leu Ser Glu Glu His Leu
290                 295                 300

Ala Leu Ser Leu Phe Pro Asp Val Leu Glu Asn Lys Tyr Gly Tyr Ser
305                 310                 315                 320

Leu Cys Leu Leu Glu Arg Asp Val Ala Pro Gly Gly Val Tyr Ala Glu
            325                 330                 335

Asp Ile Val Ser Ile Ile Lys Arg Ser Arg Glu Val Ile Phe Ile Leu
            340                 345                 350

Ser Pro Asn Tyr Val Asn Gly Pro Ser Ile Phe Glu Leu Gln Ala Ala
            355                 360                 365

Val Asn Leu Ala Leu Asp Asp Gln Thr Leu Lys Leu Ile Leu Ile Lys
370                 375                 380

Phe Cys Tyr Phe Gln Glu Pro Glu Ser Leu Pro His Leu Val Lys Lys
385                 390                 395                 400

Ala Leu Arg Val Leu Pro Thr Val Thr Trp Arg Gly Leu Lys Ser Val
            405                 410                 415

Pro Pro Asn Ser Arg Phe Trp Ala Lys Met Arg Tyr His Met Pro Val
            420                 425                 430

Lys Asn Ser Gln Gly Phe Thr Trp Asn Gln Leu Arg Ile Thr Ser Arg
            435                 440                 445

Ile Phe Gln Trp Lys Gly Leu Ser Arg Thr Glu Thr Thr Gly Glu Glu
450                 455                 460

Leu Pro Ala
465

(2) INFORMATION FOR SEQ ID NO:9:

(i) SEQUENCE CHARACTERISTICS:
        (A) LENGTH: 2314 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 109..1905

(xi) SEQUENCE DESCRIPTION: SEQ ID NO:9:

CCAGCGTGGT GGAATTCGGA TACTCAGGGC AGAGTTCTGA ATCTCAAAAC ACTTTAATCT      60

GGCAAAGGAA TGAAGTTATT GGAGTGATGA CAGGAACACG GGAGAACA ATG CTC TGT      117
                                                    Met Leu Cys
                                                      1

TTG GGC TGG ATA TTT CTT TGG CTT GTT GCA GGA GAG CGA ATT AAA GGA       165
Leu Gly Trp Ile Phe Leu Trp Leu Val Ala Gly Glu Arg Ile Lys Gly
    5               10                  15

TTT AAT ATT TCA GGT TGT TCC ACA AAA AAA CTC CTT TGG ACA TAT TCT       213
Phe Asn Ile Ser Gly Cys Ser Thr Lys Lys Leu Leu Trp Thr Tyr Ser
 20              25                  30                  35
```

```
ACA AGG AGT GAA GAG GAA TTT GTC TTA TTT TGT GAT TTA CCA GAG CCA      261
Thr Arg Ser Glu Glu Glu Phe Val Leu Phe Cys Asp Leu Pro Glu Pro
         40                      45                      50

CAG AAA TCA CAT TTC TGC CAC AGA AAT CGA CTC TCA CCA AAA CAA GTC      309
Gln Lys Ser His Phe Cys His Arg Asn Arg Leu Ser Pro Lys Gln Val
             55                      60                      65

CCT GAG CAC CTG CCC TTC ATG GGT AGT AAC GAC CTA TCT GAT GTC CAA      357
Pro Glu His Leu Pro Phe Met Gly Ser Asn Asp Leu Ser Asp Val Gln
                 70                      75                      80

TGG TAC CAA CAA CCT TCG AAT GGA GAT CCA TTA GAG GAC ATT AGG AAA      405
Trp Tyr Gln Gln Pro Ser Asn Gly Asp Pro Leu Glu Asp Ile Arg Lys
             85                      90                      95

AGC TAT CCT CAC ATC ATT CAG GAC AAA TGT ACC CTT CAC TTT TTG ACC      453
Ser Tyr Pro His Ile Ile Gln Asp Lys Cys Thr Leu His Phe Leu Thr
100                     105                     110                     115

CCA GGG GTG AAT AAT TCT GGG TCA TAT ATT TGT AGA CCC AAG ATG ATT      501
Pro Gly Val Asn Asn Ser Gly Ser Tyr Ile Cys Arg Pro Lys Met Ile
                    120                     125                     130

AAG AGC CCC TAT GAT GTA GCC TGT TGT GTC AAG ATG ATT TTA GAA GTT      549
Lys Ser Pro Tyr Asp Val Ala Cys Cys Val Lys Met Ile Leu Glu Val
                135                     140                     145

AAG CCC CAG ACA AAT GCA TCC TGT GAG TAT TCC GCA TCA CAT AAG CAA      597
Lys Pro Gln Thr Asn Ala Ser Cys Glu Tyr Ser Ala Ser His Lys Gln
            150                     155                     160

GAC CTA CTT CTT GGG AGC ACT GGC TCT ATT TCT TGC CCC AGT CTC AGC      645
Asp Leu Leu Leu Gly Ser Thr Gly Ser Ile Ser Cys Pro Ser Leu Ser
        165                     170                     175

TGC CAA AGT GAT GCA CAA AGT CCA GCG GTA ACC TGG TAC AAG AAT GGA      693
Cys Gln Ser Asp Ala Gln Ser Pro Ala Val Thr Trp Tyr Lys Asn Gly
180                     185                     190                     195

AAA CTC CTC TCT GTG GAA AGG AGC AAC CGA ATC GTA GTG GAT GAA GTT      741
Lys Leu Leu Ser Val Glu Arg Ser Asn Arg Ile Val Val Asp Glu Val
                    200                     205                     210

TAT GAC TAT CAC CAG GGC ACA TAT GTA TGT GAT TAC ACT CAG TCG GAT      789
Tyr Asp Tyr His Gln Gly Thr Tyr Val Cys Asp Tyr Thr Gln Ser Asp
                215                     220                     225

ACT GTG AGT TCG TGG ACA GTC AGA GCT GTT GTT CAA GTG AGA ACC ATT      837
Thr Val Ser Ser Trp Thr Val Arg Ala Val Val Gln Val Arg Thr Ile
            230                     235                     240

GTG GGA GAC ACT AAA CTC AAA CCA GAT ATT CTG GAT CCT GTC GAG GAC      885
Val Gly Asp Thr Lys Leu Lys Pro Asp Ile Leu Asp Pro Val Glu Asp
        245                     250                     255

ACA CTG GAA GTA GAA CTT GGA AAG CCT TTA ACT ATT AGC TGC AAA GCA      933
Thr Leu Glu Val Glu Leu Gly Lys Pro Leu Thr Ile Ser Cys Lys Ala
260                     265                     270                     275

CGA TTT GGC TTT GAA AGG GTC TTT AAC CCT GTC ATA AAA TGG TAC ATC      981
Arg Phe Gly Phe Glu Arg Val Phe Asn Pro Val Ile Lys Trp Tyr Ile
                    280                     285                     290

AAA GAT TCT GAC CTA GAG TGG GAA GTC TCA GTA CCT GAG GCG AAA AGT     1029
Lys Asp Ser Asp Leu Glu Trp Glu Val Ser Val Pro Glu Ala Lys Ser
                295                     300                     305

ATT AAA TCC ACT TTA AAG GAT GAA ATC ATT GAG CGT AAT ATC ATC TTG     1077
Ile Lys Ser Thr Leu Lys Asp Glu Ile Ile Glu Arg Asn Ile Ile Leu
            310                     315                     320

GAA AAA GTC ACT CAG CGT GAT CTT CGC AGG AAG TTT GTT TGC TTT GTC     1125
Glu Lys Val Thr Gln Arg Asp Leu Arg Arg Lys Phe Val Cys Phe Val
        325                     330                     335

CAG AAC TCC ATT GGA AAC ACA ACC CAG TCC GTC CAA CTG AAA GAA AAG     1173
Gln Asn Ser Ile Gly Asn Thr Thr Gln Ser Val Gln Leu Lys Glu Lys
```

```
     340              345              350              355
AGA GGA GTG GTG CTC CTG TAC ATC CTG CTT GGC ACC ATC GGG ACC CTG    1221
Arg Gly Val Val Leu Leu Tyr Ile Leu Leu Gly Thr Ile Gly Thr Leu
                     360              365              370

GTG GCC GTG CTG GCG GCG AGT GCC CTC CTC TAC AGG CAC TGG ATT GAA    1269
Val Ala Val Leu Ala Ala Ser Ala Leu Leu Tyr Arg His Trp Ile Glu
                 375              380              385

ATA GTG CTG CTG TAC CGG ACC TAC CAG AGC AAG GAT CAG ACG CTT GGG    1317
Ile Val Leu Leu Tyr Arg Thr Tyr Gln Ser Lys Asp Gln Thr Leu Gly
             390              395              400

GAT AAA AAG GAT TTT GAT GCT TTC GTA TCC TAT GCA AAA TGG AGC TCT    1365
Asp Lys Lys Asp Phe Asp Ala Phe Val Ser Tyr Ala Lys Trp Ser Ser
    405              410              415

TTT CCA AGT GAG GCC ACT TCA TCT CTG AGT GAA GAA CAC TTG GCC CTG    1413
Phe Pro Ser Glu Ala Thr Ser Ser Leu Ser Glu Glu His Leu Ala Leu
420              425              430              435

AGC CTA TTT CCT GAT GTT TTA GAA AAC AAA TAT GGA TAT AGC CTG TGT    1461
Ser Leu Phe Pro Asp Val Leu Glu Asn Lys Tyr Gly Tyr Ser Leu Cys
                 440              445              450

TTG CTT GAA AGA GAT GTG GCT CCA GGA GGA GTG TAT GCA GAA GAC ATT    1509
Leu Leu Glu Arg Asp Val Ala Pro Gly Gly Val Tyr Ala Glu Asp Ile
             455              460              465

GTG AGC ATT ATT AAG AGA AGC AGA AGA GGA ATA TTT ATC TTG AGC CCC    1557
Val Ser Ile Ile Lys Arg Ser Arg Arg Gly Ile Phe Ile Leu Ser Pro
         470              475              480

AAC TAT GTC AAT GGA CCC AGT ATC TTT GAA CTA CAA GCA GCA GTG AAT    1605
Asn Tyr Val Asn Gly Pro Ser Ile Phe Glu Leu Gln Ala Ala Val Asn
    485              490              495

CTT GCC TTG GAT GAT CAA ACA CTG AAA CTC ATT TTA ATT AAG TTC TGT    1653
Leu Ala Leu Asp Asp Gln Thr Leu Lys Leu Ile Leu Ile Lys Phe Cys
500              505              510              515

TAC TTC CAA GAG CCA GAG TCT CTA CCT CAT CTC GTG AAA AAA GCT CTC    1701
Tyr Phe Gln Glu Pro Glu Ser Leu Pro His Leu Val Lys Lys Ala Leu
                 520              525              530

AGG GTT TTG CCC ACA GTT ACT TGG AGA GGC TTA AAA TCA GTT CCT CCC    1749
Arg Val Leu Pro Thr Val Thr Trp Arg Gly Leu Lys Ser Val Pro Pro
             535              540              545

AAT TCT AGG TTC TGG GCC AAA ATG CGC TAC CAC ATG CCT GTG AAA AAC    1797
Asn Ser Arg Phe Trp Ala Lys Met Arg Tyr His Met Pro Val Lys Asn
         550              555              560

TCT CAG GGA TTC ACG TGG AAC CAG CTC AGA ATT ACC TCT AGG ATT TTT    1845
Ser Gln Gly Phe Thr Trp Asn Gln Leu Arg Ile Thr Ser Arg Ile Phe
    565              570              575

CAG TGG AAA GGA CTC AGT AGA ACA GAA ACC ACT GGG AGG AGC TCC CAG    1893
Gln Trp Lys Gly Leu Ser Arg Thr Glu Thr Thr Gly Arg Ser Ser Gln
580              585              590              595

CCT AAG GAA TGG TGAAATGAGC CCTGGAGCCC CCTCCAGTCC AGTCCCTGGG        1945
Pro Lys Glu Trp
ATAGAGATGT TGCTGGACAG AACTCACAGC TCTGTGTGTG TGTGTTCAGG CTGATAGGAA  2005

ATTCAAAGAG TCTCCTGCCA GCACCAAGCA AGCTTGATGG ACAATGGAAT GGGATTGAGA  2065

CTGTGGTTTA GAGCCTTTGA TTTCCTGGAC TGGACAGACG GCGAGTGAAT TCTCTAGACC  2125

TTGGGTACTT TCAGTACACA ACACCCCTAA GATTTCCCAG TGGTCCGAGC AGAATCAGAA  2185

AATACAGCTA CTTCTGCCTT ATGGCTAGGG AACTGTCATG TCTACCATGT ATTGTACATA  2245

TGACTTTATG TATACTTGCA ATCAAATAAA TATTATTTTA TTAGAAAAAA AAAAAAAAG   2305

GGCGGCCGC                                                          2314
```

-continued (2) INFORMATION FOR SEQ ID NO:10:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:10:

```
Met Leu Cys Leu Gly Trp Ile Phe Leu Trp Leu Val Ala Gly Glu Arg
 1               5                  10                  15

Ile Lys Gly Phe Asn Ile Ser Gly Cys Ser Thr Lys Lys Leu Leu Trp
                20                  25                  30

Thr Tyr Ser Thr Arg Ser Glu Glu Phe Val Leu Phe Cys Asp Leu
            35                  40                  45

Pro Glu Pro Gln Lys Ser His Phe Cys His Arg Asn Arg Leu Ser Pro
        50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365
```

```
Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
                420                 425                 430

Leu Ala Leu Ser Leu Phe Pro Asp Val Leu Glu Asn Lys Tyr Gly Tyr
            435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
    530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
            580                 585                 590

Ser Ser Gln Pro Lys Glu Trp
        595
```

(2) INFORMATION FOR SEQ ID NO:11:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..360

(xi) SEQUENCE DESCRIPTION: SEQ ID NO:11:

```
GCA GCA GTG AAT CTT GCC TTG GTT GAT CAG ACA CTG AAG TTG ATT TTA      48
Ala Ala Val Asn Leu Ala Leu Val Asp Gln Thr Leu Lys Leu Ile Leu
1               5                   10                  15

ATT AAG TTC TGT TCC TTC CAA GAG CCA GAA TCT CTT CCT TAC CTT GTC      96
Ile Lys Phe Cys Ser Phe Gln Glu Pro Glu Ser Leu Pro Tyr Leu Val
                20                  25                  30

AAA AAG GCT CTG CGG GTT CTC CCC ACA GTC ACA TGG AAA GGC TTG AAG     144
Lys Lys Ala Leu Arg Val Leu Pro Thr Val Thr Trp Lys Gly Leu Lys
            35                  40                  45

TCG GTC CAC GCC AGT TCC AGG TTC TGG ACC CAA ATT CGT TAC CAC ATG     192
Ser Val His Ala Ser Ser Arg Phe Trp Thr Gln Ile Arg Tyr His Met
        50                  55                  60
```

```
CCT GTG AAG AAC TCC AAC AGG TTT ATG TTC AAC GGG CTC AGA ATT TTC         240
Pro Val Lys Asn Ser Asn Arg Phe Met Phe Asn Gly Leu Arg Ile Phe
 65                  70                  75                  80

CTG AAG GGC TTT TCC CCT GAA AAG GAC CTA GTG ACA CAG AAA CCC CTG         288
Leu Lys Gly Phe Ser Pro Glu Lys Asp Leu Val Thr Gln Lys Pro Leu
                     85                  90                  95

GAA GGA ATG CCC AAG TCT GGG AAT GAC CAC GGA GCT CAG AAC CTC CTT         336
Glu Gly Met Pro Lys Ser Gly Asn Asp His Gly Ala Gln Asn Leu Leu
                100                 105                 110

CTC TAC AGT GAC CAG AAG AGG TGC TGATGGGTAG AACTTGCTGT GTGGATCAGG        390
Leu Tyr Ser Asp Gln Lys Arg Cys
            115                 120

CTGATAGAAA TTGAGCCTTT CTGCTCTCAG TGCCAAGCAA GCTTGACAGG CAGTGGAATG       450

AAGCGGCATC TGTGGTTTTA GGGTCTGGGT TCCTGGAACA GACACAGAGC AATACTCCAG       510

ACCTCTGCCG TGTGCTTAGC ACACATTTCC CTGAGAGTTC CCAAGTAGCC TGAACAGAAT       570

CAACAGAAAT AGCTCCATGG GCTGTCCAAC ATTCATGCAC GCATGCCTGT TTTGCACTAT       630

ATATATGAAT TTATCATACG TTTGTGTGTG TATATGCATT CAGATAAATA GGATTTTATT       690

TTGTTCGATA CGAGTGATTG AAACTCCATT TAAAGCCCTT CTGTAAAGAA ATTTTGCTGC       750

AAAAAAAAAA AAAAAAA                                                     768

(2) INFORMATION FOR SEQ ID NO:12:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:12:

Ala Ala Val Asn Leu Ala Leu Val Asp Gln Thr Leu Lys Leu Ile Leu
  1               5                  10                  15

Ile Lys Phe Cys Ser Phe Gln Glu Pro Glu Ser Leu Pro Tyr Leu Val
                 20                  25                  30

Lys Lys Ala Leu Arg Val Leu Pro Thr Val Thr Trp Lys Gly Leu Lys
             35                  40                  45

Ser Val His Ala Ser Ser Arg Phe Trp Thr Gln Ile Arg Tyr His Met
 50                  55                  60

Pro Val Lys Asn Ser Asn Arg Phe Met Phe Asn Gly Leu Arg Ile Phe
 65                  70                  75                  80

Leu Lys Gly Phe Ser Pro Glu Lys Asp Leu Val Thr Gln Lys Pro Leu
                     85                  90                  95

Glu Gly Met Pro Lys Ser Gly Asn Asp His Gly Ala Gln Asn Leu Leu
                100                 105                 110

Leu Tyr Ser Asp Gln Lys Arg Cys
            115                 120

(2) INFORMATION FOR SEQ ID NO:13:

(i) SEQUENCE CHARACTERISTICS:
        (A) LENGTH: 1833 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 1..1830

(ix) FEATURE:
        (A) NAME/KEY: mat_peptide
        (B) LOCATION: 52..1830

(xi) SEQUENCE DESCRIPTION: SEQ ID NO:13:

```
ATG TCT GTT TGG CTG GTG TTC TTG GTT TGT GCA GGA GAG AAG ACC ACA        48
Met Ser Val Trp Leu Val Phe Leu Val Cys Ala Gly Glu Lys Thr Thr
-17     -15             -10                 -5

GGA TTT AAT CAT TCA GCT TGT GCC ACC AAA AAT TCT GTG GAC ATA TTC        96
Gly Phe Asn His Ser Ala Cys Ala Thr Lys Asn Ser Val Asp Ile Phe
         1           5                  10                  15

GCA AGG GGT GCA GAG AAT TTT GTC TAT TTT GTG ACT TAC AAG AGC TTC       144
Ala Arg Gly Ala Glu Asn Phe Val Tyr Phe Val Thr Tyr Lys Ser Phe
                20              25                  30

AGG AGC AAA AAT TCT CCC ATG CAA GTC AAC TGT CAC CAA CAC AAA GTC       192
Arg Ser Lys Asn Ser Pro Met Gln Val Asn Cys His Gln His Lys Val
            35              40                  45

TGC TCA CAA ACT TGC AGT GGC AGT CAG AAG GAC TTA TCT GAT GTC CAG       240
Cys Ser Gln Thr Cys Ser Gly Ser Gln Lys Asp Leu Ser Asp Val Gln
        50              55                  60

TGG TAC ATG CAA CCT CGG AGT GGA AGT CCA CTA GAG GAG ATC AGT AGA       288
Trp Tyr Met Gln Pro Arg Ser Gly Ser Pro Leu Glu Glu Ile Ser Arg
    65              70                  75

AAC TCT CCC CAT ATG CAG AGT GAA GGC ATG CTG CAT ATA TTG GCC CCA       336
Asn Ser Pro His Met Gln Ser Glu Gly Met Leu His Ile Leu Ala Pro
80              85                  90                  95

CAG ACG AAC AGC ATT TGG TCA TAT ATT TGT AGA CCC AGA ATT AGG AGC       384
Gln Thr Asn Ser Ile Trp Ser Tyr Ile Cys Arg Pro Arg Ile Arg Ser
            100                 105                 110

CCC CAG GAT ATG GCC TGT TGT ATC AAG ACA GTC TTA GAA GTT AAG CCT       432
Pro Gln Asp Met Ala Cys Cys Ile Lys Thr Val Leu Glu Val Lys Pro
        115                 120                 125

CAG AGA AAC GTG TCC TGT GGG AAC ACA GCA CAA GAT GAA CAA GTC CTA       480
Gln Arg Asn Val Ser Cys Gly Asn Thr Ala Gln Asp Glu Gln Val Leu
    130                 135                 140

CTT CTT GGC AGT ACT GGC TCC ATT CAT TGT CCC AGT CTC AGC TGC CAA       528
Leu Leu Gly Ser Thr Gly Ser Ile His Cys Pro Ser Leu Ser Cys Gln
145                 150                 155

AGT GAT GTA CAG AGT CCA GAG ATG ACC TGG TAC AAG GAT GGA AGA CTA       576
Ser Asp Val Gln Ser Pro Glu Met Thr Trp Tyr Lys Asp Gly Arg Leu
160                 165                 170                 175

CTT CCT GAG CAC AAG AAA AAT CCA ATT GAG ATG GCA GAT ATT TAT GTT       624
Leu Pro Glu His Lys Lys Asn Pro Ile Glu Met Ala Asp Ile Tyr Val
            180                 185                 190

TTT AAT CAA GGC TTG TAT GTA TGT GAT TAC ACA CAG TCA GAT AAT GTG       672
Phe Asn Gln Gly Leu Tyr Val Cys Asp Tyr Thr Gln Ser Asp Asn Val
        195                 200                 205

AGT TCC TGG ACA GTC CGA GCT GTG GTT AAA GTG AGA ACC ATT GGT AAG       720
Ser Ser Trp Thr Val Arg Ala Val Val Lys Val Arg Thr Ile Gly Lys
    210                 215                 220

GAC ATC AAT GTG AAG CCG GAA ATT CTG GAT CCC ATT ACA GAT ACA CTG       768
Asp Ile Asn Val Lys Pro Glu Ile Leu Asp Pro Ile Thr Asp Thr Leu
225                 230                 235

GAC GTA GAG CTT GGA AAG CCT TTA ACT CTC CCC TGC AGA GTA CAG TTT       816
Asp Val Glu Leu Gly Lys Pro Leu Thr Leu Pro Cys Arg Val Gln Phe
240                 245                 250                 255

GGC TTC CAA AGA CTT TCA AAG CCT GTG ATA AAG TGG TAT GTC AAA GAA       864
Gly Phe Gln Arg Leu Ser Lys Pro Val Ile Lys Trp Tyr Val Lys Glu
            260                 265                 270
```

-continued

| | | |
|---|---|---|
| TCT ACA CAG GAG TGG GAA ATG TCA GTA TTT GAG GAG AAA AGA ATT CAA<br>Ser Thr Gln Glu Trp Glu Met Ser Val Phe Glu Glu Lys Arg Ile Gln<br>               275                       280                       285 | 912 |
| TCC ACT TTC AAG AAT GAA GTC ATT GAA CGT ACC ATC TTC TTG AGA GAA<br>Ser Thr Phe Lys Asn Glu Val Ile Glu Arg Thr Ile Phe Leu Arg Glu<br>          290                   295                    300 | 960 |
| GTT ACC CAG AGA GAT CTC AGC AGA AAG TTT GTT TGC TTT GCC CAG AAC<br>Val Thr Gln Arg Asp Leu Ser Arg Lys Phe Val Cys Phe Ala Gln Asn<br>305                       310                    315 | 1008 |
| TCC ATT GGG AAC ACA ACA CGG ACC ATA CGG CTG AGG AAG AAG GAA GAG<br>Ser Ile Gly Asn Thr Thr Arg Thr Ile Arg Leu Arg Lys Lys Glu Glu<br>320                   325                  330               335 | 1056 |
| GTG GTG TTT GTA TAC ATC CTT CTC GGC ACG GCC TTG ATG CTG GTG GGC<br>Val Val Phe Val Tyr Ile Leu Leu Gly Thr Ala Leu Met Leu Val Gly<br>               340                   345                  350 | 1104 |
| GTT CTG GTG GCA GCT GCT TTC CTC TAC TGG TAC TGG ATT GAA GTT GTC<br>Val Leu Val Ala Ala Ala Phe Leu Tyr Trp Tyr Trp Ile Glu Val Val<br>                   355                   360             365 | 1152 |
| CTG CTC TGT CGA ACC TAC AAG AAC AAA GAT GAG ACT CTG GGG GAT AAG<br>Leu Leu Cys Arg Thr Tyr Lys Asn Lys Asp Glu Thr Leu Gly Asp Lys<br>         370                    375                  380 | 1200 |
| AAG GAA TTC GAT GCA TTT GTA TCC TAC TCG AAT TGG AGC TCT CCT GAG<br>Lys Glu Phe Asp Ala Phe Val Ser Tyr Ser Asn Trp Ser Ser Pro Glu<br>385                       390                    395 | 1248 |
| ACT GAC GCC GTG GGA TCT CTG AGT GAG GAA CAC CTG GCT CTG AAT CTT<br>Thr Asp Ala Val Gly Ser Leu Ser Glu Glu His Leu Ala Leu Asn Leu<br>400                       405                  410               415 | 1296 |
| TTC CCG GAA GTC CTA GAA GAC ACC TAT GGG TAC AGA TTG TGT TTG CTT<br>Phe Pro Glu Val Leu Glu Asp Thr Tyr Gly Tyr Arg Leu Cys Leu Leu<br>                   420                   425               430 | 1344 |
| GAC CGA GAT GTG ACC CCA GGA GGA GTG TAT GCA GAT GAC ATT GTG AGC<br>Asp Arg Asp Val Thr Pro Gly Gly Val Tyr Ala Asp Asp Ile Val Ser<br>             435                   440                  445 | 1392 |
| ATC ATT AAG AAA AGC CGA AGA GGA ATA TTT ATC CTG AGT CCC AGC TAC<br>Ile Ile Lys Lys Ser Arg Arg Gly Ile Phe Ile Leu Ser Pro Ser Tyr<br>         450                    455                  460 | 1440 |
| CTC AAT GGA CCC CGT GTC TTT GAG CTA CAA GCA GCA GTG AAT CTT GCC<br>Leu Asn Gly Pro Arg Val Phe Glu Leu Gln Ala Ala Val Asn Leu Ala<br>465                       470                  475 | 1488 |
| TTG GTT GAT CAG ACA CTG AAG TTG ATT TTA ATT AAG TTC TGT TCC TTC<br>Leu Val Asp Gln Thr Leu Lys Leu Ile Leu Ile Lys Phe Cys Ser Phe<br>480                       485                  490               495 | 1536 |
| CAA GAG CCA GAA TCT CTT CCT TAC CTT GTC AAA AAG GCT CTG CGG GTT<br>Gln Glu Pro Glu Ser Leu Pro Tyr Leu Val Lys Lys Ala Leu Arg Val<br>                   500                   505               510 | 1584 |
| CTC CCC ACA GTC ACA TGG AAA GGC TTG AAG TCG GTC CAC GCC AGT TCC<br>Leu Pro Thr Val Thr Trp Lys Gly Leu Lys Ser Val His Ala Ser Ser<br>             515                   520                  525 | 1632 |
| AGG TTC TGG ACC CAA ATT CGT TAC CAC ATG CCT GTG AAG AAC TCC AAC<br>Arg Phe Trp Thr Gln Ile Arg Tyr His Met Pro Val Lys Asn Ser Asn<br>         530                    535                  540 | 1680 |
| AGG TTT ATG TTC AAC GGG CTC AGA ATT TTC CTG AAG GGC TTT TCC CCT<br>Arg Phe Met Phe Asn Gly Leu Arg Ile Phe Leu Lys Gly Phe Ser Pro<br>545                       550                  555 | 1728 |
| GAA AAG GAC CTA GTG ACA CAG AAA CCC CTG GAA GGA ATG CCC AAG TCT<br>Glu Lys Asp Leu Val Thr Gln Lys Pro Leu Glu Gly Met Pro Lys Ser<br>560                       565                  570               575 | 1776 |
| GGG AAT GAC CAC GGA GCT CAG AAC CTC CTT CTC TAC AGT GAC CAG AAG<br>Gly Asn Asp His Gly Ala Gln Asn Leu Leu Leu Tyr Ser Asp Gln Lys | 1824 |

```
                          580                585               590
AGG TGC TGA                                                                          1833
Arg Cys (2) INFORMATION FOR SEQ ID NO:14:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:14:

Met Ser Val Trp Leu Val Phe Leu Val Cys Ala Gly Glu Lys Thr Thr
-17     -15              -10              -5

Gly Phe Asn His Ser Ala Cys Ala Thr Lys Asn Ser Val Asp Ile Phe
     1            5                10                      15

Ala Arg Gly Ala Glu Asn Phe Val Tyr Phe Val Thr Tyr Lys Ser Phe
              20                25                30

Arg Ser Lys Asn Ser Pro Met Gln Val Asn Cys His Gln His Lys Val
         35                40                45

Cys Ser Gln Thr Cys Ser Gly Ser Gln Lys Asp Leu Ser Asp Val Gln
     50                55                    60

Trp Tyr Met Gln Pro Arg Ser Gly Ser Pro Leu Glu Glu Ile Ser Arg
 65              70                    75

Asn Ser Pro His Met Gln Ser Glu Gly Met Leu His Ile Leu Ala Pro
80                85                90                      95

Gln Thr Asn Ser Ile Trp Ser Tyr Ile Cys Arg Pro Arg Ile Arg Ser
                100               105              110

Pro Gln Asp Met Ala Cys Cys Ile Lys Thr Val Leu Glu Val Lys Pro
             115              120              125

Gln Arg Asn Val Ser Cys Gly Asn Thr Ala Gln Asp Glu Gln Val Leu
         130              135              140

Leu Leu Gly Ser Thr Gly Ser Ile His Cys Pro Ser Leu Ser Cys Gln
     145              150              155

Ser Asp Val Gln Ser Pro Glu Met Thr Trp Tyr Lys Asp Gly Arg Leu
160              165              170                      175

Leu Pro Glu His Lys Lys Asn Pro Ile Glu Met Ala Asp Ile Tyr Val
             180              185              190

Phe Asn Gln Gly Leu Tyr Val Cys Asp Tyr Thr Gln Ser Asp Asn Val
             195              200              205

Ser Ser Trp Thr Val Arg Ala Val Val Lys Val Arg Thr Ile Gly Lys
         210              215              220

Asp Ile Asn Val Lys Pro Glu Ile Leu Asp Pro Ile Thr Asp Thr Leu
225              230              235

Asp Val Glu Leu Gly Lys Pro Leu Thr Leu Pro Cys Arg Val Gln Phe
240              245              250                      255

Gly Phe Gln Arg Leu Ser Lys Pro Val Ile Lys Trp Tyr Val Lys Glu
             260              265              270

Ser Thr Gln Glu Trp Glu Met Ser Val Phe Glu Lys Arg Ile Gln
             275              280              285

Ser Thr Phe Lys Asn Glu Val Ile Glu Arg Thr Ile Phe Leu Arg Glu
         290              295              300

Val Thr Gln Arg Asp Leu Ser Arg Lys Phe Val Cys Phe Ala Gln Asn
305              310              315
```

```
Ser Ile Gly Asn Thr Thr Arg Thr Ile Arg Leu Arg Lys Lys Glu Glu
320                 325                 330                 335

Val Val Phe Val Tyr Ile Leu Leu Gly Thr Ala Leu Met Leu Val Gly
                340                 345                 350

Val Leu Val Ala Ala Ala Phe Leu Tyr Trp Tyr Trp Ile Glu Val Val
            355                 360                 365

Leu Leu Cys Arg Thr Tyr Lys Asn Lys Asp Glu Thr Leu Gly Asp Lys
        370                 375                 380

Lys Glu Phe Asp Ala Phe Val Ser Tyr Ser Asn Trp Ser Ser Pro Glu
385                 390                 395

Thr Asp Ala Val Gly Ser Leu Ser Glu Glu His Leu Ala Leu Asn Leu
400                 405                 410                 415

Phe Pro Glu Val Leu Glu Asp Thr Tyr Gly Tyr Arg Leu Cys Leu Leu
                420                 425                 430

Asp Arg Asp Val Thr Pro Gly Gly Val Tyr Ala Asp Asp Ile Val Ser
            435                 440                 445

Ile Ile Lys Lys Ser Arg Arg Gly Ile Phe Ile Leu Ser Pro Ser Tyr
        450                 455                 460

Leu Asn Gly Pro Arg Val Phe Glu Leu Gln Ala Ala Val Asn Leu Ala
465                 470                 475

Leu Val Asp Gln Thr Leu Lys Leu Ile Leu Ile Lys Phe Cys Ser Phe
480                 485                 490                 495

Gln Glu Pro Glu Ser Leu Pro Tyr Leu Val Lys Lys Ala Leu Arg Val
                500                 505                 510

Leu Pro Thr Val Thr Trp Lys Gly Leu Lys Ser Val His Ala Ser Ser
            515                 520                 525

Arg Phe Trp Thr Gln Ile Arg Tyr His Met Pro Val Lys Asn Ser Asn
        530                 535                 540

Arg Phe Met Phe Asn Gly Leu Arg Ile Phe Leu Lys Gly Phe Ser Pro
        545                 550                 555

Glu Lys Asp Leu Val Thr Gln Lys Pro Leu Glu Gly Met Pro Lys Ser
560                 565                 570                 575

Gly Asn Asp His Gly Ala Gln Asn Leu Leu Leu Tyr Ser Asp Gln Lys
                580                 585                 590

Arg Cys (2) INFORMATION FOR SEQ ID NO:15:

(i) SEQUENCE CHARACTERISTICS:
        (A) LENGTH: 2259 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 22..1863

(xi) SEQUENCE DESCRIPTION: SEQ ID NO:15:

TGACAGGAGC AAAGGGGAAC C ATG CTC TGT TTG GGC TGG GTG TTT CTT TGG        51
                       Met Leu Cys Leu Gly Trp Val Phe Leu Trp
                        1               5                   10

TTT GTT GCA GGA GAG AAG ACC ACA GGA TTT AAT CAT TCA GCT TGT GCC       99
Phe Val Ala Gly Glu Lys Thr Thr Gly Phe Asn His Ser Ala Cys Ala
            15                  20                  25
```

-continued

```
ACC AAA AAA CTT CTG TGG ACA TAT TCT GCA AGG GGT GCA GAG AAT TTT     147
Thr Lys Lys Leu Leu Trp Thr Tyr Ser Ala Arg Gly Ala Glu Asn Phe
             30                  35                  40

GTC CTA TTT TGT GAC TTA CAA GAG CTT CAG GAG CAA AAA TTC TCC CAT     195
Val Leu Phe Cys Asp Leu Gln Glu Leu Gln Glu Gln Lys Phe Ser His
         45                  50                  55

GCA AGT CAA CTG TCA CCA ACA CAA AGT CCT GCT CAC AAA CCT TGC AGT     243
Ala Ser Gln Leu Ser Pro Thr Gln Ser Pro Ala His Lys Pro Cys Ser
     60                  65                  70

GGC AGT CAG AAG GAC CTA TCT GAT GTC CAG TGG TAC ATG CAA CCT CGG     291
Gly Ser Gln Lys Asp Leu Ser Asp Val Gln Trp Tyr Met Gln Pro Arg
 75                  80                  85                  90

AGT GGA AGT CCA CTA GAG GAG ATC AGT AGA AAC TCT CCC CAT ATG CAG     339
Ser Gly Ser Pro Leu Glu Glu Ile Ser Arg Asn Ser Pro His Met Gln
                 95                 100                 105

AGT GAA GGC ATG CTG CAT ATA TTG GCC CCA CAG ACG AAC AGC ATT TGG     387
Ser Glu Gly Met Leu His Ile Leu Ala Pro Gln Thr Asn Ser Ile Trp
             110                 115                 120

TCA TAT ATT TGT AGA CCC AGA ATT AGG AGC CCC CAG GAT ATG GCC TGT     435
Ser Tyr Ile Cys Arg Pro Arg Ile Arg Ser Pro Gln Asp Met Ala Cys
         125                 130                 135

TGT ATC AAG ACA GTC TTA GAA GTT AAG CCT CAG AGA AAC GTG TCC TGT     483
Cys Ile Lys Thr Val Leu Glu Val Lys Pro Gln Arg Asn Val Ser Cys
     140                 145                 150

GGG AAC ACA GCA CAA GAT GAA CAA GTC CTA CTT CTT GGC AGT ACT GGC     531
Gly Asn Thr Ala Gln Asp Glu Gln Val Leu Leu Leu Gly Ser Thr Gly
155                 160                 165                 170

TCC ATT CAT TGT CCC AGT CTC AGC TGC CAA AGT GAT GTA CAG AGT CCA     579
Ser Ile His Cys Pro Ser Leu Ser Cys Gln Ser Asp Val Gln Ser Pro
                 175                 180                 185

GAG ATG ACC TGG TAC AAG GAT GGA AGA CTA CTT CCT GAG CAC AAG AAA     627
Glu Met Thr Trp Tyr Lys Asp Gly Arg Leu Leu Pro Glu His Lys Lys
             190                 195                 200

AAT CCA ATT GAG ATG GCA GAT ATT TAT GTT TTT AAT CAA GGC TTG TAT     675
Asn Pro Ile Glu Met Ala Asp Ile Tyr Val Phe Asn Gln Gly Leu Tyr
         205                 210                 215

GTA TGT GAT TAC ACA CAG TCA GAT AAT GTG AGT TCC TGG ACA GTC CGA     723
Val Cys Asp Tyr Thr Gln Ser Asp Asn Val Ser Ser Trp Thr Val Arg
     220                 225                 230

GCT GTG GTT AAA GTG AGA ACC ATT GGT AAG GAC ATC AAT GTG AAG CCG     771
Ala Val Val Lys Val Arg Thr Ile Gly Lys Asp Ile Asn Val Lys Pro
235                 240                 245                 250

GAA ATT CTG GAT CCC ATT ACA GAT ACA CTG GAC GTA GAG CTT GGA AAG     819
Glu Ile Leu Asp Pro Ile Thr Asp Thr Leu Asp Val Glu Leu Gly Lys
                 255                 260                 265

CCT TTA ACT CTC CCC TGC AGA GTA CAG TTT GGC TTC CAA AGA CTT TCA     867
Pro Leu Thr Leu Pro Cys Arg Val Gln Phe Gly Phe Gln Arg Leu Ser
             270                 275                 280

AAG CCT GTG ATA AAG TGG TAT GTC AAA GAA TCT ACA CAG GAG TGG GAA     915
Lys Pro Val Ile Lys Trp Tyr Val Lys Glu Ser Thr Gln Glu Trp Glu
         285                 290                 295

ATG TCA GTA TTT GAG GAG AAA AGA ATT CAA TCC ACT TTC AAG AAT GAA     963
Met Ser Val Phe Glu Glu Lys Arg Ile Gln Ser Thr Phe Lys Asn Glu
     300                 305                 310

GTC ATT GAA CGT ACC ATC TTC TTG AGA GAA GTT ACC CAG AGA GAT CTC    1011
Val Ile Glu Arg Thr Ile Phe Leu Arg Glu Val Thr Gln Arg Asp Leu
315                 320                 325                 330

AGC AGA AAG TTT GTT TGC TTT GCC CAG AAC TCC ATT GGG AAC ACA ACA    1059
Ser Arg Lys Phe Val Cys Phe Ala Gln Asn Ser Ile Gly Asn Thr Thr
                 335                 340                 345
```

```
CGG ACC ATA CGG CTG AGG AAG AAG GAA GAG GTG GTG TTT GTA TAC ATC      1107
Arg Thr Ile Arg Leu Arg Lys Lys Glu Glu Val Val Phe Val Tyr Ile
            350                 355                 360

CTT CTC GGC ACG GCC TTG ATG CTG GTG GGC GTT CTG GTG GCA GCT GCT      1155
Leu Leu Gly Thr Ala Leu Met Leu Val Gly Val Leu Val Ala Ala Ala
            365                 370                 375

TTC CTC TAC TGG TAC TGG ATT GAA GTT GTC CTG CTC TGT CGA ACC TAC      1203
Phe Leu Tyr Trp Tyr Trp Ile Glu Val Val Leu Leu Cys Arg Thr Tyr
            380                 385                 390

AAG AAC AAA GAT GAG ACT CTG GGG GAT AAG AAG GAA TTC GAT GCA TTT      1251
Lys Asn Lys Asp Glu Thr Leu Gly Asp Lys Lys Glu Phe Asp Ala Phe
395                 400                 405                 410

GTA TCC TAC TCG AAT TGG AGC TCT CCT GAG ACT GAC GCC GTG GGA TCT      1299
Val Ser Tyr Ser Asn Trp Ser Ser Pro Glu Thr Asp Ala Val Gly Ser
            415                 420                 425

CTG AGT GAG GAA CAC CTG GCT CTG AAT CTT TTC CCG GAA GTG CTA GAA      1347
Leu Ser Glu Glu His Leu Ala Leu Asn Leu Phe Pro Glu Val Leu Glu
            430                 435                 440

GAC ACC TAT GGG TAC AGA TTG TGT TTG CTT GAC CGA GAT GTG ACC CCA      1395
Asp Thr Tyr Gly Tyr Arg Leu Cys Leu Leu Asp Arg Asp Val Thr Pro
            445                 450                 455

GGA GGA GTG TAT GCA GAT GAC ATT GTG AGC ATC ATT AAG AAA AGC CGA      1443
Gly Gly Val Tyr Ala Asp Asp Ile Val Ser Ile Ile Lys Lys Ser Arg
    460                 465                 470

AGA GGA ATA TTT ATC CTG AGT CCC AGC TAC CTC AAT GGA CCC CGT GTC      1491
Arg Gly Ile Phe Ile Leu Ser Pro Ser Tyr Leu Asn Gly Pro Arg Val
475                 480                 485                 490

TTT GAG CTA CAA GCA GCA GTG AAT CTT GCC TTG GTT GAT CAG ACA CTG      1539
Phe Glu Leu Gln Ala Ala Val Asn Leu Ala Leu Val Asp Gln Thr Leu
            495                 500                 505

AAG TTG ATT TTA ATT AAG TTC TGT TCC TTC CAA GAG CCA GAA TCT CTT      1587
Lys Leu Ile Leu Ile Lys Phe Cys Ser Phe Gln Glu Pro Glu Ser Leu
            510                 515                 520

CCT TAC CTT GTC AAA AAG GCT CTG CGG GTT CTC CCC ACA GTC ACA TGG      1635
Pro Tyr Leu Val Lys Lys Ala Leu Arg Val Leu Pro Thr Val Thr Trp
            525                 530                 535

AAA GGC TTG AAG TCG GTC CAC GCC AGT TCC AGG TTC TGG ACC CAA ATT      1683
Lys Gly Leu Lys Ser Val His Ala Ser Ser Arg Phe Trp Thr Gln Ile
            540                 545                 550

CGT TAC CAC ATG CCT GTG AAG AAC TCC AAC AGG TTT ATG TTC AAC GGG      1731
Arg Tyr His Met Pro Val Lys Asn Ser Asn Arg Phe Met Phe Asn Gly
555                 560                 565                 570

CTC AGA ATT TTC CTG AAG GGC TTT TCC CCT GAA AAG GAC CTA GTG ACA      1779
Leu Arg Ile Phe Leu Lys Gly Phe Ser Pro Glu Lys Asp Leu Val Thr
            575                 580                 585

CAG AAA CCC CTG GAA GGA ATG CCC AAG TCT GGG AAT GAC CAC GGA GCT      1827
Gln Lys Pro Leu Glu Gly Met Pro Lys Ser Gly Asn Asp His Gly Ala
            590                 595                 600

CAG AAC CTC CTT CTC TAC AGT GAC CAG AAG AGG TGC TGATGGGTAG           1873
Gln Asn Leu Leu Leu Tyr Ser Asp Gln Lys Arg Cys
            605                 610

AACTTGCTGT GTGGATCAGG CTGATAGAAA TTGAGCCTTT CTGCTCTCAG TGCCAAGCAA    1933

GCTTGACAGG CAGTGGAATG AAGCGGCATC TGTGGTTTTA GGGTCTGGGT TCCTGGAACA    1993

GACACAGAGC AATACTCCAG ACCTCTGCCG TGTGCTTAGC ACACATTTCC CTGAGAGTTC    2053

CCAAGTAGCC TGAACAGAAT CAACAGAAAT AGCTCCATGG GCTGTCCAAC ATTCATGCAC    2113

GCATGCCTGT TTTGCACTAT ATATATGAAT TTATCATACG TTTGTGTGTG TATATGCATT    2173
```

```
CAGATAAATA GGATTTTATT TTGTTCGATA CGAGTGATTG AAACTCCATC TAAAGCCCTT    2233

CTGTAAAGAA AAAAAAAAAA AAAAAA                                        2259
```

(2) INFORMATION FOR SEQ ID NO:16:

(i) SEQUENCE CHARACTERISTICS:
        (A) LENGTH: 614 amino acids
        (B) TYPE: amino acid
        (D) TOPOLOGY: linear (ii) MOLECULE TYPE: protein (xi) SEQUENCE DESCRIPTION: SEQ ID NO:16:

```
Met Leu Cys Leu Gly Trp Val Phe Leu Trp Phe Val Ala Gly Glu Lys
 1               5                  10                  15

Thr Thr Gly Phe Asn His Ser Ala Cys Ala Thr Lys Lys Leu Leu Trp
                20                  25                  30

Thr Tyr Ser Ala Arg Gly Ala Glu Asn Phe Val Leu Phe Cys Asp Leu
            35                  40                  45

Gln Glu Leu Gln Glu Gln Lys Phe Ser His Ala Ser Gln Leu Ser Pro
        50                  55                  60

Thr Gln Ser Pro Ala His Lys Pro Cys Ser Gly Ser Gln Lys Asp Leu
65                  70                  75                  80

Ser Asp Val Gln Trp Tyr Met Gln Pro Arg Ser Gly Ser Pro Leu Glu
                85                  90                  95

Glu Ile Ser Arg Asn Ser Pro His Met Gln Ser Glu Gly Met Leu His
            100                 105                 110

Ile Leu Ala Pro Gln Thr Asn Ser Ile Trp Ser Tyr Ile Cys Arg Pro
        115                 120                 125

Arg Ile Arg Ser Pro Gln Asp Met Ala Cys Cys Ile Lys Thr Val Leu
130                 135                 140

Glu Val Lys Pro Gln Arg Asn Val Ser Cys Gly Asn Thr Ala Gln Asp
145                 150                 155                 160

Glu Gln Val Leu Leu Leu Gly Ser Thr Gly Ser Ile His Cys Pro Ser
                165                 170                 175

Leu Ser Cys Gln Ser Asp Val Gln Ser Pro Glu Met Thr Trp Tyr Lys
            180                 185                 190

Asp Gly Arg Leu Leu Pro Glu His Lys Lys Asn Pro Ile Glu Met Ala
        195                 200                 205

Asp Ile Tyr Val Phe Asn Gln Gly Leu Tyr Val Cys Asp Tyr Thr Gln
    210                 215                 220

Ser Asp Asn Val Ser Ser Trp Thr Val Arg Ala Val Lys Val Arg
225                 230                 235                 240

Thr Ile Gly Lys Asp Ile Asn Val Lys Pro Glu Ile Leu Asp Pro Ile
                245                 250                 255

Thr Asp Thr Leu Asp Val Glu Leu Gly Lys Pro Leu Thr Leu Pro Cys
            260                 265                 270

Arg Val Gln Phe Gly Phe Gln Arg Leu Ser Lys Pro Val Ile Lys Trp
        275                 280                 285

Tyr Val Lys Glu Ser Thr Gln Glu Trp Glu Met Ser Val Phe Glu Glu
    290                 295                 300

Lys Arg Ile Gln Ser Thr Phe Lys Asn Glu Val Ile Glu Arg Thr Ile
305                 310                 315                 320

Phe Leu Arg Glu Val Thr Gln Arg Asp Leu Ser Arg Lys Phe Val Cys
                325                 330                 335
```

```
Phe Ala Gln Asn Ser Ile Gly Asn Thr Thr Arg Thr Ile Arg Leu Arg
            340                 345                 350
Lys Lys Glu Glu Val Val Phe Val Tyr Ile Leu Leu Gly Thr Ala Leu
            355                 360                 365
Met Leu Val Gly Val Leu Val Ala Ala Ala Phe Leu Tyr Trp Tyr Trp
        370                 375                 380
Ile Glu Val Val Leu Leu Cys Arg Thr Tyr Lys Asn Lys Asp Glu Thr
385                 390                 395                 400
Leu Gly Asp Lys Lys Glu Phe Asp Ala Phe Val Ser Tyr Ser Asn Trp
                405                 410                 415
Ser Ser Pro Glu Thr Asp Ala Val Gly Ser Leu Ser Glu Glu His Leu
            420                 425                 430
Ala Leu Asn Leu Phe Pro Glu Val Leu Glu Asp Thr Tyr Gly Tyr Arg
            435                 440                 445
Leu Cys Leu Leu Asp Arg Asp Val Thr Pro Gly Gly Val Tyr Ala Asp
        450                 455                 460
Asp Ile Val Ser Ile Ile Lys Lys Ser Arg Arg Gly Ile Phe Ile Leu
465                 470                 475                 480
Ser Pro Ser Tyr Leu Asn Gly Pro Arg Val Phe Glu Leu Gln Ala Ala
                485                 490                 495
Val Asn Leu Ala Leu Val Asp Gln Thr Leu Lys Leu Ile Leu Ile Lys
            500                 505                 510
Phe Cys Ser Phe Gln Glu Pro Glu Ser Leu Pro Tyr Leu Val Lys Lys
            515                 520                 525
Ala Leu Arg Val Leu Pro Thr Val Thr Trp Lys Gly Leu Lys Ser Val
        530                 535                 540
His Ala Ser Ser Arg Phe Trp Thr Gln Ile Arg Tyr His Met Pro Val
545                 550                 555                 560
Lys Asn Ser Asn Arg Phe Met Phe Asn Gly Leu Arg Ile Phe Leu Lys
                565                 570                 575
Gly Phe Ser Pro Glu Lys Asp Leu Val Thr Gln Lys Pro Leu Glu Gly
            580                 585                 590
Met Pro Lys Ser Gly Asn Asp His Gly Ala Gln Asn Leu Leu Leu Tyr
        595                 600                 605
Ser Asp Gln Lys Arg Cys
    610
```

(2) INFORMATION FOR SEQ ID NO:17:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..514

(ix) FEATURE:
        (A) NAME/KEY: misc_feature
        (B) LOCATION: 374
        (D) OTHER INFORMATION: /note= "nucleotides 374, 383, 396,
            403, 433, 458, 459, 483, and 515 are indicated as C;
            each may be A, C, G, or T"

(xi) SEQUENCE DESCRIPTION: SEQ ID NO:17:

```
C TGT GAA TTA AAA TAT GGA GGC TTT GTT GTG AGA AGA ACT ACT GAA         46
```

```
        Cys Glu Leu Lys Tyr Gly Gly Phe Val Val Arg Arg Thr Thr Glu
          1               5                  10                  15

TTA ACT GTT ACA GCC CCT CTG ACT GAT AAG CCA CCC AAG CTT TTG TAT        94
Leu Thr Val Thr Ala Pro Leu Thr Asp Lys Pro Pro Lys Leu Leu Tyr
                 20                  25                  30

CCT ATG GAA AGT AAA CTG ACA ATT CAG GAG ACC CAG CTG GGT GAC TCT       142
Pro Met Glu Ser Lys Leu Thr Ile Gln Glu Thr Gln Leu Gly Asp Ser
             35                  40                  45

GCT AAT CTA ACC TGC AGA GCT TTC TTT GGG TAC AGC GGA GAT GTC AGT       190
Ala Asn Leu Thr Cys Arg Ala Phe Phe Gly Tyr Ser Gly Asp Val Ser
             50                  55                  60

CCT TTA ATT TAC TGG ATG AAA GGA GAA AAA TTT ATT GAA GAT CTG GAT       238
Pro Leu Ile Tyr Trp Met Lys Gly Glu Lys Phe Ile Glu Asp Leu Asp
     65                  70                  75

GAA AAT CGA GTT TGG GAA AGT GAC ATT AGA ATT CTT AAG GAG CAT CTT       286
Glu Asn Arg Val Trp Glu Ser Asp Ile Arg Ile Leu Lys Glu His Leu
 80                  85                  90                  95

GGG GAA CAG GAA GTT TCC ATC TCA TTA ATT GTG GAC TCT GTG GAA GAA       334
Gly Glu Gln Glu Val Ser Ile Ser Leu Ile Val Asp Ser Val Glu Glu
                100                 105                 110

GGT GAC TTG GGA AAT TAC TCC TGT TAT GTT GAA AAA TGG CAA TGG ACG       382
Gly Asp Leu Gly Asn Tyr Ser Cys Tyr Val Glu Lys Trp Gln Trp Thr
             115                 120                 125

CCG ACA CGC CAG CCG TCC CCC TTC ATA AAC GAG AGC CTA ATG TAC ACA       430
Pro Thr Arg Gln Pro Ser Pro Phe Ile Asn Glu Ser Leu Met Tyr Thr
         130                 135                 140

GTC GGA ACT TGC CTG GAG GCC CTT GGG CCA AAA CCT TGG TGG TTG AAT       478
Val Gly Thr Cys Leu Glu Ala Leu Gly Pro Lys Pro Trp Trp Leu Asn
     145                 150                 155

GTT TCG GGA CCA CCT TCA AAG TGT ACC AAG GTT GGA CC                    516
Val Ser Gly Pro Pro Ser Lys Cys Thr Lys Val Gly
 160                 165                 170

(2) INFORMATION FOR SEQ ID NO:18:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO:18:

Cys Glu Leu Lys Tyr Gly Gly Phe Val Val Arg Arg Thr Thr Glu Leu
  1               5                  10                  15

Thr Val Thr Ala Pro Leu Thr Asp Lys Pro Pro Lys Leu Leu Tyr Pro
             20                  25                  30

Met Glu Ser Lys Leu Thr Ile Gln Glu Thr Gln Leu Gly Asp Ser Ala
         35                  40                  45

Asn Leu Thr Cys Arg Ala Phe Phe Gly Tyr Ser Gly Asp Val Ser Pro
     50                  55                  60

Leu Ile Tyr Trp Met Lys Gly Glu Lys Phe Ile Glu Asp Leu Asp Glu
 65                  70                  75                  80

Asn Arg Val Trp Glu Ser Asp Ile Arg Ile Leu Lys Glu His Leu Gly
             85                  90                  95

Glu Gln Glu Val Ser Ile Ser Leu Ile Val Asp Ser Val Glu Glu Gly
         100                 105                 110

Asp Leu Gly Asn Tyr Ser Cys Tyr Val Glu Lys Trp Gln Trp Thr Pro
     115                 120                 125
```

```
Thr Arg Gln Pro Ser Pro Phe Ile Asn Glu Ser Leu Met Tyr Thr Val
    130                 135                 140
Gly Thr Cys Leu Glu Ala Leu Gly Pro Lys Pro Trp Trp Leu Asn Val
145                 150                 155                 160
Ser Gly Pro Pro Ser Lys Cys Thr Lys Val Gly
                165                 170

(2) INFORMATION FOR SEQ ID NO:19:

(i) SEQUENCE CHARACTERISTICS:
         (A) LENGTH: 1991 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..1458

(xi) SEQUENCE DESCRIPTION: SEQ ID NO:19:
```

| | | | | | | | | | | | | | | | | |
|---|---|---|---|---|---|---|---|---|---|---|---|---|---|---|---|---|
| GAA | TTC | GGC | ACG | AGC | TGT | GAA | TTA | AAA | TAT | GGA | GGC | TTT | GTT | GTG | AGA | 48 |
| Glu | Phe | Gly | Thr | Ser | Cys | Glu | Leu | Lys | Tyr | Gly | Gly | Phe | Val | Val | Arg | |
| 1 | | | | 5 | | | | | 10 | | | | | 15 | | |
| AGA | ACT | ACT | GAA | TTA | ACT | GTT | ACA | GCC | CCT | CTG | ACT | GAT | AAG | CCA | CCC | 96 |
| Arg | Thr | Thr | Glu | Leu | Thr | Val | Thr | Ala | Pro | Leu | Thr | Asp | Lys | Pro | Pro | |
| | | | 20 | | | | | 25 | | | | | 30 | | | |
| AAG | CTT | TTG | TAT | CCT | ATG | GAA | AGT | AAA | CTG | ACA | ATT | CAG | GAG | ACC | CAG | 144 |
| Lys | Leu | Leu | Tyr | Pro | Met | Glu | Ser | Lys | Leu | Thr | Ile | Gln | Glu | Thr | Gln | |
| | | 35 | | | | | 40 | | | | | 45 | | | | |
| CTG | GGT | GAC | TCT | GCT | AAT | CTA | ACC | TGC | AGA | GCT | TTC | TTT | GGG | TAC | AGC | 192 |
| Leu | Gly | Asp | Ser | Ala | Asn | Leu | Thr | Cys | Arg | Ala | Phe | Phe | Gly | Tyr | Ser | |
| | 50 | | | | | 55 | | | | | 60 | | | | | |
| GGA | GAT | GTC | AGT | CCT | TTA | ATT | TAC | TGG | ATG | AAA | GGA | GAA | AAA | TTT | ATT | 240 |
| Gly | Asp | Val | Ser | Pro | Leu | Ile | Tyr | Trp | Met | Lys | Gly | Glu | Lys | Phe | Ile | |
| 65 | | | | | 70 | | | | | 75 | | | | | 80 | |
| GAA | GAT | CTG | GAT | GAA | AAT | CGA | GTT | TGG | GAA | AGT | GAC | ATT | AGA | ATT | CTT | 288 |
| Glu | Asp | Leu | Asp | Glu | Asn | Arg | Val | Trp | Glu | Ser | Asp | Ile | Arg | Ile | Leu | |
| | | | | 85 | | | | | 90 | | | | | 95 | | |
| AAG | GAG | CAT | CTT | GGG | GAA | CAG | GAA | GTT | TCC | ATC | TCA | TTA | ATT | GTG | GAC | 336 |
| Lys | Glu | His | Leu | Gly | Glu | Gln | Glu | Val | Ser | Ile | Ser | Leu | Ile | Val | Asp | |
| | | | 100 | | | | | 105 | | | | | 110 | | | |
| TCT | GTG | GAA | GAA | GGT | GAC | TTG | GGA | AAT | TAC | TCC | TGT | TAT | GTT | GAA | AAT | 384 |
| Ser | Val | Glu | Glu | Gly | Asp | Leu | Gly | Asn | Tyr | Ser | Cys | Tyr | Val | Glu | Asn | |
| | | 115 | | | | | 120 | | | | | 125 | | | | |
| GGA | AAT | GGA | CGT | CGA | CAC | GCC | AGC | GTT | CTC | CTT | CAT | AAA | CGA | GAG | CTA | 432 |
| Gly | Asn | Gly | Arg | Arg | His | Ala | Ser | Val | Leu | Leu | His | Lys | Arg | Glu | Leu | |
| | 130 | | | | | 135 | | | | | 140 | | | | | |
| ATG | TAC | ACA | GTG | GAA | CTT | GCT | GGA | GGC | CTT | GGT | GCT | ATA | CTC | TTG | CTG | 480 |
| Met | Tyr | Thr | Val | Glu | Leu | Ala | Gly | Gly | Leu | Gly | Ala | Ile | Leu | Leu | Leu | |
| 145 | | | | | 150 | | | | | 155 | | | | | 160 | |
| CTT | GTA | TGT | TTG | GTG | ACC | ATC | TAC | AAG | TGT | TAC | AAG | ATA | GAA | ATC | ATG | 528 |
| Leu | Val | Cys | Leu | Val | Thr | Ile | Tyr | Lys | Cys | Tyr | Lys | Ile | Glu | Ile | Met | |
| | | | | 165 | | | | | 170 | | | | | 175 | | |
| CTC | TTC | TAC | AGG | AAT | CAT | TTT | GGA | GCT | GAA | GAG | CTC | GAT | GGA | GAC | AAT | 576 |
| Leu | Phe | Tyr | Arg | Asn | His | Phe | Gly | Ala | Glu | Glu | Leu | Asp | Gly | Asp | Asn | |
| | | | 180 | | | | | 185 | | | | | 190 | | | |
| AAA | GAT | TAT | GAT | GCA | TAC | TTA | TCA | TAC | ACC | AAA | GTG | GAT | CCT | GAC | CAG | 624 |
| Lys | Asp | Tyr | Asp | Ala | Tyr | Leu | Ser | Tyr | Thr | Lys | Val | Asp | Pro | Asp | Gln | |
| | | 195 | | | | | 200 | | | | | 205 | | | | |
| TGG | AAT | CAA | GAG | ACT | GGG | GAA | GAA | GAA | CGT | TTT | GCC | CTT | GAA | ATC | CTA | 672 |

```
Trp Asn Gln Glu Thr Gly Glu Glu Arg Phe Ala Leu Glu Ile Leu
    210                 215                 220

CCT GAT ATG CTT GAA AAG CAT TAT GGA TAT AAG TTG TTT ATA CCA GAT        720
Pro Asp Met Leu Glu Lys His Tyr Gly Tyr Lys Leu Phe Ile Pro Asp
225                 230                 235                 240

AGA GAT TTA ATC CCA ACT GGA ACA TAC ATT GAA GAT GTG GCA AGA TGT        768
Arg Asp Leu Ile Pro Thr Gly Thr Tyr Ile Glu Asp Val Ala Arg Cys
                245                 250                 255

GTA GAT CAA AGC AAG CGG CTG ATT ATT GTC ATG ACC CCA AAT TAC GTA        816
Val Asp Gln Ser Lys Arg Leu Ile Ile Val Met Thr Pro Asn Tyr Val
                260                 265                 270

GTT AGA AGG GGC TGG AGC ATC TTT GAG CTG GAA ACC AGA CTT CGA AAT        864
Val Arg Arg Gly Trp Ser Ile Phe Glu Leu Glu Thr Arg Leu Arg Asn
            275                 280                 285

ATG CTT GTG ACT GGA GAA ATT AAA GTG ATT CTA ATT GAA TGC AGT GAA        912
Met Leu Val Thr Gly Glu Ile Lys Val Ile Leu Ile Glu Cys Ser Glu
        290                 295                 300

CTG AGA GGA ATT ATG AAC TAC CAG GAG GTG GAG GCC CTG AAG CAC ACC        960
Leu Arg Gly Ile Met Asn Tyr Gln Glu Val Glu Ala Leu Lys His Thr
305                 310                 315                 320

ATC AAG CTC CTG ACG GTC ATT AAA TGG CAT GGA CCA AAA TGC AAC AAG       1008
Ile Lys Leu Leu Thr Val Ile Lys Trp His Gly Pro Lys Cys Asn Lys
                325                 330                 335

TTG AAC TCC AAG TTC TGG AAA CGT TTA CAG TAT GAA ATG CCT TTT AAG       1056
Leu Asn Ser Lys Phe Trp Lys Arg Leu Gln Tyr Glu Met Pro Phe Lys
                340                 345                 350

AGG ATA GAA CCC ATT ACA CAT GAG CAG GCT TTA GAT GTC AGT GAG CAA       1104
Arg Ile Glu Pro Ile Thr His Glu Gln Ala Leu Asp Val Ser Glu Gln
            355                 360                 365

GGG CCT TTT GGG GAG CTG CAG ACT GTC TCG GCC ATT TCC ATG GCC GCG       1152
Gly Pro Phe Gly Glu Leu Gln Thr Val Ser Ala Ile Ser Met Ala Ala
370                 375                 380

GCC ACC TCC ACA GCT CTA GCC ACT GCC CAT CCA GAT CTC CGT TCT ACC       1200
Ala Thr Ser Thr Ala Leu Ala Thr Ala His Pro Asp Leu Arg Ser Thr
385                 390                 395                 400

TTT CAC AAC ACG TAC CAT TCA CAA ATG CGT CAG AAA CAC TAC TAC CGA       1248
Phe His Asn Thr Tyr His Ser Gln Met Arg Gln Lys His Tyr Tyr Arg
                405                 410                 415

AGC TAT GAG TAC GAC GTA CCT CCT ACC GGC ACC CTG CCT CTT ACC TCC       1296
Ser Tyr Glu Tyr Asp Val Pro Pro Thr Gly Thr Leu Pro Leu Thr Ser
                420                 425                 430

ATA GGC AAT CAG CAT ACC TAC TGT AAC ATC CCT ATG ACA CTC ATC AAC       1344
Ile Gly Asn Gln His Thr Tyr Cys Asn Ile Pro Met Thr Leu Ile Asn
            435                 440                 445

GGG CAG CGG CCA CAG ACA AAA TCG AGC AGG GAG CAG AAT CCA GAT GAG       1392
Gly Gln Arg Pro Gln Thr Lys Ser Ser Arg Glu Gln Asn Pro Asp Glu
450                 455                 460

GCC CAC ACA AAC AGT GCC ATC CTG CCG CTG TTG CCA AGG GAG ACC AGT       1440
Ala His Thr Asn Ser Ala Ile Leu Pro Leu Leu Pro Arg Glu Thr Ser
465                 470                 475                 480

ATA TCC AGT GTG ATA TGG TGACAGAAAA GCAAGGGACA TCCCGTCCCT              1488
Ile Ser Ser Val Ile Trp
                485

GGGAGGTTGA GTGGAATCTG CAGTCCAGTG CCTGGAACTA AATCCTCGAC TGCTGCTGTT     1548

AAAAAACATG CATTAGAATC TTTAGAACAC GAGGAAAAAC AGGGTCTTGT ACATATGTTT     1608

TTTGGAATTT CTTTGTAGCA TCAGTGTCCT CCTGTTTTAC CATGTCTTTT ACCATTACAT     1668

TTTTTGACTT TGTTTATAT GTCGTTGGAA TTTGTAAATT TACATTTTTT TTAAAGAAGA      1728
```

```
GACTGATGTG TAGATAGAAA ACCCTTTTTT TGCTTCATTA GTTTAGTTTT AGAATGGGTT    1788

TTTATTTTAT TTCCTTTTTT AAAATTTTAC TTTGCTTTTA ACATTTCCTT GGGGTGCTTG    1848

AACAAATCTA TCCGATGGGA CAAGGAGCAC CGGATTCTTT CTCGGGTTCT GCCTAGCATC    1908

AACTGGGCCA CGTCGGCCTT CAGAGAACAG TGCAACAAAT GCCAGCATTG CCATTCGGGG    1968

GGAAAAAAAA AAAAAAAAA AAA                                             1991
```

(2) INFORMATION FOR SEQ ID NO:20:

(i) SEQUENCE CHARACTERISTICS:
        (A) LENGTH: 486 amino acids
        (B) TYPE: amino acid
        (D) TOPOLOGY: linear (ii) MOLECULE TYPE: protein (xi) SEQUENCE DESCRIPTION: SEQ ID NO:20:

```
Glu Phe Gly Thr Ser Cys Glu Leu Lys Tyr Gly Gly Phe Val Val Arg
 1               5                  10                  15

Arg Thr Thr Glu Leu Thr Val Thr Ala Pro Leu Thr Asp Lys Pro Pro
                20                  25                  30

Lys Leu Leu Tyr Pro Met Glu Ser Lys Leu Thr Ile Gln Glu Thr Gln
            35                  40                  45

Leu Gly Asp Ser Ala Asn Leu Thr Cys Arg Ala Phe Phe Gly Tyr Ser
        50                  55                  60

Gly Asp Val Ser Pro Leu Ile Tyr Trp Met Lys Gly Glu Lys Phe Ile
65                  70                  75                  80

Glu Asp Leu Asp Glu Asn Arg Val Trp Glu Ser Asp Ile Arg Ile Leu
                85                  90                  95

Lys Glu His Leu Gly Glu Gln Glu Val Ser Ile Ser Leu Ile Val Asp
            100                 105                 110

Ser Val Glu Glu Gly Asp Leu Gly Asn Tyr Ser Cys Tyr Val Glu Asn
        115                 120                 125

Gly Asn Gly Arg Arg His Ala Ser Val Leu Leu His Lys Arg Glu Leu
130                 135                 140

Met Tyr Thr Val Glu Leu Ala Gly Gly Leu Gly Ala Ile Leu Leu Leu
145                 150                 155                 160

Leu Val Cys Leu Val Thr Ile Tyr Lys Cys Tyr Lys Ile Glu Ile Met
                165                 170                 175

Leu Phe Tyr Arg Asn His Phe Gly Ala Glu Glu Leu Asp Gly Asp Asn
            180                 185                 190

Lys Asp Tyr Asp Ala Tyr Leu Ser Tyr Thr Lys Val Asp Pro Asp Gln
        195                 200                 205

Trp Asn Gln Glu Thr Gly Glu Glu Arg Phe Ala Leu Glu Ile Leu
210                 215                 220

Pro Asp Met Leu Glu Lys His Tyr Gly Tyr Lys Leu Phe Ile Pro Asp
225                 230                 235                 240

Arg Asp Leu Ile Pro Thr Gly Thr Tyr Ile Glu Asp Val Ala Arg Cys
                245                 250                 255

Val Asp Gln Ser Lys Arg Leu Ile Ile Val Met Thr Pro Asn Tyr Val
            260                 265                 270

Val Arg Arg Gly Trp Ser Ile Phe Glu Leu Glu Thr Arg Leu Arg Asn
        275                 280                 285

Met Leu Val Thr Gly Glu Ile Lys Val Ile Leu Ile Glu Cys Ser Glu
290                 295                 300
```

```
Leu Arg Gly Ile Met Asn Tyr Gln Glu Val Glu Ala Leu Lys His Thr
305                 310                 315                 320

Ile Lys Leu Leu Thr Val Ile Lys Trp His Gly Pro Lys Cys Asn Lys
                325                 330                 335

Leu Asn Ser Lys Phe Trp Lys Arg Leu Gln Tyr Glu Met Pro Phe Lys
                340                 345                 350

Arg Ile Glu Pro Ile Thr His Glu Gln Ala Leu Asp Val Ser Glu Gln
                355                 360                 365

Gly Pro Phe Gly Glu Leu Gln Thr Val Ser Ala Ile Ser Met Ala Ala
370                 375                 380

Ala Thr Ser Thr Ala Leu Ala Thr Ala His Pro Asp Leu Arg Ser Thr
385                 390                 395                 400

Phe His Asn Thr Tyr His Ser Gln Met Arg Gln Lys His Tyr Tyr Arg
                405                 410                 415

Ser Tyr Glu Tyr Asp Val Pro Pro Thr Gly Thr Leu Pro Leu Thr Ser
                420                 425                 430

Ile Gly Asn Gln His Thr Tyr Cys Asn Ile Pro Met Thr Leu Ile Asn
                435                 440                 445

Gly Gln Arg Pro Gln Thr Lys Ser Ser Arg Glu Gln Asn Pro Asp Glu
450                 455                 460

Ala His Thr Asn Ser Ala Ile Leu Pro Leu Leu Pro Arg Glu Thr Ser
465                 470                 475                 480

Ile Ser Ser Val Ile Trp
                485

(2) INFORMATION FOR SEQ ID NO:21:

(i) SEQUENCE CHARACTERISTICS:
        (A) LENGTH: 570 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:21:

Met Gly Leu Leu Trp Tyr Leu Met Ser Leu Ser Phe Tyr Gly Ile Leu
1               5                   10                  15

Gln Ser His Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
                35                  40                  45

Leu Phe Glu His Phe Leu Lys Tyr Asn Tyr Ser Thr Ala His Ser Ser
50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
                100                 105                 110

Thr Cys Met Leu Arg Asn Thr Thr Tyr Cys Ser Lys Val Ala Phe Pro
                115                 120                 125

Leu Glu Val Val Gln Lys Asp Ser Cys Phe Asn Ser Ala Met Arg Phe
                130                 135                 140

Pro Val His Lys Met Tyr Ile Glu His Gly Ile His Lys Ile Thr Cys
145                 150                 155                 160
```

```
Pro Asn Val Asp Gly Tyr Phe Pro Ser Ser Val Lys Pro Ser Val Thr
            165                 170                 175
Trp Tyr Lys Gly Cys Thr Glu Ile Val Asp Phe His Asn Val Leu Pro
            180                 185                 190
Glu Gly Met Asn Leu Ser Phe Phe Ile Pro Leu Val Ser Asn Asn Gly
            195                 200                 205
Asn Tyr Thr Cys Val Val Thr Tyr Pro Glu Asn Gly Arg Leu Phe His
            210                 215                 220
Leu Thr Arg Thr Val Thr Val Lys Val Val Gly Ser Pro Lys Asp Ala
225                 230                 235                 240
Leu Pro Pro Gln Ile Tyr Ser Pro Asn Asp Arg Val Val Tyr Glu Lys
            245                 250                 255
Glu Pro Gly Glu Glu Leu Val Ile Pro Cys Lys Val Tyr Phe Ser Phe
            260                 265                 270
Ile Met Asp Ser His Asn Glu Val Trp Trp Thr Ile Asp Gly Lys Lys
            275                 280                 285
Pro Asp Asp Val Thr Val Asp Ile Thr Ile Asn Glu Ser Val Ser Tyr
290                 295                 300
Ser Ser Thr Glu Asp Glu Thr Arg Thr Gln Ile Leu Ser Ile Lys Lys
305                 310                 315                 320
Val Thr Pro Glu Asp Leu Arg Arg Asn Tyr Val Cys His Ala Arg Asn
            325                 330                 335
Thr Lys Gly Glu Ala Glu Gln Ala Ala Lys Val Lys Gln Lys Val Ile
            340                 345                 350
Pro Pro Arg Tyr Thr Val Glu Leu Ala Cys Gly Phe Gly Ala Thr Val
            355                 360                 365
Phe Leu Val Val Leu Ile Val Val Tyr His Val Tyr Trp Leu Glu
            370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Val Glu
            405                 410                 415
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
            435                 440                 445
Ile Val Thr Asp Glu Thr Leu Ser Phe Ile Gln Lys Ser Arg Arg Leu
450                 455                 460
Leu Val Val Leu Ser Pro Asn Tyr Val Leu Gln Gly Thr Gln Ala Leu
465                 470                 475                 480
Leu Glu Leu Lys Ala Gly Leu Glu Asn Met Ala Ser Arg Gly Asn Ile
            485                 490                 495
Asn Val Ile Leu Val Gln Tyr Lys Ala Val Lys Asp Met Lys Val Lys
            500                 505                 510
Glu Leu Lys Arg Ala Lys Thr Val Leu Thr Val Ile Lys Trp Lys Gly
            515                 520                 525
Glu Lys Ser Lys Tyr Pro Gln Gly Arg Phe Trp Lys Gln Leu Gln Val
            530                 535                 540
Ala Met Pro Val Lys Lys Ser Pro Arg Trp Ser Ser Asn Asp Lys Gln
545                 550                 555                 560
Gly Leu Ser Tyr Ser Ser Leu Lys Asn Val
            565                 570
```

(2) INFORMATION FOR SEQ ID NO:22:

(i) SEQUENCE CHARACTERISTICS:
        (A) LENGTH: 562 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

```
Met Trp Ser Leu Leu Leu Cys Gly Leu Ser Ile Ala Leu Pro Leu Ser
1               5                   10                  15

Val Thr Ala Asp Gly Cys Lys Asp Ile Phe Met Lys Asn Glu Ile Leu
            20                  25                  30

Ser Ala Ser Gln Pro Phe Ala Phe Asn Cys Thr Phe Pro Pro Ile Thr
        35                  40                  45

Ser Gly Glu Val Ser Val Thr Trp Tyr Lys Asn Ser Ser Lys Ile Pro
    50                  55                  60

Val Ser Lys Ile Ile Gln Ser Arg Ile His Gln Asp Glu Thr Trp Ile
65                  70                  75                  80

Leu Phe Leu Pro Met Glu Trp Gly Asp Ser Gly Val Tyr Gln Cys Val
                85                  90                  95

Ile Lys Gly Arg Asp Ser Cys His Arg Ile His Val Asn Leu Thr Val
            100                 105                 110

Phe Glu Lys His Trp Cys Asp Thr Ser Ile Gly Leu Pro Asn Leu
        115                 120                 125

Ser Asp Glu Tyr Lys Gln Ile Leu His Leu Gly Lys Asp Asp Ser Leu
    130                 135                 140

Thr Cys His Leu His Phe Pro Lys Ser Cys Val Leu Gly Pro Ile Lys
145                 150                 155                 160

Trp Tyr Lys Asp Cys Asn Glu Ile Lys Gly Glu Arg Phe Thr Val Leu
                165                 170                 175

Glu Thr Arg Leu Leu Val Ser Asn Val Ser Ala Glu Asp Arg Gly Asn
            180                 185                 190

Tyr Ala Cys Gln Ala Ile Leu Thr His Ser Gly Lys Gln Tyr Glu Val
        195                 200                 205

Leu Asn Gly Ile Thr Val Ser Ile Thr Glu Arg Ala Gly Tyr Gly Gly
    210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270

Tyr Tyr Asp Glu Ser Lys Arg Ile Arg Glu Gly Val Glu Thr His Val
        275                 280                 285

Ser Phe Arg Glu His Asn Leu Tyr Thr Val Asn Ile Thr Phe Leu Glu
    290                 295                 300

Val Lys Met Glu Asp Tyr Gly Leu Pro Phe Met Cys His Ala Gly Val
305                 310                 315                 320

Ser Thr Ala Tyr Ile Ile Leu Gln Leu Pro Ala Pro Asp Phe Arg Ala
                325                 330                 335

Tyr Leu Ile Gly Gly Leu Ile Ala Leu Ala Val Ala Val Ser Val
            340                 345                 350

Val Tyr Ile Tyr Asn Ile Phe Lys Ile Asp Ile Val Leu Trp Tyr Arg
```

```
                    355                 360                 365
Ser Ala Phe His Ser Thr Glu Thr Ile Val Asp Gly Lys Leu Tyr Asp
    370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
                420                 425                 430

Ala Val Ala Asn Val Ile Asp Glu Asn Val Lys Leu Cys Arg Arg Leu
            435                 440                 445

Ile Val Ile Val Val Pro Glu Ser Leu Gly Phe Gly Leu Leu Lys Asn
    450                 455                 460

Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495

Met Pro Glu Ser Ile Gln Tyr Ile Lys Gln Lys His Gly Ala Ile Arg
                500                 505                 510

Trp His Gly Asp Phe Thr Glu Gln Ser Gln Cys Met Lys Thr Lys Phe
            515                 520                 525

Trp Lys Thr Val Arg Tyr His Met Pro Pro Arg Arg Cys Arg Pro Phe
    530                 535                 540

Leu Arg Ser Thr Cys Arg Ser Thr His Leu Cys Thr Ala Pro Gln Ala
545                 550                 555                 560

Gln Asn (2) INFORMATION FOR SEQ ID NO:23:

(i) SEQUENCE CHARACTERISTICS:
        (A) LENGTH: 561 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:23:

Met Gly Met Pro Pro Leu Leu Phe Cys Trp Val Ser Phe Val Leu Pro
1               5                   10                  15

Leu Phe Val Ala Ala Gly Asn Cys Thr Asp Val Tyr Met His His Glu
                20                  25                  30

Met Ile Ser Glu Gly Gln Pro Phe Pro Phe Asn Cys Thr Tyr Pro Pro
            35                  40                  45

Val Thr Asn Gly Ala Val Asn Leu Thr Trp His Arg Thr Pro Ser Lys
    50                  55                  60

Ser Pro Ile Ser Ile Asn Arg His Val Arg Ile His Gln Asp Gln Ser
65                  70                  75                  80

Trp Ile Leu Phe Leu Pro Leu Ala Leu Glu Asp Ser Gly Ile Tyr Gln
                85                  90                  95

Cys Val Ile Lys Asp Ala His Ser Cys Tyr Arg Ile Ala Ile Asn Leu
                100                 105                 110

Thr Val Phe Arg Lys His Trp Cys Asp Ser Ser Asn Glu Glu Ser Ser
            115                 120                 125

Ile Asn Ser Ser Asp Glu Tyr Gln Gln Trp Leu Pro Ile Gly Lys Ser
    130                 135                 140
```

-continued

```
Gly Ser Leu Thr Cys His Leu Tyr Phe Pro Glu Ser Cys Val Leu Asp
145                 150                 155                 160

Ser Ile Lys Trp Tyr Lys Gly Cys Glu Glu Ile Lys Val Ser Lys Lys
                165                 170                 175

Phe Cys Pro Thr Gly Thr Lys Leu Leu Val Asn Asn Ile Asp Val Glu
            180                 185                 190

Asp Ser Gly Ser Tyr Ala Cys Ser Ala Arg Leu Thr His Leu Gly Arg
        195                 200                 205

Ile Phe Thr Val Arg Asn Tyr Ile Ala Val Asn Thr Lys Glu Val Gly
    210                 215                 220

Ser Gly Gly Arg Ile Pro Asn Ile Thr Tyr Pro Lys Asn Asn Ser Ile
225                 230                 235                 240

Glu Val Gln Leu Gly Ser Thr Leu Ile Val Asp Cys Asn Ile Thr Asp
                245                 250                 255

Thr Lys Glu Asn Thr Asn Leu Arg Cys Trp Arg Val Asn Asn Thr Leu
            260                 265                 270

Val Asp Asp Tyr Tyr Asn Asp Phe Lys Arg Ile Gln Glu Gly Ile Glu
        275                 280                 285

Thr Asn Leu Ser Leu Arg Asn His Ile Leu Tyr Thr Val Asn Ile Thr
    290                 295                 300

Phe Leu Glu Val Lys Met Glu Asp Tyr Gly His Pro Phe Thr Cys His
305                 310                 315                 320

Ala Ala Val Ser Ala Ala Tyr Ile Ile Leu Lys Arg Pro Ala Pro Asp
                325                 330                 335

Phe Arg Ala Tyr Leu Ile Gly Gly Leu Met Ala Phe Leu Leu Leu Ala
            340                 345                 350

Val Ser Ile Leu Tyr Ile Tyr Asn Thr Phe Lys Val Asp Ile Val Leu
        355                 360                 365

Trp Tyr Arg Ser Thr Phe His Thr Ala Gln Ala Pro Asp Asp Glu Lys
    370                 375                 380

Leu Tyr Asp Ala Tyr Val Leu Tyr Pro Lys Tyr Pro Arg Glu Ser Gln
385                 390                 395                 400

Gly His Asp Val Asp Thr Leu Val Leu Lys Ile Leu Pro Glu Val Leu
                405                 410                 415

Glu Lys Gln Cys Gly Tyr Lys Leu Phe Ile Phe Gly Arg Asp Glu Phe
            420                 425                 430

Pro Gly Gln Ala Val Ala Ser Val Ile Asp Glu Asn Ile Lys Leu Cys
        435                 440                 445

Arg Arg Leu Met Val Leu Val Ala Pro Glu Thr Ser Ser Phe Ser Phe
450                 455                 460

Leu Lys Asn Leu Thr Glu Glu Gln Ile Ala Val Tyr Asn Ala Leu Val
465                 470                 475                 480

Gln Asp Gly Met Lys Val Ile Leu Ile Glu Leu Glu Arg Val Lys Asp
                485                 490                 495

Tyr Ser Thr Met Pro Glu Ser Ile Gln Tyr Ile Arg Gln Lys His Gly
            500                 505                 510

Ala Ile Gln Trp Asp Gly Asp Phe Thr Glu Gln Ala Gln Cys Ala Lys
        515                 520                 525

Thr Lys Phe Trp Lys Lys Val Arg Tyr His Met Pro Pro Arg Arg Tyr
    530                 535                 540

Pro Ala Ser Pro Pro Val Gln Leu Leu Gly His Thr Pro Arg Ile Pro
545                 550                 555                 560
```

Gly (2) INFORMATION FOR SEQ ID NO:24:

(i) SEQUENCE CHARACTERISTICS:
        (A) LENGTH: 567 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:24:

```
Met Ile Asp Arg Gln Arg Met Gly Leu Trp Ala Leu Ala Ile Leu Thr
 1               5                  10                  15

Leu Pro Met Tyr Leu Thr Val Thr Glu Gly Ser Lys Ser Ser Trp Gly
                20                  25                  30

Leu Glu Asn Glu Ala Leu Ile Val Arg Cys Pro Gln Arg Gly Arg Ser
                35                  40                  45

Thr Tyr Pro Val Glu Trp Tyr Tyr Ser Asp Thr Asn Glu Ser Ile Pro
            50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
                100                 105                 110

Lys Pro Pro Ser Cys Asn Ile Pro Asp Tyr Leu Met Tyr Ser Thr Val
                115                 120                 125

Arg Gly Ser Asp Lys Asn Phe Lys Ile Thr Cys Pro Thr Ile Asp Leu
                130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
                180                 185                 190

Glu Asn Gly Thr Asn Tyr Ile Val Thr Ala Thr Arg Ser Phe Thr Val
                195                 200                 205

Glu Glu Lys Gly Phe Ser Met Phe Pro Val Ile Thr Asn Pro Pro Tyr
                210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
                260                 265                 270

Glu Glu Glu Gly Arg Asn Glu Ser Ser Asn Asp Met Asp Cys Leu
                275                 280                 285

Thr Ser Val Leu Arg Ile Thr Gly Val Thr Glu Lys Asp Leu Ser Leu
                290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ile Asp His Arg Ser Ile Tyr Tyr
                325                 330                 335

Ile Val Ala Gly Cys Ser Leu Leu Leu Met Phe Ile Asn Val Leu Val
```

```
                    340                 345                 350
Ile Val Leu Lys Val Phe Trp Ile Glu Val Ala Leu Phe Trp Arg Asp
            355                 360                 365
Ile Val Thr Pro Tyr Lys Thr Arg Asn Asp Gly Lys Leu Tyr Asp Ala
    370                 375                 380
Tyr Ile Ile Tyr Pro Arg Val Phe Arg Gly Ser Ala Ala Gly Thr His
385                 390                 395                 400
Ser Val Glu Tyr Phe Val His His Thr Leu Pro Asp Val Leu Glu Asn
                405                 410                 415
Lys Cys Gly Tyr Lys Leu Cys Ile Tyr Gly Arg Asp Leu Leu Pro Gly
            420                 425                 430
Gln Asp Ala Ala Thr Val Val Glu Ser Ser Ile Gln Asn Ser Arg Arg
                435                 440                 445
Gln Val Phe Val Leu Ala Pro His Met Met His Ser Lys Glu Phe Ala
            450                 455                 460
Tyr Glu Gln Glu Ile Ala Leu His Ser Ala Leu Ile Gln Asn Asn Ser
465                 470                 475                 480
Lys Val Ile Leu Ile Glu Met Glu Pro Leu Gly Glu Ala Ser Arg Leu
                485                 490                 495
Gln Val Gly Asp Leu Gln Asp Ser Leu Gln His Leu Val Lys Ile Gln
            500                 505                 510
Gly Thr Ile Lys Trp Arg Glu Asp His Val Ala Asp Lys Gln Ser Leu
            515                 520                 525
Ser Ser Lys Phe Trp Lys His Val Arg Tyr Gln Met Pro Val Pro Glu
        530                 535                 540
Arg Ala Ser Lys Thr Ala Ser Val Ala Ala Pro Leu Ser Gly Lys Ala
545                 550                 555                 560
Cys Leu Asp Leu Lys His Phe
                565

(2) INFORMATION FOR SEQ ID NO:25:

(i) SEQUENCE CHARACTERISTICS:
        (A) LENGTH: 328 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:25:

Met Gly Phe Trp Ile Leu Ala Ile Leu Thr Ile Leu Met Tyr Ser Thr
1               5                   10                  15
Ala Ala Lys Phe Ser Lys Gln Ser Trp Gly Leu Glu Asn Glu Ala Leu
                20                  25                  30
Ile Val Arg Cys Pro Arg Gln Gly Lys Pro Ser Tyr Thr Val Asp Trp
            35                  40                  45
Tyr Tyr Ser Gln Thr Asn Lys Ser Ile Pro Thr Gln Glu Arg Asn Arg
        50                  55                  60
Val Phe Ala Ser Gly Gln Leu Leu Lys Phe Leu Pro Ala Glu Val Ala
65                  70                  75                  80
Asp Ser Gly Ile Tyr Thr Cys Ile Val Arg Ser Pro Thr Phe Asn Arg
                85                  90                  95
Thr Gly Tyr Ala Asn Val Thr Ile Tyr Lys Lys Gln Ser Asp Cys Asn
            100                 105                 110
Val Pro Asp Tyr Leu Met Tyr Ser Thr Val Ser Gly Ser Glu Lys Asn
```

-continued

```
            115                 120                 125
Ser Lys Ile Tyr Cys Pro Thr Ile Asp Leu Tyr Asn Trp Thr Ala Pro
        130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325
```

(2) INFORMATION FOR SEQ ID NO:26:

(i) SEQUENCE CHARACTERISTICS:
       (A) LENGTH: 398 amino acids
       (B) TYPE: amino acid
       (C) STRANDEDNESS: Not Relevant
       (D) TOPOLOGY: linear (ii) MOLECULE TYPE: peptide (xi) SEQUENCE DESCRIPTION: SEQ ID NO:26:

```
Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
                20                  25                  30

Arg His Tyr Lys Arg Glu Phe Arg Leu Gly Glu Pro Val Ala Leu
            35                  40                  45

Arg Cys Pro Gln Val Pro Tyr Trp Leu Trp Ala Ser Val Ser Pro Arg
50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
                100                 105                 110

Ala Ser Tyr Cys Asp Lys Met Ser Ile Glu Leu Arg Val Phe Glu Asn
            115                 120                 125

Thr Asp Ala Phe Leu Pro Phe Ile Ser Tyr Pro Gln Ile Leu Thr Leu
```

-continued

```
            130                 135                 140
Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
                180                 185                 190

Leu Val His Asp Val Ala Leu Glu Asp Ala Gly Tyr Tyr Arg Cys Val
                195                 200                 205

Leu Thr Phe Ala His Glu Gly Gln Gln Tyr Asn Ile Thr Arg Ser Ile
                210                 215                 220

Glu Leu Arg Ile Lys Lys Lys Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
                260                 265                 270

Trp Trp Thr Ala Asn Asp Thr His Ile Glu Ser Ala Tyr Pro Gly Gly
                275                 280                 285

Arg Val Thr Glu Gly Pro Arg Gln Glu Tyr Ser Glu Asn Asn Glu Asn
290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
                340                 345                 350

Val Leu Ala Pro Leu Ser Leu Ala Phe Leu Val Leu Gly Gly Ile Trp
                355                 360                 365

Met His Arg Arg Cys Lys His Arg Thr Gly Lys Ala Asp Gly Leu Thr
370                 375                 380

Val Leu Trp Pro His His Gln Asp Phe Gln Ser Tyr Pro Lys
385                 390                 395
```

(2) INFORMATION FOR SEQ ID NO:27:

(i) SEQUENCE CHARACTERISTICS:
        (A) LENGTH: 410 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:27:

```
Met Phe Ile Leu Leu Val Leu Val Thr Gly Val Ser Ala Phe Thr Thr
1               5                   10                  15

Pro Thr Val Val His Thr Gly Lys Val Ser Glu Ser Pro Ile Thr Ser
                20                  25                  30

Glu Lys Pro Thr Val His Gly Asp Asn Cys Gln Phe Arg Gly Arg Glu
                35                  40                  45

Phe Lys Ser Glu Leu Arg Leu Glu Gly Glu Pro Val Val Leu Arg Cys
                50                  55                  60

Pro Leu Ala Pro His Ser Asp Ile Ser Ser Ser His Ser Phe Leu
65                  70                  75                  80

Thr Trp Ser Lys Leu Asp Ser Ser Gln Leu Ile Pro Arg Asp Glu Pro
```

```
              85                  90                      95
Arg Met Trp Val Lys Gly Asn Ile Leu Trp Ile Leu Pro Ala Val Gln
                100             105             110

Gln Asp Ser Gly Thr Tyr Ile Cys Thr Phe Arg Asn Ala Ser His Cys
            115             120             125

Glu Gln Met Ser Val Glu Leu Lys Val Phe Lys Asn Thr Glu Ala Ser
130             135             140

Leu Pro His Val Ser Tyr Leu Gln Ile Ser Ala Leu Ser Thr Thr Gly
145             150             155             160

Leu Leu Val Cys Pro Asp Leu Lys Glu Phe Ile Ser Ser Asn Ala Asp
                165             170             175

Gly Lys Ile Gln Trp Tyr Lys Gly Ala Ile Leu Leu Asp Lys Gly Asn
                180             185             190

Lys Glu Phe Leu Ser Ala Gly Asp Pro Thr Arg Leu Leu Ile Ser Asn
                195             200             205

Thr Ser Met Asp Asp Ala Gly Tyr Tyr Arg Cys Val Met Thr Phe Thr
            210             215             220

Tyr Asn Gly Gln Glu Tyr Asn Ile Thr Arg Asn Ile Glu Leu Arg Val
225             230             235             240

Lys Gly Thr Thr Thr Glu Pro Ile Pro Val Ile Ile Ser Pro Leu Glu
                245             250             255

Thr Ile Pro Ala Ser Leu Gly Ser Arg Leu Ile Val Pro Cys Lys Val
                260             265             270

Phe Leu Gly Thr Gly Thr Ser Ser Asn Thr Ile Val Trp Trp Leu Ala
                275             280             285

Asn Ser Thr Phe Ile Ser Ala Ala Tyr Pro Arg Gly Arg Val Thr Glu
    290             295             300

Gly Leu His His Gln Tyr Ser Glu Asn Asp Glu Asn Tyr Val Glu Val
305             310             315             320

Ser Leu Ile Phe Asp Pro Val Thr Arg Glu Asp Leu His Thr Asp Phe
                325             330             335

Lys Cys Val Ala Ser Asn Pro Arg Ser Ser Gln Ser Leu His Thr Thr
                340             345             350

Val Lys Glu Val Ser Ser Thr Phe Ser Trp Ser Ile Ala Leu Ala Pro
                355             360             365

Leu Ser Leu Ile Ile Leu Val Val Gly Ala Ile Trp Met Arg Arg Arg
370             375             380

Cys Lys Arg Arg Ala Gly Lys Thr Tyr Gly Leu Thr Lys Leu Arg Thr
385             390             395             400

Asp Asn Gln Asp Phe Pro Ser Ser Pro Asn
                405             410

(2) INFORMATION FOR SEQ ID NO:28:

(i) SEQUENCE CHARACTERISTICS:
        (A) LENGTH: 541 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:28:

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
```

-continued

```
                  20                  25                  30
Gly Glu Pro Phe Tyr Leu Lys His Cys Ser Cys Ser Leu Ala His Glu
             35                  40                  45
Ile Glu Thr Thr Thr Lys Ser Trp Tyr Lys Ser Ser Gly Ser Gln Glu
 50                  55                  60
His Val Glu Leu Asn Pro Arg Ser Ser Arg Ile Ala Leu His Asp
 65                  70                  75                  80
Cys Val Leu Glu Phe Trp Pro Val Glu Leu Asn Asp Thr Gly Ser Tyr
                 85                  90                  95
Phe Phe Gln Met Lys Asn Tyr Thr Gln Lys Trp Lys Leu Asn Val Ile
                100                 105                 110
Arg Arg Asn Lys His Ser Cys Phe Thr Glu Arg Gln Val Thr Ser Lys
            115                 120                 125
Ile Val Glu Val Lys Lys Phe Phe Gln Ile Thr Cys Glu Asn Ser Tyr
130                 135                 140
Tyr Gln Thr Leu Val Asn Ser Thr Ser Leu Tyr Lys Asn Cys Lys Lys
145                 150                 155                 160
Leu Leu Leu Glu Asn Asn Lys Asn Pro Thr Ile Lys Lys Asn Ala Glu
                165                 170                 175
Phe Glu Asp Gln Gly Tyr Tyr Ser Cys Val His Phe Leu His His Asn
            180                 185                 190
Gly Lys Leu Phe Asn Ile Thr Lys Thr Phe Asn Ile Thr Ile Val Glu
        195                 200                 205
Asp Arg Ser Asn Ile Val Pro Val Leu Leu Gly Pro Lys Leu Asn His
        210                 215                 220
Val Ala Val Glu Leu Gly Lys Asn Val Arg Leu Asn Cys Ser Ala Leu
225                 230                 235                 240
Leu Asn Glu Glu Asp Val Ile Tyr Trp Met Phe Gly Glu Glu Asn Gly
            245                 250                 255
Ser Asp Pro Asn Ile His Glu Glu Lys Glu Met Arg Ile Met Thr Pro
            260                 265                 270
Glu Gly Lys Trp His Ala Ser Lys Val Leu Arg Ile Glu Asn Ile Gly
        275                 280                 285
Glu Ser Asn Leu Asn Val Leu Tyr Asn Cys Thr Val Ala Ser Thr Gly
        290                 295                 300
Gly Thr Asp Thr Lys Ser Phe Ile Leu Val Arg Lys Ala Asp Met Ala
305                 310                 315                 320
Asp Ile Pro Gly His Val Phe Thr Arg Gly Met Ile Ala Val Leu
            325                 330                 335
Ile Leu Val Ala Val Cys Leu Val Thr Val Cys Val Ile Tyr Arg
            340                 345                 350
Val Asp Leu Val Leu Phe Tyr Arg His Leu Thr Arg Arg Asp Glu Thr
        355                 360                 365
Leu Thr Asp Gly Lys Thr Tyr Asp Ala Phe Val Ser Tyr Leu Lys Glu
    370                 375                 380
Cys Arg Pro Glu Asn Gly Glu Glu His Thr Phe Ala Val Glu Ile Leu
385                 390                 395                 400
Pro Arg Val Leu Glu Lys His Phe Gly Tyr Lys Leu Cys Ile Phe Glu
            405                 410                 415
Arg Asp Val Val Pro Gly Gly Ala Val Val Asp Glu Ile His Ser Leu
            420                 425                 430
Ile Glu Lys Ser Arg Arg Leu Ile Ile Val Leu Ser Lys Ser Tyr Met
        435                 440                 445
```

```
Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
                485                 490                 495

Val Leu Lys Trp Lys Ala Asp Lys Ser Leu Ser Tyr Asn Ser Arg Phe
                500                 505                 510

Trp Lys Asn Leu Leu Tyr Leu Met Pro Ala Lys Thr Val Lys Pro Gly
            515                 520                 525

Arg Asp Glu Pro Glu Val Leu Pro Val Leu Ser Glu Ser
    530                 535                 540
```

(2) INFORMATION FOR SEQ ID NO:29:

(i) SEQUENCE CHARACTERISTICS:
        (A) LENGTH: 537 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:29:

```
Met His His Glu Glu Leu Ile Leu Thr Leu Cys Ile Leu Ile Val Lys
1                   5                   10                  15

Ser Ala Ser Lys Ser Cys Ile His Arg Ser Gln Ile His Val Val Glu
                20                  25                  30

Gly Glu Pro Phe Tyr Leu Lys Pro Cys Gly Ile Ser Ala Pro Val His
                35                  40                  45

Arg Asn Glu Thr Ala Thr Met Arg Trp Phe Lys Gly Ser Ala Ser His
50                  55                  60

Glu Tyr Arg Glu Leu Asn Asn Arg Ser Ser Pro Arg Val Thr Phe His
65                  70                  75                  80

Asp His Thr Leu Glu Phe Trp Pro Val Glu Met Glu Asp Glu Gly Thr
                85                  90                  95

Tyr Ile Ser Gln Val Gly Asn Asp Arg Arg Asn Trp Thr Leu Asn Val
                100                 105                 110

Thr Lys Arg Asn Lys His Ser Cys Phe Ser Asp Lys Leu Val Thr Ser
            115                 120                 125

Arg Asp Val Glu Val Asn Lys Ser Leu His Ile Thr Cys Lys Asn Pro
130                 135                 140

Asn Tyr Glu Glu Leu Ile Gln Asp Thr Trp Leu Tyr Lys Asn Cys Lys
145                 150                 155                 160

Glu Ile Ser Lys Thr Pro Arg Ile Leu Lys Asp Ala Glu Phe Gly Asp
                165                 170                 175

Glu Gly Tyr Tyr Ser Cys Val Phe Ser Val His His Asn Gly Thr Arg
                180                 185                 190

Tyr Asn Ile Thr Lys Thr Val Asn Ile Thr Val Ile Glu Gly Arg Ser
            195                 200                 205

Lys Val Thr Pro Ala Ile Leu Gly Pro Lys Cys Glu Lys Val Gly Val
            210                 215                 220

Glu Leu Gly Lys Asp Val Glu Leu Asn Cys Ser Ala Ser Leu Asn Lys
225                 230                 235                 240

Asp Asp Leu Phe Tyr Trp Ser Ile Arg Lys Glu Asp Ser Ser Asp Pro
                245                 250                 255
```

```
Asn Val Gln Glu Asp Arg Lys Glu Thr Thr Thr Trp Ile Ser Glu Gly
            260                 265                 270

Lys Leu His Ala Ser Lys Ile Leu Arg Phe Gln Lys Ile Thr Glu Asn
            275                 280                 285

Tyr Leu Asn Val Leu Tyr Asn Cys Thr Val Ala Asn Glu Glu Ala Ile
            290                 295                 300

Asp Thr Lys Ser Phe Val Leu Val Arg Lys Glu Ile Pro Asp Ile Pro
305                 310                 315                 320

Gly His Val Phe Thr Gly Gly Val Thr Val Leu Val Leu Ala Ser Val
                    325                 330                 335

Ala Ala Val Cys Ile Val Ile Leu Cys Val Ile Tyr Lys Val Asp Leu
                340                 345                 350

Val Leu Phe Tyr Arg Arg Ile Ala Glu Arg Asp Glu Thr Leu Thr Asp
            355                 360                 365

Gly Lys Thr Tyr Asp Ala Phe Val Ser Tyr Leu Lys Glu Cys His Pro
            370                 375                 380

Glu Asn Lys Glu Glu Tyr Thr Phe Ala Val Glu Thr Leu Pro Arg Val
385                 390                 395                 400

Leu Glu Lys Gln Phe Gly Tyr Lys Leu Cys Ile Phe Glu Arg Asp Val
                    405                 410                 415

Val Pro Gly Gly Ala Val Val Glu Glu Ile His Ser Leu Ile Glu Lys
                420                 425                 430

Ser Arg Arg Leu Ile Ile Val Leu Ser Gln Ser Tyr Leu Thr Asn Gly
            435                 440                 445

Ala Arg Arg Glu Leu Glu Ser Gly Leu His Glu Ala Leu Val Glu Arg
450                 455                 460

Lys Ile Lys Ile Ile Leu Ile Glu Phe Thr Pro Ala Ser Asn Ile Thr
465                 470                 475                 480

Phe Leu Pro Pro Ser Leu Lys Leu Leu Lys Ser Tyr Arg Val Leu Lys
                    485                 490                 495

Trp Arg Ala Asp Ser Pro Ser Met Asn Ser Arg Phe Trp Lys Asn Leu
                500                 505                 510

Val Tyr Leu Met Pro Ala Lys Ala Val Lys Pro Trp Arg Glu Glu Ser
            515                 520                 525

Glu Ala Arg Ser Val Leu Ser Ala Pro
530                 535

(2) INFORMATION FOR SEQ ID NO:30:

(i) SEQUENCE CHARACTERISTICS:
        (A) LENGTH: 576 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:30:

Met Glu Asn Met Lys Val Leu Leu Gly Leu Ile Cys Leu Met Val Pro
1               5                   10                  15

Leu Leu Ser Leu Glu Ile Asp Val Cys Thr Glu Tyr Pro Asn Gln Ile
            20                  25                  30

Val Leu Phe Leu Ser Val Asn Glu Ile Asp Ile Arg Lys Cys Pro Leu
            35                  40                  45

Thr Pro Asn Lys Met His Gly Asp Thr Ile Ile Trp Tyr Lys Asn Asp
50                  55                  60
```

-continued

```
Ser Lys Thr Pro Ile Ser Ala Asp Arg Asp Ser Arg Ile His Gln Gln
 65                  70                  75                  80

Asn Glu His Leu Trp Phe Val Pro Ala Lys Val Glu Asp Ser Gly Tyr
                 85                  90                  95

Tyr Tyr Cys Ile Val Arg Asn Ser Thr Tyr Cys Leu Lys Thr Lys Val
            100                 105                 110

Thr Val Thr Val Leu Glu Asn Asp Pro Gly Leu Cys Tyr Ser Thr Gln
        115                 120                 125

Ala Thr Phe Pro Gln Arg Leu His Ile Ala Gly Asp Gly Ser Leu Val
    130                 135                 140

Cys Pro Tyr Val Ser Tyr Phe Lys Asp Glu Asn Asn Glu Leu Pro Glu
145                 150                 155                 160

Val Gln Trp Tyr Lys Asn Cys Lys Pro Leu Leu Leu Asp Asn Val Ser
                165                 170                 175

Phe Phe Gly Val Lys Asp Lys Leu Leu Val Arg Asn Val Ala Glu Glu
            180                 185                 190

His Arg Gly Asp Tyr Ile Cys Arg Met Ser Tyr Thr Phe Arg Gly Lys
        195                 200                 205

Gln Tyr Pro Val Thr Arg Val Ile Gln Phe Ile Thr Ile Asp Glu Asn
    210                 215                 220

Lys Arg Asp Arg Pro Val Ile Leu Ser Pro Arg Asn Glu Thr Ile Glu
225                 230                 235                 240

Ala Asp Pro Gly Ser Met Ile Gln Leu Ile Cys Asn Val Thr Gly Gln
                245                 250                 255

Phe Ser Asp Leu Val Tyr Trp Lys Trp Asn Gly Ser Glu Ile Glu Trp
            260                 265                 270

Asn Asp Pro Phe Leu Ala Glu Asp Tyr Gln Phe Val Glu His Pro Ser
        275                 280                 285

Thr Lys Arg Lys Tyr Thr Leu Ile Thr Thr Leu Asn Ile Ser Glu Val
    290                 295                 300

Lys Ser Gln Phe Tyr Arg Tyr Pro Phe Ile Cys Val Val Lys Asn Thr
305                 310                 315                 320

Asn Ile Phe Glu Ser Ala His Val Gln Leu Ile Tyr Pro Val Pro Asp
                325                 330                 335

Phe Lys Asn Tyr Leu Ile Gly Gly Phe Ile Ile Leu Thr Ala Thr Ile
            340                 345                 350

Val Cys Cys Val Cys Ile Tyr Lys Val Phe Lys Val Asp Ile Val Leu
        355                 360                 365

Trp Tyr Arg Asp Ser Cys Ser Gly Phe Leu Pro Ser Lys Ala Ser Asp
    370                 375                 380

Gly Lys Thr Tyr Asp Ala Tyr Ile Leu Tyr Pro Lys Thr Leu Gly Glu
385                 390                 395                 400

Gly Ser Phe Ser Asp Leu Asp Thr Phe Val Phe Lys Leu Leu Pro Glu
                405                 410                 415

Val Leu Glu Gly Gln Phe Gly Tyr Lys Leu Phe Ile Tyr Gly Arg Asp
            420                 425                 430

Asp Tyr Val Gly Glu Asp Thr Ile Glu Val Thr Asn Glu Asn Val Lys
        435                 440                 445

Lys Ser Arg Arg Leu Ile Ile Ile Leu Val Arg Asp Met Gly Gly Phe
    450                 455                 460

Ser Trp Leu Gly Gln Ser Ser Glu Glu Gln Ile Ala Ile Tyr Asn Ala
465                 470                 475                 480
```

-continued

```
Leu Ile Gln Glu Gly Ile Lys Ile Val Leu Glu Leu Glu Lys Ile
                485                 490                 495

Gln Asp Tyr Glu Lys Met Pro Asp Ser Ile Gln Phe Ile Lys Gln Lys
                500                 505                 510

His Gly Val Ile Cys Trp Ser Gly Asp Phe Gln Glu Arg Pro Gln Ser
                515                 520                 525

Ala Lys Thr Arg Phe Trp Lys Asn Leu Arg Tyr Gln Met Pro Ala Gln
                530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
                565                 570                 575
```

(2) INFORMATION FOR SEQ ID NO:31:

(i) SEQUENCE CHARACTERISTICS:
        (A) LENGTH: 569 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:31:

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
                35                  40                  45

Asn Glu His Lys Gly Thr Ile Thr Trp Tyr Lys Asp Asp Ser Lys Thr
50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
                100                 105                 110

Phe Val Glu Asn Glu Pro Asn Leu Cys Tyr Asn Ala Gln Ala Ile Phe
                115                 120                 125

Lys Gln Lys Leu Pro Val Ala Gly Asp Gly Gly Leu Val Cys Pro Tyr
                130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
                180                 185                 190

Asn Tyr Thr Cys His Ala Ser Tyr Thr Tyr Leu Gly Lys Gln Tyr Pro
                195                 200                 205

Ile Thr Arg Val Ile Glu Phe Ile Thr Leu Glu Glu Asn Lys Pro Thr
                210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255
```

```
Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
            290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
            515                 520                 525

Arg Phe Trp Lys Asn Val Arg Tyr His Met Pro Val Gln Arg Arg Ser
            530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
            565
```

(2) INFORMATION FOR SEQ ID NO:32:

(i) SEQUENCE CHARACTERISTICS:
        (A) LENGTH: 555 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:32:

```
Met His Lys Met Thr Ser Thr Phe Leu Leu Ile Gly His Leu Ile Leu
1               5                   10                  15

Leu Ile Pro Leu Phe Ser Ala Glu Glu Cys Val Ile Cys Asn Tyr Phe
            20                  25                  30
```

-continued

```
Val Leu Val Gly Glu Pro Thr Ala Ile Ser Cys Pro Val Ile Thr Leu
             35                  40                  45

Pro Met Leu His Ser Asp Tyr Asn Leu Thr Trp Tyr Arg Asn Gly Ser
         50                  55                  60

Asn Met Pro Ile Thr Thr Glu Arg Arg Ala Arg Ile His Gln Arg Lys
 65                  70                  75                  80

Gly Leu Leu Trp Phe Ile Pro Ala Ala Leu Glu Asp Ser Gly Leu Tyr
                 85                  90                  95

Glu Cys Glu Val Arg Ser Leu Asn Arg Ser Lys Gln Lys Ile Ile Asn
            100                 105                 110

Leu Lys Val Phe Lys Asn Asp Asn Gly Leu Cys Phe Asn Gly Glu Met
            115                 120                 125

Lys Tyr Asp Gln Ile Val Lys Ser Ala Asn Ala Gly Lys Ile Ile Cys
130                 135                 140

Pro Asp Leu Glu Asn Phe Lys Asp Glu Asp Asn Ile Asn Pro Glu Ile
145                 150                 155                 160

His Trp Tyr Lys Glu Cys Lys Ser Gly Phe Leu Glu Asp Lys Arg Leu
                165                 170                 175

Val Leu Ala Glu Gly Glu Asn Ala Ile Leu Ile Leu Asn Val Thr Ile
            180                 185                 190

Gln Asp Lys Gly Asn Tyr Thr Cys Arg Met Val Tyr Thr Tyr Met Gly
            195                 200                 205

Lys Gln Tyr Asn Val Ser Arg Thr Met Asn Leu Glu Val Lys Glu Ser
210                 215                 220

Pro Leu Lys Met Arg Pro Glu Phe Ile Tyr Pro Asn Asn Asn Thr Ile
225                 230                 235                 240

Glu Val Glu Leu Gly Ser His Val Val Met Glu Cys Asn Val Ser Ser
                245                 250                 255

Gly Val Tyr Gly Leu Leu Pro Tyr Trp Gln Val Asn Asp Glu Asp Val
            260                 265                 270

Asp Ser Phe Asp Ser Thr Tyr Arg Glu Gln Phe Tyr Glu Glu Gly Met
            275                 280                 285

Pro His Gly Ile Ala Val Ser Gly Thr Lys Phe Asn Ile Ser Glu Val
290                 295                 300

Lys Leu Lys Asp Tyr Ala Tyr Lys Phe Phe Cys His Phe Ile Tyr Asp
305                 310                 315                 320

Ser Gln Glu Phe Thr Ser Tyr Ile Lys Leu Glu His Pro Val Gln Asn
                325                 330                 335

Ile Arg Gly Tyr Leu Ile Gly Gly Ile Ser Leu Ile Phe Leu Leu
            340                 345                 350

Phe Leu Ile Leu Ile Val Tyr Lys Ile Phe Lys Ile Asp Ile Val Leu
            355                 360                 365

Trp Tyr Arg Ser Ser Cys His Pro Leu Leu Gly Lys Lys Val Ser Asp
370                 375                 380

Gly Lys Ile Tyr Asp Ala Tyr Val Leu Tyr Pro Lys Asn Arg Glu Ser
385                 390                 395                 400

Cys Leu Tyr Ser Ser Asp Ile Phe Ala Leu Lys Ile Leu Pro Glu Val
                405                 410                 415

Leu Glu Arg Gln Cys Gly Tyr Asn Leu Phe Ile Phe Gly Arg Asn Asp
            420                 425                 430

Leu Ala Gly Glu Ala Val Ile Asp Val Thr Asp Glu Lys Ile His Gln
            435                 440                 445

Ser Arg Arg Val Ile Ile Ile Leu Val Pro Glu Pro Ser Cys Tyr Gly
```

```
        450                 455                 460
Ile Leu Glu Asp Ala Ser Glu Lys His Leu Ala Val Tyr Asn Ala Leu
465                 470                 475                 480

Ile Gln Asp Gly Ile Lys Ile Ile Leu Ile Glu Leu Glu Lys Ile Glu
                    485                 490                 495

Asp Tyr Ala Asn Met Pro Glu Ser Ile Lys Tyr Val Lys Gln Lys Tyr
                500                 505                 510

Gly Ala Ile Arg Trp Thr Gly Asp Phe Ser Glu Arg Ser His Ser Ala
            515                 520                 525

Ser Thr Arg Phe Trp Lys Lys Val Arg Tyr His Met Pro Ser Arg Lys
        530                 535                 540

His Gly Ser Ser Ser Gly Phe His Leu Ser Ser
545                 550                 555

(2) INFORMATION FOR SEQ ID NO:33:

(i) SEQUENCE CHARACTERISTICS:
        (A) LENGTH: 802 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:33:

Met Arg Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                    85                  90                  95

Gly Arg Tyr Leu Cys Leu Ala Arg Gly Ser Met Ile Val Leu Gln Asn
                100                 105                 110

Leu Thr Leu Ile Thr Gly Asp Ser Leu Thr Ser Ser Asn Asp Asp Glu
            115                 120                 125

Asp Pro Lys Ser His Arg Asp Pro Ser Asn Arg His Ser Tyr Pro Gln
        130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
                180                 185                 190

Gly Glu Asn Arg Ile Gly Gly Ile Arg Leu Arg His Gln His Trp Ser
            195                 200                 205

Leu Val Met Glu Ser Val Val Pro Ser Asp Arg Gly Thr Tyr Thr Cys
        210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
```

-continued

```
                245                 250                 255
Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Val Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Gly Lys Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670
```

-continued

```
Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
            690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
                740                 745                 750

Glu Tyr Leu Asp Leu Arg Leu Thr Phe Gly Pro Tyr Ser Pro Ser Gly
            755                 760                 765

Gly Asp Ala Ser Ser Thr Cys Ser Ser Ser Asp Ser Val Phe Ser His
770                 775                 780

Asp Pro Leu Pro Leu Gly Ser Ser Phe Pro Phe Gly Ser Gly Val
785                 790                 795                 800

Gln Thr
```

(2) INFORMATION FOR SEQ ID NO:34:

(i) SEQUENCE CHARACTERISTICS:
        (A) LENGTH: 2537 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2004

(xi) SEQUENCE DESCRIPTION: SEQ ID NO:34:

```
GAT GGA TGC ACT GAC TGG TCT ATC GAT ATC AAG AAA TAT CAA GTT TTG        48
Asp Gly Cys Thr Asp Trp Ser Ile Asp Ile Lys Lys Tyr Gln Val Leu
 1               5                  10                  15

GTG GGA GAG CCT GTT CGA ATC AAA TGT GCA CTC TTT TAT GGT TAT ATC        96
Val Gly Glu Pro Val Arg Ile Lys Cys Ala Leu Phe Tyr Gly Tyr Ile
                20                  25                  30

AGA ACA AAT TAC TCC CTT GCC CAA AGT GCT GGA CTC AGT TTG ATG TGG       144
Arg Thr Asn Tyr Ser Leu Ala Gln Ser Ala Gly Leu Ser Leu Met Trp
            35                  40                  45

TAC AAA AGT TCT GGT CCT GGA GAC TTT GAA GAG CCA ATA GCC TTT GAC       192
Tyr Lys Ser Ser Gly Pro Gly Asp Phe Glu Glu Pro Ile Ala Phe Asp
    50                  55                  60

GGA AGT AGA ATG AGC AAA GAA GAA GAC TCC ATT TGG TTC CGG CCA ACA       240
Gly Ser Arg Met Ser Lys Glu Glu Asp Ser Ile Trp Phe Arg Pro Thr
65                  70                  75                  80

TTG CTA CAG GAC AGT GGT CTC TAC GCC TGT GTC ATC AGG AAC TCC ACT       288
Leu Leu Gln Asp Ser Gly Leu Tyr Ala Cys Val Ile Arg Asn Ser Thr
                85                  90                  95

TAC TGT ATG AAA GTA TCC ATC TCA CTG ACA GTG GGT GAA AAT GAC ACT       336
Tyr Cys Met Lys Val Ser Ile Ser Leu Thr Val Gly Glu Asn Asp Thr
            100                 105                 110

GGA CTC TGC TAT AAT TCC AAG ATG AAG TAT TTT GAA AAA GCT GAA CTT       384
Gly Leu Cys Tyr Asn Ser Lys Met Lys Tyr Phe Glu Lys Ala Glu Leu
    115                 120                 125

AGC AAA AGC AAG GAA ATT TCA TGC CGT GAC ATA GAG GAT TTT CTA CTG       432
Ser Lys Ser Lys Glu Ile Ser Cys Arg Asp Ile Glu Asp Phe Leu Leu
130                 135                 140
```

```
CCA ACC AGA GAA CCT GAA ATC CTT TGG TAC AAG GAA TGC AGG ACA AAA      480
Pro Thr Arg Glu Pro Glu Ile Leu Trp Tyr Lys Glu Cys Arg Thr Lys
145                 150                 155                 160

ACA TGG AGG CCA AGT ATT GTA TTC AAA AGA GAT ACT CTG CTT ATA AGA      528
Thr Trp Arg Pro Ser Ile Val Phe Lys Arg Asp Thr Leu Leu Ile Arg
                165                 170                 175

GAA GTC AGA GAA GAT GAC ATT GGA AAT TAT ACC TGT GAA TTA AAA TAT      576
Glu Val Arg Glu Asp Asp Ile Gly Asn Tyr Thr Cys Glu Leu Lys Tyr
            180                 185                 190

GGA GGC TTT GTT GTG AGA AGA ACT ACT GAA TTA ACT GTT ACA GCC CCT      624
Gly Gly Phe Val Val Arg Arg Thr Thr Glu Leu Thr Val Thr Ala Pro
        195                 200                 205

CTG ACT GAT AAG CCA CCC AAG CTT TTG TAT CCT ATG GAA AGT AAA CTG      672
Leu Thr Asp Lys Pro Pro Lys Leu Leu Tyr Pro Met Glu Ser Lys Leu
210                 215                 220

ACA ATT CAG GAG ACC CAG CTG GGT GAC TCT GCT AAT CTA ACC TGC AGA      720
Thr Ile Gln Glu Thr Gln Leu Gly Asp Ser Ala Asn Leu Thr Cys Arg
225                 230                 235                 240

GCT TTC TTT GGG TAC AGC GGA GAT GTC AGT CCT TTA ATT TAC TGG ATG      768
Ala Phe Phe Gly Tyr Ser Gly Asp Val Ser Pro Leu Ile Tyr Trp Met
                245                 250                 255

AAA GGA GAA AAA TTT ATT GAA GAT CTG GAT GAA AAT CGA GTT TGG GAA      816
Lys Gly Glu Lys Phe Ile Glu Asp Leu Asp Glu Asn Arg Val Trp Glu
            260                 265                 270

AGT GAC ATT AGA ATT CTT AAG GAG CAT CTT GGG GAA CAG GAA GTT TCC      864
Ser Asp Ile Arg Ile Leu Lys Glu His Leu Gly Glu Gln Glu Val Ser
        275                 280                 285

ATC TCA TTA ATT GTG GAC TCT GTG GAA GAA GGT GAC TTG GGA AAT TAC      912
Ile Ser Leu Ile Val Asp Ser Val Glu Glu Gly Asp Leu Gly Asn Tyr
290                 295                 300

TCC TGT TAT GTT GAA AAT GGA AAT GGA CGT CGA CAC GCC AGC GTT CTC      960
Ser Cys Tyr Val Glu Asn Gly Asn Gly Arg Arg His Ala Ser Val Leu
305                 310                 315                 320

CTT CAT AAA CGA GAG CTA ATG TAC ACA GTG GAA CTT GCT GGA GGC CTT     1008
Leu His Lys Arg Glu Leu Met Tyr Thr Val Glu Leu Ala Gly Gly Leu
                325                 330                 335

GGT GCT ATA CTC TTG CTG CTT GTA TGT TTG GTG ACC ATC TAC AAG TGT     1056
Gly Ala Ile Leu Leu Leu Leu Val Cys Leu Val Thr Ile Tyr Lys Cys
            340                 345                 350

TAC AAG ATA GAA ATC ATG CTC TTC TAC AGG AAT CAT TTT GGA GCT GAA     1104
Tyr Lys Ile Glu Ile Met Leu Phe Tyr Arg Asn His Phe Gly Ala Glu
        355                 360                 365

GAG CTC GAT GGA GAC AAT AAA GAT TAT GAT GCA TAC TTA TCA TAC ACC     1152
Glu Leu Asp Gly Asp Asn Lys Asp Tyr Asp Ala Tyr Leu Ser Tyr Thr
370                 375                 380

AAA GTG GAT CCT GAC CAG TGG AAT CAA GAG ACT GGG GAA GAA GAA CGT     1200
Lys Val Asp Pro Asp Gln Trp Asn Gln Glu Thr Gly Glu Glu Glu Arg
385                 390                 395                 400

TTT GCC CTT GAA ATC CTA CCT GAT ATG CTT GAA AAG CAT TAT GGA TAT     1248
Phe Ala Leu Glu Ile Leu Pro Asp Met Leu Glu Lys His Tyr Gly Tyr
                405                 410                 415

AAG TTG TTT ATA CCA GAT AGA GAT TTA ATC CCA ACT GGA ACA TAC ATT     1296
Lys Leu Phe Ile Pro Asp Arg Asp Leu Ile Pro Thr Gly Thr Tyr Ile
            420                 425                 430

GAA GAT GTG GCA AGA TGT GTA GAT CAA AGC AAG CGG CTG ATT ATT GTC     1344
Glu Asp Val Ala Arg Cys Val Asp Gln Ser Lys Arg Leu Ile Ile Val
        435                 440                 445

ATG ACC CCA AAT TAC GTA GTT AGA AGG GGC TGG AGC ATC TTT GAG CTG     1392
Met Thr Pro Asn Tyr Val Val Arg Arg Gly Trp Ser Ile Phe Glu Leu
```

```
                450                       455                       460
GAA ACC AGA CTT CGA AAT ATG CTT GTG ACT GGA GAA ATT AAA GTG ATT        1440
Glu Thr Arg Leu Arg Asn Met Leu Val Thr Gly Glu Ile Lys Val Ile
465                     470                     475                 480

CTA ATT GAA TGC AGT GAA CTG AGA GGA ATT ATG AAC TAC CAG GAG GTG        1488
Leu Ile Glu Cys Ser Glu Leu Arg Gly Ile Met Asn Tyr Gln Glu Val
                    485                     490                 495

GAG GCC CTG AAG CAC ACC ATC AAG CTC CTG ACG GTC ATT AAA TGG CAT        1536
Glu Ala Leu Lys His Thr Ile Lys Leu Leu Thr Val Ile Lys Trp His
                500                     505                 510

GGA CCA AAA TGC AAC AAG TTG AAC TCC AAG TTC TGG AAA CGT TTA CAG        1584
Gly Pro Lys Cys Asn Lys Leu Asn Ser Lys Phe Trp Lys Arg Leu Gln
            515                     520                 525

TAT GAA ATG CCT TTT AAG AGG ATA GAA CCC ATT ACA CAT GAG CAG GCT        1632
Tyr Glu Met Pro Phe Lys Arg Ile Glu Pro Ile Thr His Glu Gln Ala
        530                     535                 540

TTA GAT GTC AGT GAG CAA GGG CCT TTT GGG GAG CTG CAG ACT GTC TCG        1680
Leu Asp Val Ser Glu Gln Gly Pro Phe Gly Glu Leu Gln Thr Val Ser
545                     550                     555                 560

GCC ATT TCC ATG GCC GCG GCC ACC TCC ACA GCT CTA GCC ACT GCC CAT        1728
Ala Ile Ser Met Ala Ala Ala Thr Ser Thr Ala Leu Ala Thr Ala His
                    565                     570                 575

CCA GAT CTC CGT TCT ACC TTT CAC AAC ACG TAC CAT TCA CAA ATG CGT        1776
Pro Asp Leu Arg Ser Thr Phe His Asn Thr Tyr His Ser Gln Met Arg
                580                     585                 590

CAG AAA CAC TAC TAC CGA AGC TAT GAG TAC GAC GTA CCT CCT ACC GGC        1824
Gln Lys His Tyr Tyr Arg Ser Tyr Glu Tyr Asp Val Pro Pro Thr Gly
            595                     600                 605

ACC CTG CCT CTT ACC TCC ATA GGC AAT CAG CAT ACC TAC TGT AAC ATC        1872
Thr Leu Pro Leu Thr Ser Ile Gly Asn Gln His Thr Tyr Cys Asn Ile
        610                     615                 620

CCT ATG ACA CTC ATC AAC GGG CAG CGG CCA CAG ACA AAA TCG AGC AGG        1920
Pro Met Thr Leu Ile Asn Gly Gln Arg Pro Gln Thr Lys Ser Ser Arg
625                     630                     635                 640

GAG CAG AAT CCA GAT GAG GCC CAC ACA AAC AGT GCC ATC CTG CCG CTG        1968
Glu Gln Asn Pro Asp Glu Ala His Thr Asn Ser Ala Ile Leu Pro Leu
                    645                     650                 655

TTG CCA AGG GAG ACC AGT ATA TCC AGT GTG ATA TGG TGACAGAAAA            2014
Leu Pro Arg Glu Thr Ser Ile Ser Ser Val Ile Trp
                660                     665

GCAAGGGACA TCCCGTCCCT GGGAGGTTGA GTGGAATCTG CAGTCCAGTG CCTGGAACTA    2074

AATCCTCGAC TGCTGCTGTT AAAAAACATG CATTAGAATC TTTAGAACAC GAGGAAAAAC    2134

AGGGTCTTGT ACATATGTTT TTTGGAATTT CTTTGTAGCA TCAGTGTCCT CCTGTTTTAC    2194

CATGTCTTTT ACCATTACAT TTTTTGACTT TGTTTTATAT GTCGTTGGAA TTTGTAAATT    2254

TACATTTTTT TTAAAGAAGA GACTGATGTG TAGATAGAAA ACCCTTTTTT TGCTTCATTA    2314

GTTTAGTTTT AGAATGGGTT TTTATTTTAT TTCCTTTTTT AAAATTTTAC TTTGCTTTTA    2374

ACATTTCCTT GGGGTGCTTG AACAAATCTA TCCGATGGGA CAAGGAGCAC CGGATTCTTT    2434

CTCGGGTTCT GCCTAGCATC AACTGGGCCA CGTCGGCCTT CAGAGAACAG TGCAACAAAT    2494

GCCAGCATTG CCATTCGGGG GGAAAAAAAA AAAAAAAAA AAA                       2537

(2) INFORMATION FOR SEQ ID NO:35:

(i) SEQUENCE CHARACTERISTICS:
        (A) LENGTH: 668 amino acids
        (B) TYPE: amino acid
        (D) TOPOLOGY: linear
```

-continued (ii) MOLECULE TYPE: protein (xi) SEQUENCE DESCRIPTION: SEQ ID NO:35:

Asp Gly Cys Thr Asp Trp Ser Ile Asp Ile Lys Tyr Gln Val Leu
 1               5                  10                  15

Val Gly Glu Pro Val Arg Ile Lys Cys Ala Leu Phe Tyr Gly Tyr Ile
                 20                  25                  30

Arg Thr Asn Tyr Ser Leu Ala Gln Ser Ala Gly Leu Ser Leu Met Trp
             35                  40                  45

Tyr Lys Ser Ser Gly Pro Gly Asp Phe Glu Glu Pro Ile Ala Phe Asp
     50                  55                  60

Gly Ser Arg Met Ser Lys Glu Glu Asp Ser Ile Trp Phe Arg Pro Thr
 65                  70                  75                  80

Leu Leu Gln Asp Ser Gly Leu Tyr Ala Cys Val Ile Arg Asn Ser Thr
                 85                  90                  95

Tyr Cys Met Lys Val Ser Ile Ser Leu Thr Val Gly Glu Asn Asp Thr
            100                 105                 110

Gly Leu Cys Tyr Asn Ser Lys Met Lys Tyr Phe Glu Lys Ala Glu Leu
            115                 120                 125

Ser Lys Ser Lys Glu Ile Ser Cys Arg Asp Ile Glu Asp Phe Leu Leu
130                 135                 140

Pro Thr Arg Glu Pro Glu Ile Leu Trp Tyr Lys Glu Cys Arg Thr Lys
145                 150                 155                 160

Thr Trp Arg Pro Ser Ile Val Phe Lys Arg Asp Thr Leu Leu Ile Arg
                165                 170                 175

Glu Val Arg Glu Asp Asp Ile Gly Asn Tyr Thr Cys Glu Leu Lys Tyr
            180                 185                 190

Gly Gly Phe Val Val Arg Arg Thr Thr Glu Leu Thr Val Thr Ala Pro
            195                 200                 205

Leu Thr Asp Lys Pro Pro Lys Leu Leu Tyr Pro Met Glu Ser Lys Leu
    210                 215                 220

Thr Ile Gln Glu Thr Gln Leu Gly Asp Ser Ala Asn Leu Thr Cys Arg
225                 230                 235                 240

Ala Phe Phe Gly Tyr Ser Gly Asp Val Ser Pro Leu Ile Tyr Trp Met
                245                 250                 255

Lys Gly Glu Lys Phe Ile Glu Asp Leu Asp Glu Asn Arg Val Trp Glu
            260                 265                 270

Ser Asp Ile Arg Ile Leu Lys Glu His Leu Gly Glu Gln Glu Val Ser
    275                 280                 285

Ile Ser Leu Ile Val Asp Ser Val Glu Glu Gly Asp Leu Gly Asn Tyr
290                 295                 300

Ser Cys Tyr Val Glu Asn Gly Asn Gly Arg Arg His Ala Ser Val Leu
305                 310                 315                 320

Leu His Lys Arg Glu Leu Met Tyr Thr Val Glu Leu Ala Gly Gly Leu
                325                 330                 335

Gly Ala Ile Leu Leu Leu Leu Val Cys Leu Val Thr Ile Tyr Lys Cys
            340                 345                 350

Tyr Lys Ile Glu Ile Met Leu Phe Tyr Arg Asn His Phe Gly Ala Glu
            355                 360                 365

Glu Leu Asp Gly Asp Asn Lys Asp Tyr Asp Ala Tyr Leu Ser Tyr Thr
    370                 375                 380

Lys Val Asp Pro Asp Gln Trp Asn Gln Glu Thr Gly Glu Glu Glu Arg
385                 390                 395                 400

```
Phe Ala Leu Glu Ile Leu Pro Asp Met Leu Glu Lys His Tyr Gly Tyr
                405                 410                 415
Lys Leu Phe Ile Pro Asp Arg Asp Leu Ile Pro Thr Gly Thr Tyr Ile
            420                 425                 430
Glu Asp Val Ala Arg Cys Val Asp Gln Ser Lys Arg Leu Ile Ile Val
        435                 440                 445
Met Thr Pro Asn Tyr Val Val Arg Arg Gly Trp Ser Ile Phe Glu Leu
    450                 455                 460
Glu Thr Arg Leu Arg Asn Met Leu Val Thr Gly Glu Ile Lys Val Ile
465                 470                 475                 480
Leu Ile Glu Cys Ser Glu Leu Arg Gly Ile Met Asn Tyr Gln Glu Val
                485                 490                 495
Glu Ala Leu Lys His Thr Ile Lys Leu Leu Thr Val Ile Lys Trp His
                500                 505                 510
Gly Pro Lys Cys Asn Lys Leu Asn Ser Lys Phe Trp Lys Arg Leu Gln
            515                 520                 525
Tyr Glu Met Pro Phe Lys Arg Ile Glu Pro Ile Thr His Glu Gln Ala
    530                 535                 540
Leu Asp Val Ser Glu Gln Gly Pro Phe Gly Glu Leu Gln Thr Val Ser
545                 550                 555                 560
Ala Ile Ser Met Ala Ala Ala Thr Ser Thr Ala Leu Ala Thr Ala His
                565                 570                 575
Pro Asp Leu Arg Ser Thr Phe His Asn Thr Tyr His Ser Gln Met Arg
                580                 585                 590
Gln Lys His Tyr Tyr Arg Ser Tyr Glu Tyr Asp Val Pro Pro Thr Gly
            595                 600                 605
Thr Leu Pro Leu Thr Ser Ile Gly Asn Gln His Thr Tyr Cys Asn Ile
    610                 615                 620
Pro Met Thr Leu Ile Asn Gly Gln Arg Pro Gln Thr Lys Ser Ser Arg
625                 630                 635                 640
Glu Gln Asn Pro Asp Glu Ala His Thr Asn Ser Ala Ile Leu Pro Leu
                645                 650                 655
Leu Pro Arg Glu Thr Ser Ile Ser Ser Val Ile Trp
            660                 665
```

(2) INFORMATION FOR SEQ ID NO:36:

(i) SEQUENCE CHARACTERISTICS:
        (A) LENGTH: 570 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:36:

```
Met Thr Leu Leu Trp Cys Val Val Ser Leu Tyr Phe Tyr Gly Ile Leu
1               5                   10                  15
Gln Ser Asp Ala Ser Glu Arg Cys Asp Asp Trp Gly Leu Asp Thr Met
                20                  25                  30
Arg Gln Ile Gln Val Phe Glu Asp Glu Pro Ala Arg Ile Lys Cys Pro
            35                  40                  45
Leu Phe Glu His Phe Leu Lys Phe Asn Tyr Ser Thr Ala His Ser Ala
    50                  55                  60
Gly Leu Thr Leu Ile Trp Tyr Trp Thr Arg Gln Asp Arg Asp Leu Glu
65                  70                  75                  80
```

-continued

```
Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
        130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Ile Val Val Tyr His Val Tyr Trp Leu Glu
        370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
        435                 440                 445

Ile Val Thr Asp Glu Thr Leu Ser Phe Ile Gln Lys Ser Arg Arg Leu
        450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495
```

```
Asn Val Ile Leu Val Gln Tyr Lys Ala Val Lys Glu Thr Lys Val Lys
            500                 505                 510

Glu Leu Lys Arg Ala Lys Thr Val Leu Thr Val Ile Lys Trp Lys Gly
            515                 520                 525

Glu Lys Ser Lys Tyr Pro Gln Gly Arg Phe Trp Lys Gln Leu Gln Val
    530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565             570
```

What is claimed is:

1. A binding compound, comprising an antigen binding site from an antibody which specifically binds to an antigenic fragment of SEQ ID NO:6 or 12.

2. The binding compound of claim 1, wherein:
   a) said antigen fragment is from a primate or rodent protein;
   b) said binding compound is an Fv, Fab, or Fab2 fragment;
   c) said binding compound is conjugated to another chemical moiety; or
   d) said antibody:
      i) is a polyclonal antibody;
      ii) binds to a denatured IL-1RD9;
      iii is attached to a solid substrate; or
      iv) is detectably labeled.

3. A kit comprising said binding compound of claim 1, and:
   a) a compartment or container adapted to contain said binding compound; and/optionally
   b) instructions for use or disposal of reagents in said kit.

4. A composition comprising a binding compound of claim 1 which is sterile, and a carrier, or said binding compound of claim 1 and a carrier, wherein said carrier is an aqueous compound.

5. The binding compound of claim 1, wherein said binding compound is an Fv, Fab, or Fab2 fragment.

6. The binding compound of claim 1, wherein said antibody is raised against a polypeptide consisting of 12 or more contiguous amino acids of SEQ ID NO:6 or 12.

7. The binding compound of claim 1, wherein said antibody is a polyclonal antibody.

8. A method of making an antibody, comprising immunizing an animal with an immunogenic amount of a primate IL-1 RD9 polypeptide having the amino acid sequence of SEQ ID NO: 6 or 12, thereby causing said antibody to be produced.

9. A binding compound, comprising an antigen binding site from an antibody which specifically binds to a polypeptide consisting of 8 or more contiguous amino acids of SEQ ID NO: 6.

10. The binding compound of claim 9, wherein said polypeptide comprises at least 12 contiguous amino acids of SEQ ID NO:6.

11. The binding compound of claim 9, wherein said polypeptide is the mature polypeptide of SEQ ID NO:6.

12. A binding compound, comprising an antigen binding site from an antibody which specifically binds to a polypeptide consisting of 8 or more contiguous amino acids of SEQ ID NO: 12.

13. The binding compound of claim 12, wherein said polypeptide comprises at least 12 contiguous amino acids of SEQ ID NO:12.

14. The binding compound of claim 12, wherein said polypeptide is the mature polypeptide of SEQ ID NO:12.

* * * * *